(12) United States Patent
Wang et al.

(10) Patent No.: US 9,694,061 B2
(45) Date of Patent: *Jul. 4, 2017

(54) FULLY HUMAN ANTIBODIES TO HIGH MOLECULAR WEIGHT-MELANOMA ASSOCIATED ANTIGEN AND USES THEREOF

(71) Applicant: University of Pittsburgh—Of the Commonwealth System of Higher Education, Pittsburgh, PA (US)

(72) Inventors: Xinhui Wang, Boston, MA (US); Soldano Ferrone, Boston, MA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/887,700

(22) Filed: Oct. 20, 2015

(65) Prior Publication Data

US 2016/0038578 A1   Feb. 11, 2016

Related U.S. Application Data

(62) Division of application No. 13/912,429, filed on Jun. 7, 2013, now Pat. No. 9,193,796, which is a division of application No. 13/123,489, filed as application No. PCT/US2009/060903 on Oct. 15, 2009, now Pat. No. 8,476,410.

(60) Provisional application No. 61/106,055, filed on Oct. 16, 2008.

(51) Int. Cl.
| | |
|---|---|
| C12N 15/00 | (2006.01) |
| C12N 15/62 | (2006.01) |
| C07H 21/00 | (2006.01) |
| A61K 39/00 | (2006.01) |
| C07K 16/30 | (2006.01) |
| G01N 33/574 | (2006.01) |
| C07K 14/705 | (2006.01) |

(52) U.S. Cl.
CPC ........ *A61K 39/0011* (2013.01); *C07K 14/705* (2013.01); *C07K 16/30* (2013.01); *C07K 16/3053* (2013.01); *G01N 33/5743* (2013.01); *G01N 33/57423* (2013.01); *A61K 2039/505* (2013.01); *C07H 21/00* (2013.01); *C07K 2316/96* (2013.01); *C07K 2317/21* (2013.01); *C07K 2317/56* (2013.01); *C07K 2317/622* (2013.01); *C07K 2317/73* (2013.01); *C07K 2317/75* (2013.01); *C07K 2317/76* (2013.01); *C12N 15/00* (2013.01); *C12N 15/62* (2013.01); *G01N 2400/40* (2013.01)

(58) Field of Classification Search
None
See application file for complete search history.

(56) References Cited

U.S. PATENT DOCUMENTS

| | | | |
|---|---|---|---|
| 4,545,985 | A | 10/1985 | Pastan et al. |
| 5,866,124 | A | 2/1999 | Hardman et al. |
| 2004/0105862 | A1 | 6/2004 | Pan et al. |
| 2008/0214791 | A1 | 9/2008 | Ferrone |

FOREIGN PATENT DOCUMENTS

| | | |
|---|---|---|
| WO | WO 00/38515 | 7/2000 |
| WO | WO 2006/100582 | 9/2006 |
| WO | WO 2008/079172 | 7/2008 |

OTHER PUBLICATIONS

Liu et al., "pPIC9-Fc: A Vector System for the Production of Single-Chain Fv-Fc Fusions in *Pichia pastoris* as Detection Reagents *In Vitro,*" *J Biochem* 134:911-917, 2003.
Bendig, "Humanization of Rodent Monoclonal Antibodies by CDR Grafting," *Methods: A Comparison to Methods in Enzymology*, vol. 8:83-93, 1995.
Bonnycastle et al., "Probing the Basis of Antibody Reactivity with a Panel of Constrained Peptide Libraries Displayed by Filamentous Phage," *J. Mol. Biol.*, vol. 258:747-762, 1996.
Campoli et al., "Human High Molecular Weight-Melanoma-Associated Antigen (HMW-MAA): A Melanoma Cell Surface Chondroitin Sulfate Proteoglycan (MSCP) with Biological and Clinical Significance," *Critic. Rev. Immunol.*, vol. 24:267-296, 2004.
Colman, "Effects of Amino Acid Sequence Changes on Antibody-Antigen Interactions," Research in Immunol., vol. 145:33-36, 1994.
Desai et al., "Characterization of Human Anti-High Molecular Weight-Melanoma-Associated Antigen Single-Chain Fv Fragments Isolated from a Phage Display Antibody Library," *Cancer Res.*, vol. 58:2417-2425, 1998.
Drake et al., "Targeting 11q23 Positive Acute Leukemia Cells with High Molecular Weight-Melanoma Associated Antigen-Specific Monoclonal Antibodies," *Cancer Immunol. Immunother.*, vol. 58(3):415-427, 2009.
Goto et al., "Human High Molecular Weight-Melanoma-Associated Antigen: Utility for Detection of Metastatic Melanoma in Sentinel Lymph Nodes," *Clin. Cancer Res.*, vol. 14:3401-3407, 2008.
Hafner et al., "Suppression of Human Melanoma Tumor Growth in SCID Mice by a Human High Molecular Weight-Melanoma Associated Antigen (HMW-MAA) Specific Monoclonal Antibody," *Int. J. Cancer*, vol. 114:426-432, 2005.

(Continued)

*Primary Examiner* — Hong Sang
(74) *Attorney, Agent, or Firm* — Klarquist Sparkman, LLP

(57) ABSTRACT

Disclosed herein are isolated human monoclonal antibodies, and functional fragments thereof, that specifically bind HMW-MAA. Nucleic acids encoding these antibodies, expression vectors including these nucleic acid molecules, and isolated host cells that express the nucleic acid molecules are also disclosed. The antibodies can be used to detect HMW-MAA in a sample. Methods of diagnosing cancer, or confirming a diagnosis of cancer, are disclosed herein that utilize these antibodies. Methods of treating a subject with cancer are also disclosed.

8 Claims, 24 Drawing Sheets

(56) References Cited

OTHER PUBLICATIONS

Kruif et al., "Selection and Application of Human Single Chain Fv Antibody Fragments from a Semi-synthetic Phage Antibody Display Library with Designed CDR3 Regions," *J. Mol. Biol.*, vol. 248:97-105, 1995.
Luo et al., "Differential Immunogenicity of Two Peptides Isolated by High Molecular Weight-Melanoma-Associated Antigen-Specific Monoclonal Antibodies with Different Affinities," *J. Immunol.*, 174:7104-7110, 2005.
Luo et al., "Targeting Melanoma Cells with Human High Molecular Weight-Melanoma Associated Antigen-Specific Antibodies Elicited by a Peptide Mimotope: Functional Effects," *J. Immunol.*, vol. 176:6046-6054, 2006.
Mittelman et al., "Human High Molecular Weight Melanoma-Associated Antigen (HMW-MAA) Mimicry by Mouse Anti-Idiotypic Monoclonal Antibody MK2-23: Induction of Humoral Anti-HMW-MAA Immunity and Prolongation of Survival in Patients with Stave IV Melanoma," *Proc. Natl. Acad. Sci. USA*, vol. 89:466-470, 1992.
Noronha et al., "Limited Diversity of Human scFv Fragments Isolated by Panning a Synthetic Phage-Display scFv Library with Cultured Human Melanoma Cells," *J. Immunol.*, 161:2968-2976, 1998.
Paul, *Fundamental Immunology*, 3rd Ed., Ch. 9, pp. 292-295, 1993.
Riemer et al., "High-Molecular-Weight Melanoma-Associated Antigen Mimotope Immunizations Induce Antibodies Recognizing Melanoma Cells," *Cancer Immunol. Immunother.*, 54:677-684, 2005.
Rudikoff et al., "Single Amino Acid Substitution Altering Antigen-Binding Specificity," *Proc. Natl. Acad. Sci. USA.*, vol. 79:1979-1983, 1982.
Ulmer et al., "Immunomagnetic Enrichment, Genomic Characterization, and Prognostic Impact of Circulating Melanoma Cells," *Clin. Cancer Res.*, vol. 10:531-537, 2004.
Vergilis et al., "Presence and Prognostic Significance of Melanoma-Associated Antigens CYT-MAA and HMW-MAA in Serum of Patients with Melanoma," *J. Invest. Dermatol.*, vol. 125:526-531, 2005.
Wagner et al., "Vaccination with a Human High Molecular Weight Melanoma-Associated Antigen Mimotope Induces a Humoral Response Inhibiting Melanoma Cell Growth In Vitro," *J. Immunol.*, 174:976-982, 2005.
Wagner et al., "Reduction of Human Melanoma Tumor Growth in Severe Combined Immunodeficient Mice by Passive Transfer of Antibodies Induced by a High Molecular Weight Melanoma-Associated Antigen Mimotope Vaccine," *Clin. Cancer Res.*, vol. 14:8178-8183, 2008.
Wang et al., "Immunotherapy of Melanoma: Peptide Mimics of a Human High Molecular Weight-Melanoma Associated Antigen," *Medicina* (Buenos Aires), vol. 60 (Supl. II):48-50, 2000.
Wang et al., "Identification of a Peptide Mimic of the Determinant Recognized by Human SCFV C21," *Immunol. Investigations*, vol. 29(2):205, 2000.
Wang et al., "Human High Molecular Weight Melanoma-Associated Antigen Mimicry by Mouse Anti-Idiotypic Monoclonal Antibody MK2-23: Enhancement of Immunogenicity of Anti-Idiotypic Monoclonal Antibody MK2-23 by Fusion with Interleukin 2," *Cancer Res*, vol. 65(15):6976-6983, 2005.

scFv C21-peptide P1C21 complex

FIG. 14
Surface staining of human melanoma cell lines with scFv-Fc C21
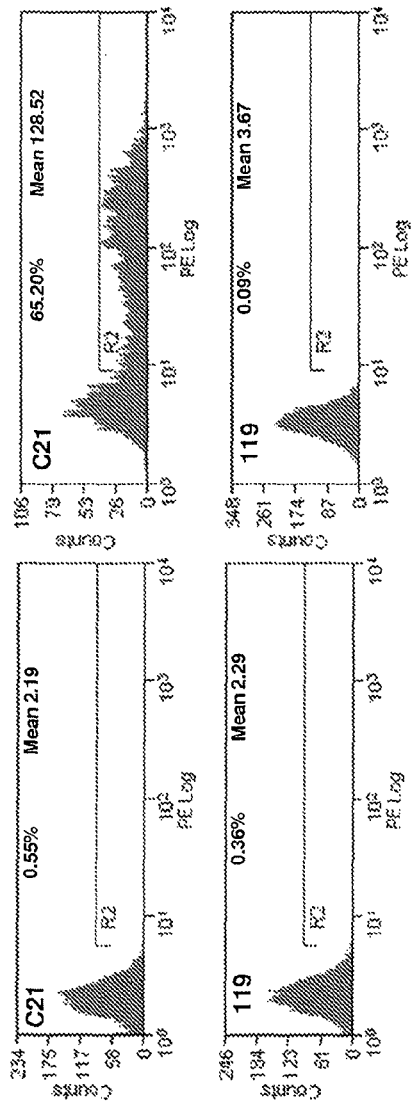
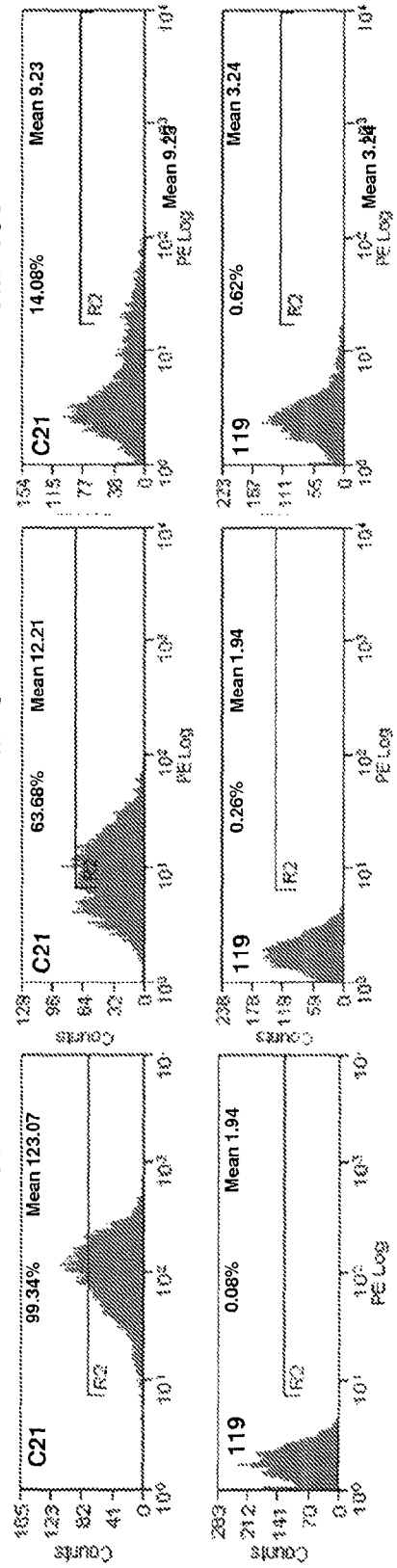

Inhibition of experimental lung metastases of human melanoma cells MV3 by scFv-Fc C21
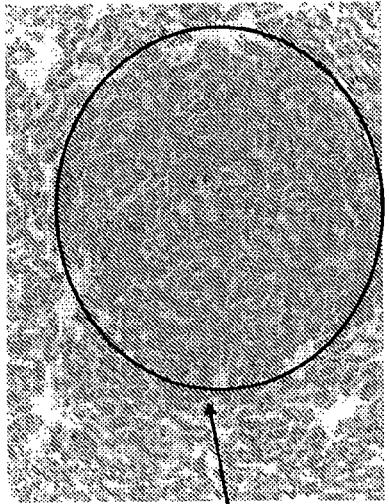
FIG. 16A
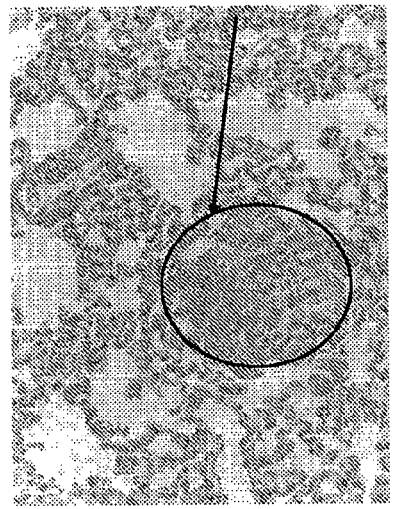
FIG. 16B
Tumor nodules in mouse lungs
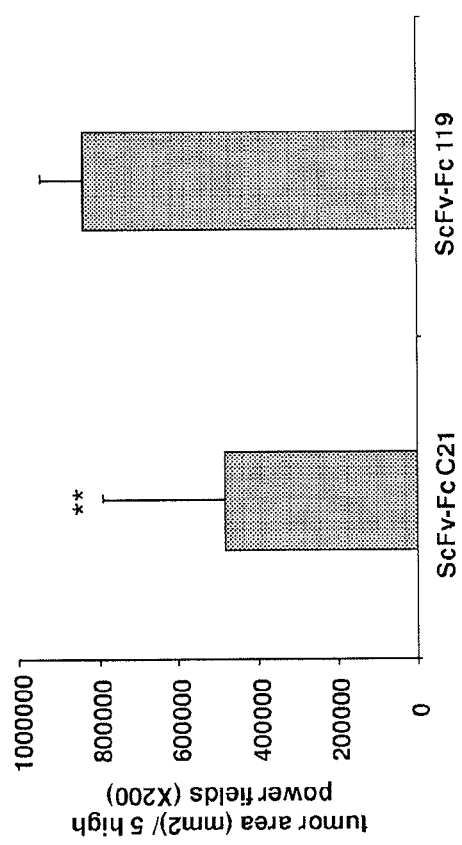
A. ScFv-Fc C21 treated group    B. Control ScFv-Fc 119 treated group scFv-Fc C21 inhibits tumor cell proliferation in *metastatic* lesions in mice
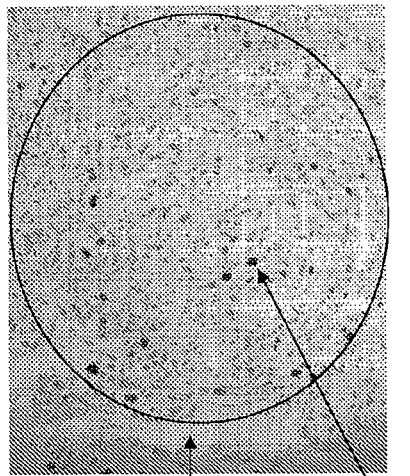
FIG. 17A
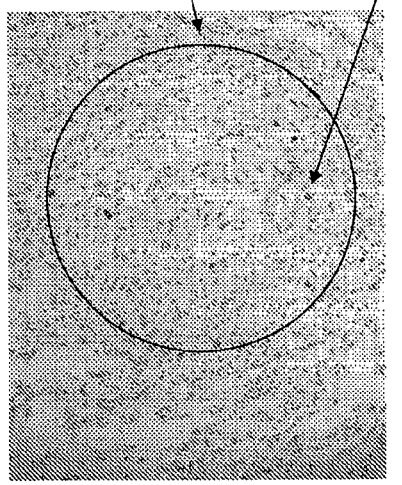
FIG. 17B
Tumor Nodules in mouse lungs
*Brown*-positive for p-HistoneH3 (ser10): indicator of *mitotic cells*
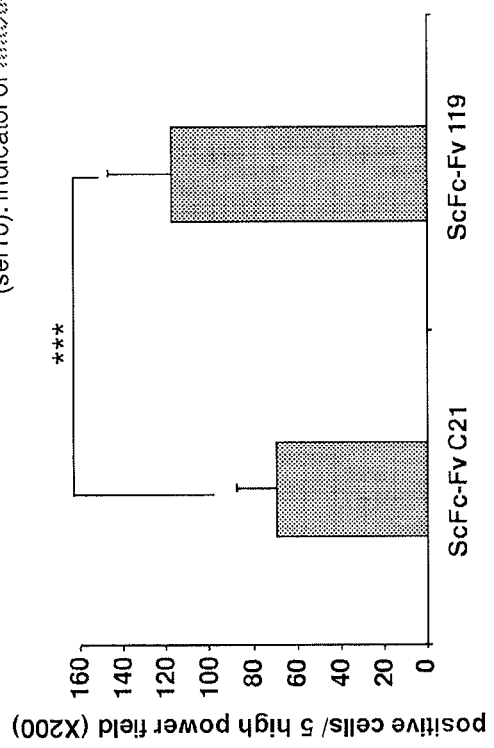
A: ScFv-Fc C21 treated   B: isotype control treated   *** indicates p=0.0005

Inhibition of post surgery spontaneous lung metastasis in mice by scFv-Fc C21

Lung metastasis found in:
1/6 mice treated with C21
6/6 mice treated with 119

Decreased PKC-α and p-Src levels in surgically removed primary MV3 tumor tissues Inhibition of MDA-MB-231 *in vitro* cell growth by scFv-Fc C21

Wnt/β-Catenin

SEQUENCE LISTING

<160> NUMBER OF SEQ ID NOS: 15

<210> SEQ ID NO 1
<211> LENGTH: 356
<212> TYPE: DNA
<213> ORGANISM: Homo sapiens

<400> SEQUENCE: 1

```
atgcaggtgc agctggtgca gtctggggct gaggtgaaga agcctgggtc ctcggtgaag      60
gtctctgcaa ggcttctgga ggcaccttca gcagctatgc tatcagctgg gtgcgacagg     120
cccctggaca agggcttgag tggatgggag ggatcatccc tatctttggt acagcaaact     180
acgcacagaa gttccagggc agagtcacga ttaccgcgga cgaatccacg agcacagcct     240
acatggagct gagcagcctg cgatctgacg acacggccgt gtattactgt gcaagggccc     300
ttgatcctat tacgtttgac tcctggggcc aaggtaccct ggtcaccgtc tcgaga         356
```

<210> SEQ ID NO 2
<211> LENGTH: 45
<212> TYPE: DNA
<213> ORGANISM: Artificial Sequence
<220> FEATURE:
<223> OTHER INFORMATION: Linker

<400> SEQUENCE: 2

```
ggtggaggcg gttcaggcgg aggtggctct ggcggtggcg gatcg                      45
```

<210> SEQ ID NO 3
<211> LENGTH: 330
<212> TYPE: DNA
<213> ORGANISM: Homo sapiens

<400> SEQUENCE: 3

```
tctgagctga ctcaggaccc tgctgtgtct gtggccttgg gacagacagt caggatcaca      60
tgccaaggag acagcctcag aagctattat gcaagctggt accagcagaa gccaggacag     120
gcccctgtac ttgtcatcta tggtaaaaac aaccggccct cagggatccc agaccgattc     180
tctggctcca gctcaggaaa cacagcttcc ttgaccatca ctggggctca ggcggaagat     240
gaggctgact attactgtaa ctcccgggac agcagtggta accatgtggt attcggcgga     300
gggaccaagc tgaccgtcct aggtagatct                                      330
```

<210> SEQ ID NO 4
<211> LENGTH: 699
<212> TYPE: DNA
<213> ORGANISM: Homo sapiens

<400> SEQUENCE: 4

```
gagcccaaat cttgtgacaa aactcacaca tgcccaccgt gcccagcacc tgaactcctg      60
gggggaccgt cagtcttcct cttccccccA aaacccaagg acaccctcat gatctcccgg     120
acccctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa gaccacgcct     540
cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga agagcctctc cctgtctccg ggcaaatga                            699
```

<210> SEQ ID NO 5
<211> LENGTH: 118
<212> TYPE: PRT
<213> ORGANISM: Homo sapiens

<400> SEQUENCE: 5

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95
```

```
Ala Arg Ala Leu Asp Pro Ile Thr Phe Asp Ser Trp Gly Gln Gly Thr
            100                 105                 110

Leu Val Thr Val Ser Arg
        115

<210> SEQ ID NO 6
<211> LENGTH: 110
<212> TYPE: PRT
<213> ORGANISM: Homo sapiens

<400> SEQUENCE: 6

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Val
                85                  90                  95

Val Phe Gly Gly Gly Thr Lys Leu Thr Val Leu Gly Arg Ser
            100                 105                 110

<210> SEQ ID NO 7
<211> LENGTH: 15
<212> TYPE: PRT
<213> ORGANISM: Homo sapiens

<400> SEQUENCE: 7

Ser Pro Ser Trp Tyr Cys Pro Asp Cys Asp Lys Arg Pro Leu Val
1               5                   10                  15

<210> SEQ ID NO 8
<211> LENGTH: 15
<212> TYPE: PRT
<213> ORGANISM: Homo sapiens

<400> SEQUENCE: 8

Glu Ala Arg Asn Trp His Asp Phe Pro Ile His Pro Arg Thr Leu
1               5                   10                  15

<210> SEQ ID NO 9
<211> LENGTH: 9
<212> TYPE: PRT
<213> ORGANISM: Homo sapiens
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 9

Pro Xaa Xaa Tyr Xaa Pro Xaa Xaa Asp
1               5
```

<210> SEQ ID NO 10
<211> LENGTH: 15
<212> TYPE: PRT
<213> ORGANISM: Homo sapiens

<400> SEQUENCE: 10

Arg Pro Tyr Arg Tyr Asp Pro Leu Gly Asp Leu Lys Ser Arg His
1               5                   10                  15

<210> SEQ ID NO 11
<211> LENGTH: 15
<212> TYPE: PRT
<213> ORGANISM: Homo sapiens

<400> SEQUENCE: 11

Arg Pro Tyr Arg Ala Asp Pro Leu Gly Asp Leu Lys Ser Arg His
1               5                   10                  15

<210> SEQ ID NO 12
<211> LENGTH: 15
<212> TYPE: PRT
<213> ORGANISM: Homo sapiens

<400> SEQUENCE: 12

Arg Pro Tyr Arg Tyr Asp Val Leu Gly Asp Leu Lys Ser Arg His
1               5                   10                  15

<210> SEQ ID NO 13
<211> LENGTH: 15
<212> TYPE: PRT
<213> ORGANISM: Homo sapiens

<400> SEQUENCE: 13

Arg Pro Tyr Arg Tyr Asp Pro Leu Gly Ser Leu Lys Ser Arg His
1               5                   10                  15

<210> SEQ ID NO 14
<211> LENGTH: 327
<212> TYPE: PRT
<213> ORGANISM: Homo sapiens

<400> SEQUENCE: 14

Glu Gln Met Arg Glu Glu Pro Glu Ala Ala Tyr Arg Leu Ile Gln Gly
1               5                   10                  15

Pro Gln Tyr Gly His Leu Leu Val Gly Gly Arg Pro Thr Ser Ala Phe
                20                  25                  30

Ser Gln Phe Gln Ile Asp Gln Gly Glu Val Val Phe Ala Phe Thr Asn
            35                  40                  45

Phe Ser Ser Ser His Asp His Phe Arg Val Leu Ala Leu Ala Arg Gly
        50                  55                  60

Val Asn Ala Ser Ala Val Val Asn Val Thr Val Arg Ala Leu Leu His
65                  70                  75                  80

Val Trp Ala Gly Gly Pro Trp Pro Gln Gly Ala Thr Leu Arg Leu Asp
                85                  90                  95

Pro Thr Val Leu Asp Ala Gly Glu Leu Ala Asn Arg Thr Gly Ser Val
                100                 105                 110

Pro Arg Phe Arg Leu Leu Glu Gly Pro Arg His Gly Arg Val Val Arg
            115                 120                 125

Val Pro Arg Ala Arg Thr Glu Pro Gly Gly Ser Gln Leu Val Glu Gln
        130                 135                 140

```
Phe Thr Gln Gln Asp Leu Glu Asp Gly Arg Leu Gly Leu Glu Val Gly
145                 150                 155                 160

Arg Pro Glu Gly Arg Ala Pro Gly Pro Ala Gly Asp Ser Leu Thr Leu
            165                 170                 175

Glu Leu Trp Ala Gln Gly Val Pro Pro Ala Val Ala Ser Leu Asp Phe
        180                 185                 190

Ala Thr Glu Pro Tyr Asn Ala Ala Arg Pro Tyr Ser Val Ala Leu Leu
    195                 200                 205

Ser Val Pro Glu Ala Ala Arg Thr Glu Ala Gly Lys Pro Glu Ser Ser
210                 215                 220

Thr Pro Thr Gly Glu Pro Gly Pro Met Ala Ser Ser Pro Glu Pro Ala
225                 230                 235                 240

Val Ala Lys Gly Gly Phe Leu Ser Phe Leu Glu Ala Asn Met Phe Ser
            245                 250                 255

Val Ile Ile Pro Met Cys Leu Val Leu Leu Leu Ala Leu Ile Leu
        260                 265                 270

Pro Leu Leu Phe Tyr Leu Arg Lys Arg Asn Lys Thr Gly Lys His Asp
    275                 280                 285

Val Gln Val Leu Thr Ala Lys Pro Arg Asn Gly Leu Ala Gly Asp Thr
    290                 295                 300

Glu Thr Phe Arg Lys Val Glu Pro Gly Gln Ala Ile Pro Leu Thr Ala
305                 310                 315                 320

Val Pro Gly Gln Leu Phe Pro
                325

<210> SEQ ID NO 15
<211> LENGTH: 983
<212> TYPE: DNA
<213> ORGANISM: Homo sapiens

<400> SEQUENCE: 15
gggagcagat gagggaggag ccagaggcag cataccgcct catccaggga ccccagtatg        60
ggcatctcct ggtgggcggg cggcccacct cggccttcag ccaattccag atagaccagg      120
gcgaggtggt ctttgccttc accaacttct cctcctctca tgaccacttc agagtcctgg      180
cactggctag ggtgtcaat gcatcagccg tagtgaacgt cactgtgagg gctctgctgc      240
atgtgtgggc agtgggcca tggccccagg gtgccaccct gcgcctggac cccaccgtcc      300
tagatgctgg cgagctggcc aaccgcacag gcagtgtgcc gcgcttccgc ctcctggagg      360 gacccccggca tggccgcgtg gtccgcgtgc cccgagccag gacggagccc ggggggcagcc      420 agctggtgga gcagttcact cagcaggacc ttgaggacgg gaggctgggg ctggaggtgg      480
gcaggccaga ggggagggcc cccggccccg caggtgacga tctcactctg gagctgtggg      540
cacagggcgt cccgcctgct gtggcctccc tggactttgc cactgagcct acaatgctg      600 cccggcccta cagcgtggcc ctgctcagtg tccccgaggc cgcccggacg gaagcaggga      660
agccagagag cagcacccc acaggcgagc caggcccat ggcatccagc cctgagcccg      720
ctgtggccaa gggaggcttc ctgagcttcc ttgaggccaa catgttcagc gtcatcatcc      780
ccatgtgcct ggtacttctg ctcctggcgc tcatcctgcc cctgctcttc tacctccgaa      840
aacgcaacaa gacgggcaag catgacgtcc aggtcctgac tgccaagccc cgcaacggcc      900
tggctggtga caccgagacc tttcgcaagg tggagccagg ccaggccatc ccgctcacag      960
ctgtgcctgg ccagttattt cca                                              983
```

FULLY HUMAN ANTIBODIES TO HIGH MOLECULAR WEIGHT-MELANOMA ASSOCIATED ANTIGEN AND USES THEREOF

CROSS REFERENCE TO RELATED APPLICATIONS

This is a divisional of U.S. application Ser. No. 13/912,429, filed Jun. 7, 2013, which is a divisional of U.S. application Ser. No. 13/123,489, filed Apr. 8, 2011, issued as U.S. Pat. No. 8,476,410 on Jul. 2, 2013, which is the U.S. National Stage of International Application No. PCT/US2009/060903, filed Oct. 15, 2009, published in English under PCT Article 21(2), which claims the benefit of U.S. Provisional Application No. 61/106,055, filed Oct. 16, 2008. The above-listed applications are incorporated herein by reference in their entirety.

ACKNOWLEDGMENT OF GOVERNMENT SUPPORT

This invention was made with government support under contract numbers CA16056 and CA105500, awarded by the National Cancer Institute of the National Institutes of Health. The government has certain rights in the invention.

FIELD

This disclosure concerns fully human monoclonal antibodies, particularly human monoclonal antibodies that specifically bind high molecular weight-melanoma associated antigen (HMW-MAA), and their use.

BACKGROUND

Melanomas are aggressive, frequently metastatic tumors derived from either melanocytes or melanocyte related nevus cells ("Cellular and Molecular Immunology" (1991) (eds.) Abbas A. K., Lechtiman, A. H., Pober, J. S.; W. B. Saunders Company, Philadelphia: pages 340-341). Melanomas make up approximately three percent of all skin cancers and the worldwide increase in melanoma is unsurpassed by any other neoplasm with the exception of lung cancer in women ("Cellular and Molecular Immunology" (1991) (eds.) Abbas, A. K., Lechtiman, A. H., Pober, J. S.; W. B. Saunders Company Philadelphia pages: 340-342; Kirkwood and Agarwala (1993) *Principles and Practice of Oncology* 7:1-16). Even when melanoma is apparently localized to the skin, up to 30% of the patients will develop systemic metastasis and the majority will die (Kirkwood and Agarwala (1993) *Principles and Practice of Oncology* 7:1-16). Classic modalities of treating melanoma include surgery, radiation and chemotherapy. In the past decade, immunotherapy and gene therapy have emerged as new and promising methods for treating melanoma.

Strong evidence that an immune response to cancer exists in humans is provided by the existence of lymphocytes within melanoma deposits. These lymphocytes, when isolated, are capable of recognizing specific tumor antigens on autologous and allogeneic melanomas in a major histocompatibility complex (MHC)-restricted fashion (Itoh et al. (1986), *Cancer Res.* 46: 3011-3017; Muul et al. (1987), *J. Immunol.* 138:989-995); Topalian et al. (1989) *J. Immunol.* 142: 3714-3725; Darrow et al. (1989) *J. Immunol.* 142: 3329-3335; Hom et al. (1991) *J. Immunother.* 10:153-164; Kawakami et al. (1992) *J. Immunol.* 148: 638-643; Hom et al. (1993) *J. Immunother.* 13:18-30; O'Neil et al. (1993) *J. Immunol.* 151: 1410-1418). Tumor infiltrating lymphocytes (TIL) from patients with metastatic melanoma recognize shared antigens including melanocyte-melanoma lineage specific tissue antigens in vitro (Kawakami et al. (1993) *J. Immunother.* 14: 88-93; Anichini et al. (1993) *J. Exp. Med.* 177: 989-998). Anti-melanoma T cells appear to be enriched in TIL probably as a consequence of clonal expansion and accumulation at the tumor site in vivo (Sensi et al. (1993) *J. Exp. Med.* 178:1231-1246). The fact that many melanoma patients mount cellular and humoral responses against these tumors and that melanomas express both MHC antigens and tumor associated antigens (TAA) suggests that identification and characterization of additional melanoma antigens will be important for immunotherapy of patients with melanoma.

The human chondroitin sulfate proteoglycan HMW-MAA, also know as CSPG4, is an early cell surface melanoma progression marker implicated in stimulating tumor cell proliferation, migration and invasion. Clinical studies have indicated HMW-MAA as a relevant therapeutic target because a vaccine targeting HMW-MAA in patients with melanoma immunized with HMW-MAA mimics provides significant survival advantage only to a subset of patients who developed HMW-MAA-specific antibodies, but not to those patients who did not develop them. In addition, the biologic significance of targeting HMW-MAA could be related to the role in regulating cell growth and differentiation. However, a need remains for other immunotherapeutic strategies that target this antigen.

SUMMARY

Provided herein are fully human monoclonal antibodies that specifically bind HMW-MAA. Functional fragments of fully human monoclonal antibodies are also provided. In some embodiments, the human monoclonal antibodies are single chain variable fragments (scFv). Further provided are compositions including the HMW-MAA-specific antibodies and functional fragments thereof, nucleic acids encoding these antibodies, expression vectors comprising the nucleic acids, and isolated host cells that express the nucleic acids.

Also provided are immunoconjugates comprising the human monoclonal antibodies that specifically bind HMW-MAA. Compositions comprising the immunoconjugates are also provided.

The antibodies and compositions provided herein can be used for a variety of purposes, such as for confirming the diagnosis of cancer in a subject. Thus, provided herein is a method of confirming the diagnosis of cancer in a subject, that includes contacting a sample from the subject diagnosed with cancer with a human monoclonal antibody that specifically binds HMW-MAA, and detecting binding of the antibody to the sample. An increase in binding of the antibody to the sample relative to binding of the antibody to a control sample confirms the cancer diagnosis. In some embodiments, the method further comprises contacting a second antibody that specifically recognizes the HMW-MAA-specific antibody with the sample, and detecting binding of the second antibody.

Similarly, provided herein is a method of detecting cancer in a subject that includes contacting a sample from the subject with a human monoclonal antibody described herein, and detecting binding of the antibody to the sample. An increase in binding of the antibody to the sample relative to a control sample detects cancer in the subject. In some embodiments, the methods further comprise contacting a second antibody that specifically recognizes the HMW- MAA-specific antibody with the sample, and detecting binding of the second antibody.

Further provided is a method of treating a subject diagnosed with cancer, that includes administering to the subject a therapeutically effective amount of a HMW-MAA-specific monoclonal antibody, a functional fragment thereof, or an immunoconjugate comprising the antibody or functional fragment thereof. In some examples, the cancer is a melanoma, a head and neck cancer or a glioma.

Also provided are HMW-MAA peptide mimics. The peptide mimics disclosed herein bind a human monoclonal antibody specific for HMW-MAA. In some embodiments, the peptide mimics comprise the consensus sequence PXXYXPXXD (SEQ ID NO: 9).

The foregoing and other objects, features, and advantages of the invention will become more apparent from the following detailed description, which proceeds with reference to the accompanying figures.

BRIEF DESCRIPTION OF THE FIGURES

FIG. 14. Flow analysis showing surface staining of human melanoma cell lines with scFv-Fc C21.

FIGS. 16A and 16B. Digital images and graph showing the inhibition of experimental lung metastases of human melanoma cells MV3 by scFv-Fc C21. The protocol was as follows: Day 0: inject MV3 cells 1.4×10$^6$/mouse i.v.; Day 3: Starting mAb therapy, 100 µg/mouse, i.v. twice per week; Day 27: Sacrifice mice and collect lung-formalin fixed and paraffin embedded and H&E stained for the following analysis: Taking pictures of randomly selected 5 high power fields (×200) of each section and then measure the tumor area using the SPOT software. The values shown are the mean tumor area of each group. ** indicates p value <0.01.

FIGS. 17A and 17B. Digital images and graph showing scFv-Fc C21 inhibits tumor cell proliferation in metastatic lesions in mice. The protocol was as follows: Day 0: inject MV3 cells 1.4×10$^6$/per mouse i.v.; Day 3: starting antibody therapy, 100 g/per mouse, i.v. twice per week; Day 27: sacrifice mice and collect lung-formalin fixed and paraffin embedded.

SEQUENCE LISTING

Figure 1:
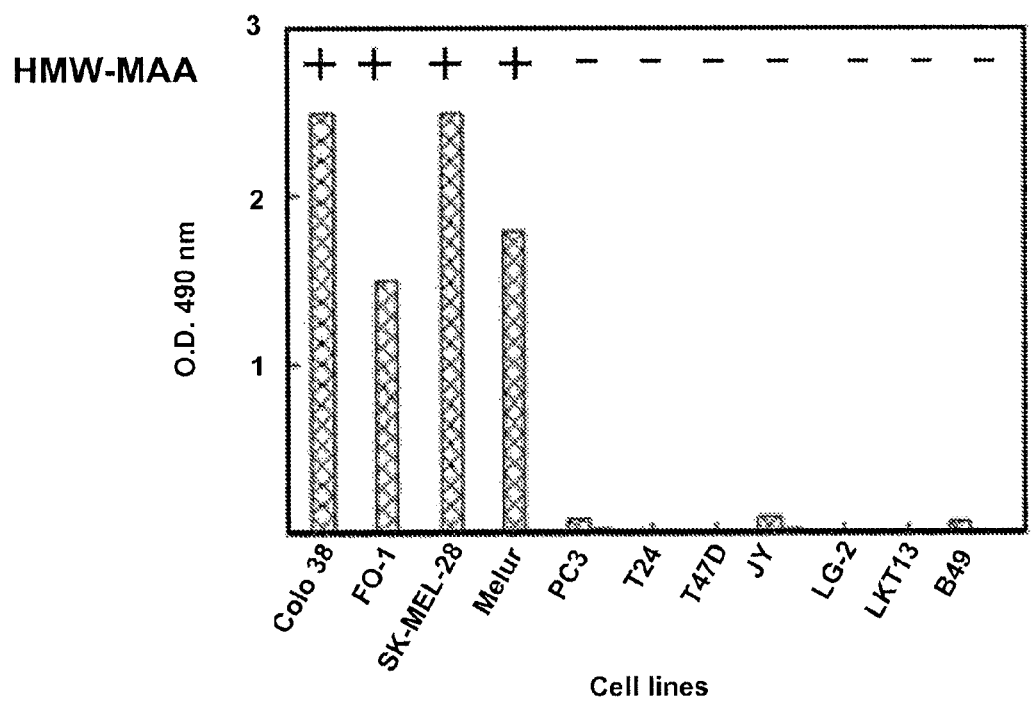
FIG. 1. Selective reactivity in ELISA of soluble scFv C21 with HMW-MAA+ human cell lines. Cultured human melanoma cells Colo38, FO-1, SK-MEL-28 and Melur, all of which express HMW-MAA, and human prostate carcinoma cells PC3, human bladder carcinoma cells T24, human breast carcinoma cells T47D and human B lymphoid cells JY, LG-2 and LKT13, all of which do not express HMW-MAA and rat neuroblastoma cells B49, which express a HMW-MAA homolog were incubated at 4° C. for 2 h with 50 µl of SNT scFv C21 (▨) and with biotinylated mAb 9E10 (2.5 µg/ml 1% BSA-PBS). Binding of scFv fragments was detected using SA-HRP. Results are expressed as absorbance at 490 nm. Human anti-anti-id scFv #119 (■) was used as a specificity control.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Oct. 8, 2015, 10.4 KB, which is incorporated by reference herein. In the accompanying sequence listing:

SEQ ID NO: 1 is the nucleotide sequence of the $V_H$ domain of scFv C21.

SEQ ID NO: 2 is the nucleotide sequence of the scFv C21 linker.

SEQ ID NO: 3 is the nucleotide sequence of the $V_L$ domain of scFv C21.

SEQ ID NO: 4 is the nucleotide sequence of an immunoglobulin heavy chain including the hinge, CH2 and CH3 domains.

SEQ ID NO: 5 is the amino acid sequence of the $V_H$ domain of scFv C21.

SEQ ID NO: 6 is the amino acid sequence of the $V_L$ domain of scFv C21.

SEQ ID NO: 7 is the amino acid sequence of peptide P1C21.

SEQ ID NO: 8 is the amino acid sequence of peptide P2C21.

SEQ ID NO: 9 is the amino acid consensus sequence of peptides that bind scFv C21.

SEQ ID NO: 10 is the amino acid sequence of peptide P3C21.

SEQ ID NO: 11 is the amino acid sequence of peptide P3A5.

SEQ ID NO: 12 is the amino acid sequence of peptide P3V7.

SEQ ID NO: 13 is the amino acid sequence of peptide P3S10.

SEQ ID NO: 14 is the amino acid sequence of HMW-MAA

SEQ ID NO: 15 is an exemplary nucleic acid sequence encoding HMW-MAA.

SEQ ID NO: 16 is the amino acid sequence of a MART-1 peptide.

DETAILED DESCRIPTION

Because of its high expression on melanoma cells with limited intra- and inter-lesional heterogeneity in a large percentage of patients with melanoma, and its restricted distribution in normal tissues (Ferrone et al., *Radiolabeled Monoclonal Antibodies for Imaging and Therapy* 152:55, 1988), the human chondroitin sulfate proteoglycan HMW-MAA represents an attractive target to implement immunotherapy of melanoma (Spitler et al., *Cancer Res* 47:1717-1723, 1987; Mittelman et al., *J Clin Invest* 86:2136-2144, 1990; Quan et al., *J Clin Oncol* 15:2103-2110, 1997). Like most of the identified human tumor antigens, HMW-MAA is a self antigen. As a result, it is poorly immunogenic in patients with melanoma (Hamby et al., *Cancer Res* 47:5284-5289, 1997). To overcome this limitation, which hinders the application of HMW-MAA as an immunogen in patients with melanoma, mouse anti-idiotypic (anti-id) monoclonal antibodies (mAb), which mimic HMW-MAA determinants defined by mouse mAb, have been used to implement active specific immunotherapy in clinical trials (Mittelman et al., *J Clin Invest* 86:2136-2144, 1990; Quan et al., *J Clin Oncol* 15:2103-2110, 1997; Mittelman et al., *Proc Natl Acad Sci USA* 89:466-470, 1992; Pride et al., *Clin Cancer Res* 4:2363-2370, 1998). HMW-MAA mimics have been found to induce HMW-MAA specific humoral immunity in about 60% of the immunized patients (Mittelman et al., *Proc Natl Acad Sci USA* 89:466-470, 1992). The association of this immunity with regression of metastases in a few patients (Mittelman et al., *Cancer Res* 54:415-421, 1994) and with a statistically significant survival prolongation (Mittelman et al., *Proc Natl Acad Sci USA* 89:466-470, 1992) has stimulated interest in optimizing the immunization strategy with HMW-MAA mimics.

Thus far, the characterization of the antigenic profile of HMW-MAA and the development of mimics have been restricted to determinants recognized by mouse mAb. Through the use of a large panel of mouse mAb, six distinct and spatially distant antigenic determinants have been identified on HMW-MAA (Campoli et al., *Crit Rev Immunol* 24:267-296, 2004). In addition, mimics of the antigenic determinants defined by mouse mAb have been developed and characterized in their immunogenicity (Luo et al., *J Immunol* 174:7104-7110, 2005). In contrast, only a limited number of HMW-MAA-specific human scFv antibodies have been isolated from phage display scFv antibody libraries and shown to recognize antigenic determinants distinct from those defined by mouse mAb (Desai et al., *Cancer Res* 58:2417-2425, 1998; Noronha et al., *J Immunol* 161:2968-2976, 1998).

Furthermore, no mimics of the antigenic determinants identified by HMW-MAA-specific human antibodies have been isolated and analyzed for their immunogenic properties. The lack of this information, which may reflect the low association constants of the available HMW-MAA-specific human scFv antibodies (Desai et al., *Cancer Res* 58:2417-2425, 1998; Noronha et al., *J Immunol* 161:2968-2976, 1998), has a negative impact on the optimization of immunization strategies with HMW-MAA mimics.

Thus, disclosed herein is a HMW-MAA-specific scFv (C21) isolated from a semi-synthetic phage display scFv antibody library which is more reflective of the human immune repertoire and is a source of scFv antibodies with a higher affinity than those previously described. Antibodies including one or more CDRs from this human monoclonal antibody that specifically bind HMW-MAA are also disclosed. Moreover, the fine specificity of scFv C21 is defined and utilized to isolate HMW-MAA peptide mimics from a phage display peptide library. These peptide bind a human monoclonal antibody specific for HMW-MAA. In some embodiments, the peptide mimics comprise the consensus sequence PXXYXPXXD (SEQ ID NO: 9).

I. Abbreviations

CDR Complementarity determining region
CT Commuted tomography
DMSO Dimethyl sulfoxide
DTH Delayed type hypersensitivity
EDC N-ethyl-N'-(dimethylaminopropyl) carbodiimide
ELISA Enzyme-linked immunosorbent assay
FBS Fetal bovine serum
HMW-MAA High molecular weight melanoma associated antigen
HNSCC Head and neck squamous cell carcinoma
HPLC High pressure liquid chromatography
IPTG Isopropyl-β-D-thiogalactopyranoside
KLH Keyhole limpet haemocyanin
mAb Monoclonal antibody
MBS Maleimidobenzoyl-N-hydroxysuccinimide
MRI Magnetic resonance imaging
NHS N-hydroxysuccinimide
OD Optical density
PAGE Polyacrylamide gel electrophoresis
PBS Phosphate-buffered saline
PET Positron emission tomography
PP Periplasmic preparation
s.c. Subcutaneous
scFv Single chain fragment variable
SDS Sodium dodecyl sulfate
SNT Supernatant
SPR Surface plasmon resonance II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and specifically binds an epitope of an antigen, such as HMW-MAA, or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds HMW-MAA will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds HMW-MAA.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. An antibody that "specifically binds" an antigen, such as HMW-MAA with a high affinity and does not significantly bind other unrelated antigens.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a lymphoma, leukemia, or another tumor. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds HMW-MAA or a fragment thereof used in combination with a radioactive or chemical compound.

Chimeric antibody: An antibody that includes sequences derived from two different antibodies, which typically are of different species. Most typically, chimeric antibodies include human and murine antibody domains, generally human constant regions and murine variable regions, murine CDRs and/or murine SDRs.

Conservative variants: "Conservative" amino acid substitutions are those substitutions that do not substantially affect or decrease the affinity of an antibody to HMW-MAA. For example, a human antibody that specifically binds HMW-MAA can include at most about 1, at most about 2, at most about 5, and most about 10, or at most about 15 conservative substitutions and specifically bind the original HMW-MAA polypeptide. The term conservative variation also includes the use of a substituted amino acid in place of an unsubstituted parent amino acid, provided that antibody specifically binds HMW-MAA. Non-conservative substitutions are those that reduce an activity or binding to HMW-MAA.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: A polynucleotide encoding a HMW-MAA polypeptide or an antibody that binds HMW-MAA that includes a sequence that is degenerate as a result of the genetic code. There are 20 natural amino acids, most of which are specified by more than one codon. Therefore, all degenerate nucleotide sequences are included as long as the amino acid sequence of the HMW-MAA polypeptide or antibody that binds HMW-MAA encoded by the nucleotide sequence is unchanged.

Diagnostic: Identifying the presence or nature of a pathologic condition, such as, but not limited to, melanoma, breast cancer, glioma, head and neck cancer or prostate cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as breast cancer or metastasis.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses.

Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-HMW-MAA antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., Pharm. Ther. 28:341-365, 1985). Diagnostic agents or moieties include radioisotopes and other detectable labels. Detectable labels useful for such purposes are also well known in the art, and include radioactive isotopes such as $^{35}$S, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as HMW-MAA.

Expressed: Translation of a nucleic acid into a protein. Proteins may be expressed and remain intracellular, become a component of the cell surface membrane, or be secreted into the extracellular matrix or medium.

Framework region: Amino acid sequences interposed between CDRs. Framework regions include variable light and variable heavy framework regions. The framework regions serve to hold the CDRs in an appropriate orientation for antigen binding.

Glioma: A tumor composed of neuroglia in any developmental state. Gliomas include all intrinsic neoplasms of the brain and spinal cord, such as astrocytomas, ependymomas, and oligodendrogliomas. "Low-grade" gliomas are well-differentiated (not anaplastic); these are benign and portend a better prognosis for the patient. "High-grade" gliomas are undifferentiated or anaplastic; these are malignant and carry a worse prognosis.

HAMA (human anti-murine antibody) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Host cells: Cells in which a vector can be propagated and its DNA expressed. The cell may be prokaryotic or eukaryotic. The term also includes any progeny of the subject host cell.

It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunoconjugate: A covalent linkage of an effector molecule to an antibody or functional fragment thereof. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunogenic peptide: A peptide which comprises an allele-specific motif or other sequence, such as an N-terminal repeat, such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one specific non-limiting example, an immunogenic polypeptide includes a region of HMW-MAA, or a fragment thereof, wherein the polypeptide that is expressed on the cell surface of a host cell that expresses the full-length HMW-MAA polypeptide.

Immunogenic composition: A composition comprising a polypeptide, such as a HMW-MAA polypeptide, that induces a measurable CTL response against cells expressing HMW-MAA polypeptide, or induces a measurable B cell response (such as production of antibodies) against a HMW-MAA polypeptide. An immunogenic composition can also induce cytokine production. It further refers to isolated nucleic acids encoding a HMW-MAA polypeptide that can be used to express the HMW-MAA polypeptide (and thus be used to elicit an immune response against this polypeptide). For in vitro use, an immunogenic composition may consist of the isolated protein or peptide epitope. For in vivo use, the immunogenic composition will typically comprise the protein or immunogenic peptide in pharmaceutically acceptable carriers, and/or other agents. Any particular peptide, such as a HMW-MAA polypeptide, or nucleic acid encoding the polypeptide, can be readily tested for its ability to induce a CTL or B cell response by art-recognized assays. Immunogenic compositions can include adjuvants, which are well known to one of skill in the art.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, and pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Major histocompatibility complex (MHC): Generic designation meant to encompass the histocompatibility antigen systems described in different species, including the human leukocyte antigens ("HLA"). The term "motif" refers to the pattern of residues in a peptide of defined length, usually about 8 to about 11 amino acids, which is recognized by a particular MHC allele. The peptide motifs are typically different for each MHC allele and differ in the pattern of the highly conserved residues and negative binding residues.

Melanoma: A form of cancer that originates in melanocytes (cells that make the pigment melanin). Melanocytes are found primary in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism) which is a marker of aggressive behavior and a tendency to local recurrence. Other melanomas include clear cell sarcoma, mucosal melanoma and uveal melanoma.

Features that affect prognosis are tumor thickness in millimeters (Breslow's depth), depth related to skin structures (Clark level), type of melanoma, presence of ulceration, presence of lymphatic/perineural invasion, presence of tumor infiltrating lymphocytes (if present, prognosis is better), location of lesion, presence of satellite lesions, and presence of regional or distant metastasis. When melanomas have spread to the lymph nodes, one of the most important factors is the number of nodes with malignancy. The extent of malignancy within a node is also important; micrometastases in which malignancy is only microscopic have a more favorable prognosis than macrometastases. When there is distant metastasis, the five year survival rate is less than 10 percent; the median survival is 6 to 12 months. Metastases to skin and lungs have a better prognosis. Metastases to brain, bone and liver are associated with a worse prognosis.

Melanoma can be staged as follows:
Stage 0: Melanoma in Situ (Clark Level I), 100% Survival
Stage I/II: Invasive Melanoma, 85-95% Survival
  T1a: Less than 1.00 mm primary, w/o Ulceration, Clark Level II-III
  T1b: Less than 1.00 mm primary, w/Ulceration or Clark Level IV-V
  T2a: 1.00-2.00 mm primary, w/o Ulceration
Stage II: High Risk Melanoma, 40-85% Survival
  T2b: 1.00-2.00 mm primary, w/ Ulceration
  T3a: 2.00-4.00 mm primary, w/o Ulceration
  T3b: 2.00-4.00 mm primary, w/ Ulceration
  T4a: 4.00 mm or greater primary w/o Ulceration
  T4b: 4.00 mm or greater primary w/ Ulceration
Stage III: Regional Metastasis, 25-60% Survival
  N1: Single Positive Lymph Node
  N2: 2-3 Positive Lymph Nodes OR Regional Skin/In-Transit Metastasis
  N3: 4 Positive Lymph Nodes OR Lymph Node and Regional Skin/In Transit Metastases
Stage IV: Distant Metastasis, 9-15% Survival
  M1a: Distant Skin Metastasis, Normal lactate dehydrogenase (LDH)
  M1b: Lung Metastasis, Normal LDH
  M1c: Other Distant Metastasis OR Any Distant Metastasis with Elevated LDH Monoclonal antibody: An antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized and fully human monoclonal antibodies. As used herein a monoclonal antibody includes antibody fragments, such as, but not limited to scFv, Fv, dsRv, or Fab.

Neoplasia, malignancy, cancer or tumor: The result of abnormal and uncontrolled growth of cells. Neoplasia, malignancy, cancer and tumor are often used interchangeably. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples, a tumor is melanoma, breast cancer, prostate cancer, glioma or a squamous cell carcinoma, such as head and neck cancer.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (world wide web ncbi.nlm.nih.gov/). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Oligonucleotide: A linear polynucleotide sequence of up to about 100 nucleotide bases in length.

Open reading frame (ORF): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (such as glycosylation or phosphorylation). In one embodiment, the polypeptide is HMW-MAA polypeptide. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Probes and primers: A probe comprises an isolated nucleic acid attached to a detectable label or reporter molecule. Primers are short nucleic acids, preferably DNA oligonucleotides, 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers can be selected that comprise 20, 25, 30, 35, 40, 50 or more consecutive nucleotides.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (such as the metallothionein promoter) or from mammalian viruses (such as the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Prostate cancer: A type of cancer that forms in tissues of the prostate, a gland in the male reproductive system. Prostate cancer is classified as an adenocarcinoma, or glandular cancer, that begins when normal semen-secreting prostate gland cells mutate into cancer cells. The region of prostate gland where the adenocarcinoma is most common is the peripheral zone. Initially, small clumps of cancer cells remain confined to otherwise normal prostate glands, a condition known as carcinoma in situ or prostatic intraepithelial neoplasia (PIN). Although there is no proof that PIN is a cancer precursor, it is closely associated with cancer. Over time these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer is considered a malignant tumor because it is a mass of cells which can invade other parts of the body. Prostate cancer most commonly metastasizes to the bones, lymph nodes, rectum and bladder.

Prostate cancer can be staged as follows:
Stage 0: No evidence of tumor
Stage I: Tumor present, but not detectable clinically or with imaging
  T1a: Tumor was incidentally found in less than 5% of prostate tissue resected
  T1b: Tumor was incidentally found in greater than 5% of prostate tissue resected
  T1c: Tumor was found in a needle biopsy performed due to an elevated serum prostate specific antigen (PSA)
Stage II: The tumor can be felt (palpated) on examination, but has not spread outside the prostate
  T2a: The tumor is in half or less than half of one of the prostate gland's two lobes
  T2b: The tumor is in more than half of one lobe, but not both
  T2c: The tumor is in both lobes
Stage III: The tumor has spread through the prostatic capsule
  T3a: The tumor has spread through the capsule on one or both sides
  T3b: the tumor has invaded one or both seminal vesicles
Stage IV: The tumor has invaded other nearby structures Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation.

The HMW-MAA polypeptides disclosed herein, or antibodies that specifically bind HMW-MAA, can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Recombinant toxins: Chimeric proteins in which a cell targeting moiety is fused to a toxin (Pastan et al., *Science*, 254:1173-1177, 1991). If the cell targeting moiety is the Fv portion of an antibody, the molecule is termed a recombinant immunotoxin (Chaudhary et al., *Nature*, 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, a cancer in which HMW-MAA is expressed.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, Gene 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a HMW-MAA polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a HMW-MAA specific binding agent is an agent that binds substantially to a HMW-MAA polypeptide. An HMW-MAA specific binding agent does not bind substantially to other unrelated proteins. In one embodiment, the specific binding agent is a human monoclonal antibody that specifically binds the HMW-MAA polypeptide.

The term "specifically binds" refers, with respect to an antigen such as HMW-MAA, to the preferential association of an antibody or other ligand, in whole or part, with a cell or tissue bearing that antigen and not to cells or tissues lacking that antigen. It is recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the HMW-MAA polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Squamous cell carcinoma: A type of cancer that originates in squamous cells, thin, flat cells that form the surface of the skin, eyes, various internal organs, and the lining of hollow organs and ducts of some glands. Squamous cell carcinoma is also referred to as epidermoid carcinoma. One type of squamous cell carcinoma is head and neck head squamous cell carcinoma (HNSCC). Head and neck squamous cell carcinoma includes cancers of the nasal cavity, sinuses, lips, mouth, salivary glands, throat and larynx.

HNSCC can be staged as follows:

Stage 0: No evidence of tumor.

Stage I: Tumor is 2 cm or less in greatest dimension; no evidence of regional lymph node involvement or distant metastasis.

Stage II: Tumor is more than 2 cm, but no larger than 4 cm; no evidence of regional lymph node involvement or distant metastasis.

Stage III: Tumor is larger than 4 cm; in some cases, the tumor has spread to the lymph nodes; no evidence of distant metastasis.

Stage IV: Tumor has spread to the lymph nodes; in some cases, distant metastases are present.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Human Monoclonal Antibodies that Specifically Bind HMW-MAA

Disclosed herein are human monoclonal antibodies and functional fragments thereof that specifically bind HMW-MAA. In one example, HMW-MAA has an amino acid sequence set forth as:

```
                                               (SEQ ID NO: 14)
EQMREEPEAA YRLIQGPQYG HLLVGGRPTS AFSQFQIDQG

EVVFAFTNFS SSHDHFRVLA LARGVNASAV VNVTVRALLH

VWAGGPWPQG ATLRLDPTVL DAGELANRTG SVPRFRLLEG

PRHGRVVRVP RARTEPGGSQ LVEQFTQQDL EDGRLGLEVG

RPEGRAPGPA GDSLTLELWA QGVPPAVASL DFATEPYNAA

RPYSVALLSV PEAARTEAGK PESSTPTGEP GPMASSPEPA

VAKGGFLSFL EANMFSVIIP MCLVLLLLAL ILPLLFYLRK

RNKTGKHDVQ VLTAKPRNGL AGDTETFRKV EPGQAIPLTA

VPGQLFP
```

See also GENBANK® Accession No. AAI28111 incorporated herein by reference)

HMW-MAA is a human melanoma-associated chondroitin sulfate proteoglycan that plays a role in stabilizing cell-substratum interactions during early events of melanoma cell spreading on endothelial basement membranes. CSPG4 represents an integral membrane chondroitin sulfate proteoglycan expressed by human malignant melanoma cells.

HMW-MAA is also known as CSPG4. In vivo, it is present in a molecule that consists of two noncovalently associated glycopolypeptides. One has an apparent molecular weight of 280K, and the other has an apparent molecular weight greater than 440K. HMW-MAA is synthesized and expressed by human melanoma cells (Spiro, R. C. et al. F. Biol. Chem. 264:1779 (1989); Esko, J. D., et al., Science 241:1092, 1988). Proteoglycans are glycoproteins with glycosaminoglycan (GAG) polysaccharide chains covalently attached to the serine residue in their core. The M+HMW-MAA core protein is initially translated as a precursor with a molecular mass of 240K with asparagine N-linked oligosaccharides of the high mannose type.

In another example, the HMW-MAA is encoded by the nucleic acid sequence set forth as:

```
                                               (SEQ ID NO: 15)
gggagcagat gagggaggag ccagaggcag cataccgcct catccaggga ccccagtatg ggcatctcct ggtgggcggg cggcccacct cggccttcag ccaattccag atagaccagg
```

```
gcgaggtggt ctttgccttc accaacttct cctcctctca tgaccacttc agagtcctgg cactggctag gggtgtcaat gcatcagccg tagtgaacgt cactgtgagg gctctgctgc atgtgtgggc aggtgggcca tggcccagg gtgccaccct gcgcctggac cccaccgtcc tagatgctgg cgagctggcc aaccgcacag gcagtgtgcc gcgcttccgc ctcctggagg gacccggca tggccgcgtg gtccgcgtgc cccgagccag gacggagccc gggggcagcc agctggtgga gcagttcact cagcaggacc ttgaggacgg gaggctgggg ctggaggtgg gcaggccaga ggggagggcc cccggccccg caggtgacag tctcactctg gagctgtggg cacagggcgt cccgcctgct gtggcctccc tggactttgc cactgagcct tacaatgctg cccggcccta cagcgtggcc ctgctcagtg tccccgaggc cgcccggacg gaagcaggga agccagagag cagcaccccc acaggcgagc caggcccat ggcatccagc cctgagcccg ctgtggccaa gggaggcttc ctgagcttcc ttgaggccaa catgttcagc gtcatcatcc ccatgtgcct ggtacttctg ctcctggcgc tcatcctgcc cctgctcttc tacctccgaa aacgcaacaa gacgggcaag catgacgtcc aggtcctgac tgccaagccc cgcaacggcc tggctggtga caccgagacc tttcgcaagg tggagccagg ccaggccatc ccgctcacag ctgtgcctgg ccagttattt cca
```

See also GENBANK® Accession No. BC128110, incorporated herein by reference. Once of skill in the art can readily use a nucleic acid sequence to produce a polypeptide, such as HMW-MAA using standard method in molecular biology (see, for example, *Molecular Cloning: A Laboratory Manual*, 2nd ed., vol. 1-3, ed. Sambrook et al., Cold Spring Harbor Laboratory Press, Cold Spring Harbor, N. Y., 1989).

Described herein are isolated human monoclonal antibodies and fragments thereof that specifically bind human HMW-MAA. In some embodiments, the human monoclonal antibody functional fragment is a scFv. Also described are compositions including the provided human monoclonal antibodies or functional fragment thereof and a pharmaceutically acceptable carrier. Nucleic acids encoding these antibodies, expression vectors comprising these nucleic acids, and isolated host cells that express the nucleic acids are also provided.

Also described herein are immunoconjugates comprising the human monoclonal antibodies or functional fragment thereof that specifically binds human HMW-MAA. The immunoconjugates can comprise any therapeutic agent, toxin or other moiety. In one example, the toxin is PE or a variant or fragment thereof. Compositions comprising the immunoconjugates are also described.

Compositions comprising the human monoclonal antibodies that specifically bind HMW-MAA or functional fragment thereof can be used for screening, research, detection and therapeutic purposes. For example, the human monoclonal antibodies or functional fragment thereof can be used to identify other antibodies that specifically bind HMW-MAA, such as in competitive immunoassays.

Compositions comprising the human monoclonal antibodies that specifically bind HMW-MAA or functional fragment thereof can be used to treat a subject diagnosed with cancer, such as a cancer that exhibits increased expression of HMW-MAA relative to normal cells. For example, the antibodies can be used to treat melanoma, breast cancer, prostate cancer, ovarian cancer, colon cancer, stomach cancer, pancreatic cancer, glioma, chordoma, chondrosarcoma, glioma or a squamous cell carcinoma. Melanoma includes spreading melanoma, nodular melanoma, acral lentiginous melanoma, and lentigo maligna (melanoma). Squamous cells carcinomas include, but are not limited to head and neck squamous cell carcinoma, and squamous cell cancers of the skin, lung, prostate, esophagus, vagina and cervix.

Compositions comprising the HMW-MAA antibodies can also be used to prevent metastasis or decrease the number of micrometastases, such as micrometastases to regional lymph nodes. Immunoconjugates comprising the HMW-MAA antibodies also can be used to treat a patient diagnosed with cancer. The human monoclonal antibodies can also be used to diagnose cancer in a subject. For example, the human monoclonal antibodies can be contacted with a sample from the patient, such as a serum sample, to detect elevated levels of HMW-MAA. The antibodies and compositions provided herein can also be used to detect cancer in a subject or to confirm the diagnosis of cancer in a patient.

Disclosed herein are fully human monoclonal antibodies that specifically bind human HMW-MAA and functional fragments thereof. A major limitation in the clinical use of mouse monoclonal antibodies is the development of a human anti-murine antibody (HAMA) response in the patients receiving the treatments. The HAMA response can involve allergic reactions and an increased rate of clearance of the administered antibody from the serum. Various types of modified monoclonal antibodies have been developed to minimize the HAMA response while trying to maintain the antigen binding affinity of the parent monoclonal antibody. One type of modified monoclonal antibody is a human-mouse chimera in which a murine antigen-binding variable region is coupled to a human constant domain (Morrison and Schlom, *Important Advances in Oncology*, Rosenberg, S. A. (Ed.), 1989). A second type of modified monoclonal antibody is the complementarity determining region (CDR)-grafted, or humanized, monoclonal antibody (Winter and Harris, *Immunol. Today* 14:243-246, 1993). However, the antibodies disclosed herein are fully human; both the framework region and the CDRs are derived from human sequences. Thus, a HAMA is not induced when these antibodies are administered to a human subject.

In some embodiments, the human monoclonal antibody or functional fragment thereof comprises at least a portion of the heavy chain amino acid sequence set forth as SEQ ID NO: 5 and specifically binds HMW-MAA. In some embodiments, the human monoclonal antibody or functional fragment thereof comprises at least a portion of the light chain amino acid sequence set forth as SEQ ID NO: 6 and specifically binds HMW-MAA. In some examples, the heavy chain of the antibody comprises amino acids 27-38 of SEQ ID NO: 5 (CDR1), amino acids 56-65 of SEQ ID NO: 5 (CDR2), amino acids 105-115 of SEQ ID NO: 5 (CDR3), or a combination thereof. In some examples, the heavy chain of the antibody comprises the heavy chain of the antibody comprises amino acids 27-38 of SEQ ID NO: 5 (CDR1), amino acids 56-65 of SEQ ID NO: 5 (CDR2), and amino acids 105-115 of SEQ ID NO: 5 (CDR3). In some examples, the light chain of the antibody comprises amino acids 27-38 of SEQ ID NO: 6 (CDR1), amino acids 56-65 of SEQ ID NO: 6 (CDR2), amino acids 105-110 of SEQ ID NO: 6 (CDR3), or a combination thereof. In some examples, the light chain of the antibody comprises amino acids 27-38 of SEQ ID NO: 6 (CDR1), amino acids 56-65 of SEQ ID NO: 6 (CDR2), and amino acids 105-110 of SEQ ID NO: 6 (CDR3). In some embodiments, the human monoclonal antibody is labeled. In some examples, the label is a fluorescence, enzymatic, or radioactive label.

The monoclonal antibody can be of any isotype. The monoclonal antibody can be, for example, an IgM or an IgG antibody, such as $IgG_1$ or an $IgG_2$. The class of an antibody that specifically binds HMW-MAA can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds HMW-MAA that was originally IgM may be class switched to an IgG. Class switching can be used to convert one IgG subclass to another, such as from $IgG_1$ to $IgG_2$.

Fully human monoclonal antibodies include human framework regions. The human framework regions can include the framework regions disclosed in one or both of SEQ ID NO: 5 or SEQ ID NO: 6 (these sequences include CDR sequences as well as framework sequences). However, the framework regions can be from another source. Additional examples of framework sequences that can be used include the amino acid framework sequences of the heavy and light chains disclosed in PCT Publication No. WO 2006/074071 (see, for example, SEQ ID NOs: 1-16), which is herein incorporated by reference.

Antibody fragments are encompassed by the present disclosure, such as Fab, F(ab')$_2$, and Fv which include a heavy chain and light chain variable region and are capable of binding the epitopic determinant on HMW-MAA. These antibody fragments retain the ability to specifically bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV$_2$), defined as a dimer of a scFV. This has also been termed a "miniantibody."

Methods of making these fragments are known in the art (see for example, Harlow and Lane, *Antibodies: A Laboratory Manual*, Cold Spring Harbor Laboratory, New York, 1988). In several examples, the variable region included in the antibody is the variable region of M912.

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

IV. Immunoconjugates for Use in Therapeutic and Diagnostic Moieties

The human monoclonal antibodies, or functional fragments thereof, that specifically bind human HMW-MAA can be used in therapeutic methods. In several embodiments, the human monoclonal antibodies or functional fragments thereof described herein can be conjugated to a therapeutic agent. Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or Diphtheria toxin, encapsulating agents (such as liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell. Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments that specifically bind HMW-MAA disclosed herein can be derivatized or linked to another molecule (such as another peptide or protein). In general, the antibodies or portion thereof is derivatized such that the binding to HMW-MAA is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

A human antibody that specifically binds HMW-MAA or functional fragment thereof can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect HMW-MAA by x-ray, emission spectra, magnetic resonance imaging (MRI), commuted tomography (CT) scan, positron emission tomography (PET), or other diagnostic techniques. Examples of labels for polypeptides include, but are not limited to, the following radioisotopes or radionucleotides: $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the HMW-MAA-specific human monoclonal antibodies, and functional fragments thereof, that are described herein, to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is Pseudomonas exotoxin (PE) (U.S. Pat. No. 5,602,095). As used herein "Pseudomonas exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., J. Biol. Chem. 264:14256-14261, 1989). In one embodiment, the cytotoxic fragment of PE retains at least 50%, at least 75%, at least 90%, or at lest 95% of the cytotoxicity of native PE. In some examples, the cytotoxic fragment is more toxic than native PE.

Native Pseudomonas exotoxin A (PE) is an extremely active monomeric protein (molecular weight 66 kD), secreted by Pseudomonas aeruginosa, which inhibits protein synthesis in eukaryotic cells. The method of PE action is inactivation of the ADP-ribosylation of elongation factor 2 (EF-2). The exotoxin contains three structural domains that act in concert to cause cytotoxicity. Domain 1a mediates cell binding. Domain II is responsible for translocation into the cytosol and domain III mediates ADP ribosylation of elongation factor 2. The function of domain Ib is unknown. PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pai et al., Proc. Natl Acad. Sci. USA 88:3358-3362, 1991; Kondo et al., J. Biol. Chem. 263:9470-9475, 1988; Pastan et al., Biochim. Biophys. Acta 1333:C1-C6, 1997, each of which is herein incorporated by reference.

The antibodies and functional fragments thereof described herein can also be used to target any number of different diagnostic or therapeutic compounds to cells expressing HMW-MAA on their surface. Thus, an antibody of the present disclosure can be attached directly or via a linker to a drug that is to be delivered directly to cells expressing cell-surface HMW-MAA. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-HMW-MAA antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., Pharm. Ther. 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^{3}H$, $^{125}I$, $^{35}S$, $^{14}C$, or $^{32}P$), enzymes (such as horseradish peroxidase, alkaline phosphatase and others commonly used in an ELISA), and colorimetric labels such as colloidal gold or colored glass or plastic (such as polystyrene, polypropylene, latex, and the like) beads. These antibodies can be used in a variety of immunoassays, including Fluorescence activated cells sorting (FACS), immunohistochemistry, radioimmunoassays (RIAs), and enzyme-linked immunosorbent assays (ELISA).

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

V. HMW-MAA Antibody Polynucleotides and Polypeptides

Nucleic acid molecules (also referred to as polynucleotides) encoding the polypeptides provided herein (including, but not limited to antibodies, functional fragments thereof, immunoconjugates and fusion proteins) can readily be produced by one of skill in the art, using the amino acid sequences provided herein, sequences available in the art, and the genetic code. In addition, one of skill can readily construct a variety of clones containing functionally equivalent nucleic acids, such as nucleic acids which differ in sequence but which encode the same effector molecule or antibody sequence. Thus, nucleic acids encoding antibodies, conjugates and fusion proteins are provided herein.

In some embodiments, the HMW-MAA human monoclonal antibodies have a $V_H$ domain encoded by a nucleotide sequence comprising SEQ ID NO: 1. In some embodiments, the HMW-MAA human monoclonal antibodies have a $V_L$ domain encoded by the nucleotide sequence comprising SEQ ID NO: 3. In some embodiments, the HMW-MAA human monoclonal antibodies have a heavy chain comprising the nucleotide sequence of SEQ ID NO: 4.

Nucleic acid sequences encoding the human antibodies that specifically bind HMW-MAA, or functional fragments thereof that specifically bind HMW-MAA, can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding human antibodies that specifically bind HMW-MAA, or functional fragments thereof that specifically bind HMW-MAA, can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids encoding native effector molecule (EM) or anti-HMW-MAA antibodies can be modified to form the EM, antibodies, or immunoconjugates of the present disclosure. Modification by site-directed mutagenesis is well known in the art. Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one embodiment, immunoconjugates are prepared by inserting the cDNA which encodes a human HMW-MAA-specific monoclonal antibody or functional fragment thereof into a vector which comprises the cDNA encoding the EM. The insertion is made so that the antibody and the EM are read in frame, that is in one continuous polypeptide which contains a functional antibody region and a functional EM region. In one embodiment, cDNA encoding an EM, label or enzyme is ligated to an antibody so that the EM, label or enzyme is located at the carboxyl terminus of the antibody. In another embodiment, the EM, label or enzyme is located at the amino terminus of the antibody. In a another example, cDNA encoding the EM, label or enzyme is ligated to a heavy chain variable region of an antibody, so that the EM, label or enzyme is located at the carboxyl terminus of the heavy chain variable region. The heavy chain-variable region can subsequently be ligated to a light chain variable region of the antibody using disulfide bonds. In a yet another example, cDNA encoding an EM, label or enzyme is ligated to a light chain variable region of an antibody, so that the EM, label or enzyme is located at the carboxyl terminus of the light chain variable region. The light chain-variable region can subsequently be ligated to a heavy chain variable region of the antibody using disulfide bonds.

Once the nucleic acids encoding an EM, anti-HMW-MAA antibody, functional fragment thereof, or an immunoconjugate, are isolated and cloned, the desired protein can be expressed in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the isolated antibodies and antibody fragments described herein can be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation, and a transcription/translation terminator. For E. coli, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, SV40 or cytomegalovirus, and a polyadenylation sequence, and can further include splice donor and acceptor sequences. The cassettes can be transferred into the chosen host cell by well-known methods such as transformation or electroporation for E. coli and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein (i.e., a human HMW-MAA-specific monoclonal antibody or an immunoconjugate comprising the antibody) without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the recombinant immunoconjugates, antibodies, and/or effector molecules can be purified according to standard procedures of the art, including ammonium sulfate precipitation, affinity columns, column chromatography, and the like (see, generally, R. Scopes, PROTEIN PURIFICATION, Springer-Verlag, N. Y., 1982). The antibodies, immunoconjugates and effector molecules need not be 100% pure. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as E. coli have been described and are well-known and are applicable to the antibodies disclosed herein. See, Buchner et al., Anal. Biochem. 205:263-270, 1992; Pluckthun, Biotechnology 9:545, 1991; Huse et al., Science 246:1275, 1989 and Ward et al., Nature 341:544, 1989, all incorporated by reference herein.

Often, functional heterologous proteins from E. coli or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., Biochemistry 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

VI. Compositions and Therapeutic Methods

Compositions are provided herein that include a carrier and one or more of the antibodies that specifically bind HMW-MAA, or functional fragment thereof that specifically binds HMW-MAA. Compositions comprising immunoconjugates or immunotoxins are also provided. The compositions can be prepared in unit dosage forms for administration to a subject. The amount and timing of administration are at the discretion of the treating physician to achieve the desired purposes. The antibody can be formulated for systemic or local (such as intra-tumor) administration. In one example, the antibody that specifically binds HMW-MAA is formulated for parenteral administration, such as intravenous administration.

The compositions for administration can include a solution of the antibody that specifically binds HMW-MAA (or a functional fragment thereof) dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

The antibody that specifically binds HMW-MAA (or functional fragment thereof) can be administered to slow or inhibit the growth of cells, such as cancer cells. In these applications, a therapeutically effective amount of an antibody is administered to a subject in an amount sufficient to inhibit growth, replication or metastasis of cancer cells, or to inhibit a sign or a symptom of the cancer. In some embodiments, the antibodies are administered to a subject to inhibit or prevent the development of metastasis, or to decrease the size or number of metastases, such as micrometastases, for example micrometastases to the regional lymph nodes (Goto et al., *Clin. Cancer Res.* 14(11):3401-3407, 2008).

Suitable subjects may include those diagnosed with a cancer that expresses HMW-MAA, such as, but not limited to, melanoma, prostate cancer, squamous cell carcinoma (such as head and neck squamous cell carcinoma), breast cancer (including, but not limited to basal breast carcinoma, ductal carcinoma and lobular breast carcinoma), leukemia (such as acute myelogenous leukemia and 11q23-positive acute leukemia), a neural crest tumor (such as an astrocytoma, glioma or neuroblastoma), ovarian cancer, colon cancer, stomach cancer, pancreatic cancer, bone cancer (such as a chordoma), glioma or a sarcoma (such as chondrosarcoma).

A therapeutically effective amount of a human HMW-MAA-specific antibody will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with another chemotherapeutic agent, either simultaneously or sequentially.

Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the invention. Examples of useful COX-II inhibitors include CELEBREX™ (alecoxib), valdecoxib, and rofecoxib. Examples of useful matrix metalloproteinase inhibitors are described in PCT Publication No. WO 96/33172 (published Oct. 24, 1996), PCT Publication No. WO 96/27583 (published Mar. 7, 1996), European Patent Application No. 97304971.1 (filed Jul. 8, 1997), European Patent Application No. 99308617.2 (filed Oct. 29, 1999), PCT Publication No. WO 98/07697 (published Feb. 26, 1998), PCT Publication No WO 98/03516 (published Jan. 29, 1998), PCT Publication No WO 98/34918 (published Aug. 13, 1998), PCT Publication No WO 98/34915 (published Aug. 13, 1998), PCT Publication No WO 98/33768 (published Aug. 6, 1998), PCT Publication No WO 98/30566 (published Jul. 16, 1998), European Patent Publication 606,046 (published Jul. 13, 1994), European Patent Publication 931,788 (published Jul. 28, 1999), PCT Publication No WO 90/05719 (published May 31, 1990), PCT Publication No WO 99/52910 (published Oct. 21, 1999), PCT Publication No WO 99/52889 (published Oct. 21, 1999), PCT Publication No WO 99/29667 (published Jun. 17, 1999), PCT International Application No. PCT/IB98/01113 (filed Jul. 21, 1998), European Patent Application No. 99302232.1 (filed Mar. 25, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997). In one example, the MMP inhibitors do not induce arthralgia upon administration. In another example, the MMP inhibitor selectively inhibits MMP-2 and/or MMP-9 relative to the other matrix-metalloproteinases (such as MMP-1, MMP-3, MMP-4, MMP-5, MMP-6, MMP-7, MMP-8, MMP-10, MMP-11, MMP-12, and MMP-13). Some specific examples of MMP inhibitors of use are AG-3340, RO 32-3555, RS 13-0830, 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxaicyclo[3.2.1]octane-3-carboxylic acid hydroxyamide; 3-endo-3-[4-(4-fluoro-phenoxy)-benzenesulfonylamino]-8-oxa-icyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

The antibodies that specifically bind HMW-MAA can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in PCT Publication Nos. WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents also include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), C1-1033 (Warner Lambert Parke Davis), Cl-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)).

VEGF inhibitors, for example SU-5416 and SU-6668 (Sugen Inc.), SH-268 (Schering), and NX-1838 (NeXstar) can also be used in conjunction with an antibody that specifically binds HMW-MAA. VEGF inhibitors are described in, for example in PCT Publication No. WO 99/24440 (published May 20, 1999), PCT International Application PCT/IB99/00797 (filed May 3, 1999), PCT Publication No. WO 95/21613 (published Aug. 17, 1995), PCT Publication No. WO 99/61422 (published Dec. 2, 1999), U.S. Pat. No. 5,834,504 (issued Nov. 10, 1998), PCT Publication No. WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), PCT Publication No. WO 99/10349 (published Mar. 4, 1999), PCT Publication No. WO 97/32856 (published Sep. 12, 1997), PCT Publication No. WO 97/22596 (published Jun. 26, 1997), PCT Publication No. WO 98/54093 (published Dec. 3, 1998), PCT Publication No. WO 98/02438 (published Jan. 22, 1998), WO 99/16755 (published Apr. 8, 1999), and PCT Publication No. WO 98/02437 (published Jan. 22, 1998). Other examples of some specific VEGF inhibitors are IM862 (Cytran Inc.); anti-VEGF monoclonal antibody of Genentech, Inc.; and angiozyme, a synthetic ribozyme from Ribozyme and Chiron. These and other VEGF inhibitors can be used in conjunction with an antibody that specifically binds HMW-MAA.

ErbB2 receptor inhibitors, such as GW-282974 (Glaxo Wellcome pic), and the monoclonal antibodies AR-209 (Aronex Pharmaceuticals Inc.) and 2B-1 (Chiron), can furthermore be combined with the compound of the invention, for example those indicated in PCT Publication No. WO 98/02434 (published Jan. 22, 1998), PCT Publication No. WO 99/35146 (published Jul. 15, 1999), PCT Publication No. WO 99/35132 (published Jul. 15, 1999), PCT Publication No. WO 98/02437 (published Jan. 22, 1998), PCT Publication No. WO 97/13760 (published Apr. 17, 1997), PCT Publication No. WO 95/19970 (published Jul. 27, 1995), U.S. Pat. No. 5,587,458 (issued Dec. 24, 1996), and U.S. Pat. No. 5,877,305 (issued Mar. 2, 1999). ErbB2 receptor inhibitors of use are also described in U.S. Provisional Application No. 60/117,341, filed Jan. 27, 1999, and in U.S. Provisional Application No. 60/117,346, filed Jan. 27, 1999.

For the treatment of cancer, such as melanoma, the antibodies disclosed herein can be used with surgical treatment, or with another therapeutic including dacarbazine (also termed DTIC), or interleukin-2 (IL-2) or interferon, such as interferon (IFN). For the treatment of a superficial melanoma, the antibodies can be used in conjunction with Imiquimod. For treatment of prostate cancer, the antibodies can be used in conjunction with, for example, surgery, radiation therapy, chemotherapy and hormonal therapy (such as anti-androgens or GnRH antagonists). For the treatment of HNSCC, the antibodies provided herein can be used in conjunction with surgery, radiation therapy, chemotherapy, other antibodies (such as cetuximab and bevacizumab) or small-molecule therapeutics (such as erlotinib).

Single or multiple administrations of the compositions are administered depending on the dosage and frequency as required and tolerated by the patient. In any event, the composition should provide a sufficient quantity of at least one of the antibodies (or functional fragments thereof) disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992) both of which are incorporated herein by reference.

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

Fully human monoclonal antibodies that specifically bind HMW-MAA, or a functional fragment thereof, covalently linked to an effector molecule can be used for a variety of purposes, including for radioimmunotherapy or radioimmunoguided surgery. For example, a HMW-MAA antibody can be linked to a radioactive isotope and used in immunotherapy to treat a tumor expressing HMW-MAA. A human HMW-MAA antibody covalently linked to a radioactive isotope is of use to localize a tumor in radioimmunoguided surgery, such that the tumor can be surgically removed. In one embodiment, about 10 mCi of a radiolabeled human HMW-MAA monoclonal antibody is administered to a subject. In other embodiments, about 15 mCi, about 20 mCi, about 50 mCi, about 75 mCi or about 100 mCi of a radiolabeled human HMW-MAA monoclonal antibody is administered to a subject. In other embodiments, about 100 mCi to about 100 mCi of a radiolabeled human HMW-MAA monoclonal antibody is administered to a subject.

A method of detecting tumors in a subject includes the administration of a human antibody that specifically binds HMW-MAA, or functional fragment thereof, complexed to an effector molecule, such as a radioactive isotope. After a sufficient amount of time has elapsed to allow for the administered radiolabeled antibody to localize to the tumor, the tumor is detected. In one specific, non-limiting example, a radiolabeled immune complex is detected using a hand held gamma detection probe. In some embodiments, the tumor is detected by MRI, CT scan or PET scan. Primary tumors, metastasized tumors, or cells expressing HMW-MAA can be detected. For example, a human HMW-MAA monoclonal antibody complexed to an effector molecule, such as a radioactive isotope, is administered to a subject prior to surgery or treatment. In one specific embodiment, the detection step is performed prior to surgery to localize the tumor. In another embodiment, the detection step is performed during surgery, for example to detect the location of the tumor prior to removing it, as in radioimmunoguided surgery. A human HMW-MAA monoclonal antibody complexed to an effector molecule, such as a radioactive isotope, can also be administered to a subject following surgery or treatment, to determine the effectiveness of the treatment, such as to ensure the complete removal of the tumor, or to detect a recurrence of the tumor. Thus, the antibodies are of use as therapeutic agents (such as for immunotherapy against tumors) or for carrying out radioimmunoguided surgery.

VI. Diagnostic Methods and Kits

A method is provided herein for the detection of the expression of HMW-MAA in vitro or in vivo. In one example, expression of HMW-MAA is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine.

In several embodiments, a method is provided for detecting a malignancy such as melanoma, prostate cancer, squamous cell carcinoma (such as head and neck squamous cell carcinoma), breast cancer (including, but not limited to basal breast carcinoma, ductal carcinoma and lobular breast carcinoma), leukemia (such as acute myelogenous leukemia and 11q23-positive acute leukemia), a neural crest tumor (such as an astrocytoma, glioma or neuroblastoma), ovarian cancer, colon cancer, stomach cancer, pancreatic cancer, bone cancer (such as a chordoma), glioma, or a sarcoma (such as chondrosarcoma). Serum samples from patients with HMW-MAA-positive cancers contain detectable amounts of HMW-MAA (Vergilis et al., *J. Invest. Dermatol.* 125:526-531, 2005; Ulmer et al., *Clin. Cancer Res.* 10:531-537, 2004). Thus, antibodies that specifically bind HMW-MAA, or functional fragments thereof, can be used to detect HMW-MAA in a serum sample from a subject to detect cancer in the subject, or confirm a diagnosis of cancer in a subject.

The disclosure provides a method for detecting HMW-MAA in a biological sample, wherein the method includes contacting a biological sample with a human antibody that binds HMW-MAA, or a functional fragment thereof, under conditions conducive to the formation of an immune complex, and detecting the immune complex, to detect the HMW-MAA in the biological sample. In one example, the detection of HMW-MAA in the sample indicates that the subject has a malignancy. In another example, detection of HMW-MAA in the sample confirms a diagnosis of cancer in a subject. In a further example, detection of HMW-MAA confirms or detects the presence of metastases.

In some embodiments, the fully human monoclonal antibody that specifically binds HMAW-MAA, or functional fragment thereof, is used for detection or diagnosis of a tumor in a subject, such as confirming the diagnosis of a tumor in a subject. In other embodiments, the fully human monoclonal antibody that specifically binds HMAW-MAA, or functional fragment thereof, is used to detect the efficacy of a therapy. For example, a subject with a known malignancy that expresses HMW-MAA is administered a therapeutic agent. The method can include contacting a biological sample with a human antibody that binds HMW-MAA, or a functional fragment thereof, under conditions conducive to the formation of an immune complex, and detecting the immune complex, to detect the HMW-MAA in the biological sample. A decrease in the amount of HMW-MAA, as compared to a control, such as a sample from the subject prior to treatment or a reference standard, indicates that the therapeutic agent is effective at treating the malignancy. In some examples, an increase in the amount of HMW-MAA, as compared to the control indicates that the therapeutic agent is not effective for treating the malignancy.

In some embodiments, the detection can be in vivo. The human monoclonal antibody that specifically binds HMAW-MAA, or functional fragment thereof, can be complexed to a radioactive isotope. After a sufficient amount of time has elapsed to allow for the administered radiolabeled antibody to localize to the tumor, the tumor is detected, such as by MRI, CT scan or PET scan.

In one embodiment, the human antibody that specifically binds HMW-MAA or functional fragment thereof is directly labeled with a detectable label. In another embodiment, the human antibody that specifically binds HMW-MAA or functional fragment thereof (the first antibody) is unlabeled and a second antibody or other molecule that can bind the human antibody that specifically binds HMW-MAA is labeled. As is well known to one of skill in the art, a second antibody is chosen that is able to specifically bind the specific species and class of the first antibody. For example, if the first antibody is a human IgG, then the secondary antibody may be an anti-human-lgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$.

In an alternative embodiment, HMW-MAA can be assayed in a biological sample by a competition immunoassay utilizing HMW-MAA standards labeled with a detectable substance and an unlabeled human antibody that specifically binds HMW-MAA. In this assay, the biological sample, the labeled HMW-MAA standards and the human antibody that specifically bind HMW-MAA or functional fragment thereof are combined and the amount of labeled HMW-MAA standard bound to the unlabeled antibody is determined. The amount of HMW-MAA in the biological sample is inversely proportional to the amount of labeled HMW-MAA standard bound to the antibody that specifically binds HMW-MAA, or functional fragment thereof.

The immunoassays and method disclosed herein can be used for a number of purposes. In one embodiment, the human antibody that specifically binds HMW-MAA or functional fragment thereof may be used to detect the production of HMW-MAA in cells in cell culture. In another embodiment, the antibody can be used to detect the amount of HMW-MAA in a biological sample. Increased expression of HMW-MAA is associated with several types of cancer, including, but not limited to melanoma, breast cancer, prostate cancer, glioma and squamous cell carcinoma. In one embodiment, a kit is provided for detecting HMW-MAA in a biological sample, such as a serum sample or tissue sample. For example, to confirm a cancer diagnosis in a subject, a biopsy can be performed to obtain a tissue sample for histological examination. Alternatively, a serum sample can be obtained to detect the presence of HMW-MAA protein. Kits for detecting a polypeptide will typically comprise a human antibody that specifically binds HMW-MAA, such as any of the antibodies disclosed herein. In some embodiments, an antibody fragment, such as an Fv fragment or scFv, or a Fab is included in the kit. In a further embodiment, the antibody is labeled (for example, with a fluorescent, radioactive, or an enzymatic label).

In one embodiment, a kit includes instructional materials disclosing means of use of an antibody that specifically binds HMW-MAA. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting HMW-MAA in a biological sample generally includes the steps of contacting the biological sample with an antibody or antibody fragment which specifically reacts, under immunologically reactive conditions, to a HMW-MAA polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbent assays (ELISA), or immunohistochemical assays. The antibodies can also be used for fluorescence microscopy or fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the human antibodies that specifically bind HMW-MAA, as disclosed herein, can be used in these assays. Thus, the antibodies can be used in a conventional immunoassay, including, without limitation, an ELISA, an RIA, FACS, tissue immunohistochemistry, Western blot or immunoprecipitation.

VII. Peptide Mimics

Also provided herein are peptides mimics of HMW-MAA. The peptide mimics specifically bind a human monoclonal antibody specific for HMW-MAA. The peptide mimics were identified by panning a peptide library with HMW-MAA-specific human monoclonal antibody scFv C21. The HMW-MAA peptide mimics can be used, for example, to elicit a HMW-MAA-specific immune response in a subject diagnosed with a HMW-MAA-positive cancer, such as melanoma.

Provided herein are isolated peptides that bind a human monoclonal antibody specific for HMW-MAA, wherein the peptide comprises the consensus motif PXXYXPXXD (SEQ ID NO: 9). The peptide mimics are generally about 10 to about 20 amino acids in length, such as about 13 to about 17, or about 15 amino acids in length. In some embodiments, the peptides are 10, 11, 12, 13, 14, 15, 16, 17, 18, 19 or 20 amino acids in length. In some examples, the amino acid sequence of the peptide comprises SEQ ID NO: 7, SEQ ID NO: 10, SEQ ID NO: 13, or a variant of SEQ ID NO: 7, SEQ ID NO: 10, or SEQ ID NO: 13, wherein the variant comprises no more than three, no more than two or no more than one amino acid substitutions. In particular examples, the amino acid sequence of the peptide consists of SEQ ID NO: 7, SEQ ID NO: 10 or SEQ ID NO: 13.

Also provided is a method of inducing HMW-MAA-specific immunity in a subject, comprising administering to the subject the peptide comprising the consensus motif PXXYXPXXD (SEQ ID NO: 9).

The following examples are provided to illustrate certain particular features and/or embodiments. These examples should not be construed to limit the disclosure to the particular features or embodiments described.

EXAMPLES

Example 1

Materials and Methods

Cell Lines, Cell Lysate and Tissues

The human melanoma cell lines Colo38, FO-1 and Melur and the human B lymphoid cell line LG2 were maintained in RPMI 1640 medium (Tissue Culture Media Facility, Roswell Park Cancer Institute (RPCI), Buffalo, N.Y.) supplemented with 10% serum plus supplement (BioWhittaker, Walkersville, Md.) and 2 mM L-glutamine (BioWhittaker). The human melanoma cell lines M14 and SK-MEL-28, the human fibroblasts FF2376, the human breast carcinoma cell line T47D, the human bladder carcinoma cell line T24, the human prostate carcinoma cell line PC3, the human B lymphoid cell lines JY and LKT13, and the rat neural cell line B49 were maintained in RPMI 1640 medium supplemented with 10% fetal bovine serum (FBS) (Bio-Whittaker) and 2 mM L-glutamine. The M14/HMW-MAA cells which express HMW-MAA following transfection of M14 cells with a plasmid DNA of pcDNA 3.1™ (+)/full length of HMW-MAA DNA construct (Yang et al., *J Cell Biol* 165:881-891, 2004) were grown in RPMI 1640 medium supplemented with 10% FBS, 2 mM L-glutamine and 0.4 mg/ml G418 (Promega, Madison, Wis.). Cells were cultured at 37° C. in a 5% $CO_2$ atmosphere. Cell lysates were prepared as described (Desai et al., *Cancer Res* 58:2417-2425, 1998, herein incorporated by reference). Lesions of melanocytic origin were obtained from patients who had undergone surgery in the Department of Dermatology at Kumamoto University School of Medicine (Kumamoto, Japan). The diagnosis of melanoma lesions was based on histopathologic characteristics. The frozen and formalin-fixed tissue sections were prepared as described previously (Desai et al., *Cancer Res* 58:2417-2425, 1998, herein incorporated by reference).

Animals

Eight-week old female BALB/c mice were obtained from the animal core facility at RPCI.

Monoclonal and Polyclonal Antibodies, scFv Antibodies and Reagents

The HMW-MAA-specific mouse mAbs 149.53, 225.28, 763.74, TP61.5 and VF1-TP34 and VF1-TP41.2, were developed and characterized as described elsewhere (Wilson et al., *Int J Cancer*, 28:293-300, 1981; Giacomini et al., *Cancer Res* 43:3586-3590, 1983; Chen et al., *Cancer Res* 51:4790-4797, 1991; Temponi et al., *Cancer Res* 52:2497-2503, 1992). Cross-blocking experiments have shown that the 6 mAbs recognize distinct and spatially distant antigenic determinants, since they do not cross-inhibit each other in their binding to HMW-MAA+ melanoma cells (Campoli et al., *Crit Rev Immunol* 24:267-296, 2004). The 100 KD-specific mouse mAb 376.96 (Imai et al., *J Natl Cancer Inst* 68:761-769, 1982), the HLA class I antigen-specific mouse mAb TP25.99 (Desai et al., *J Immunol* 165:3275-3283, 2000), the c-myc oncoprotein-specific mouse mAb 9E10 (Evan et al., *Mol Cell Biol* 5:3610-3616, 1985) and the mouse anti-id mAb MK2-23 (Kusama et al., *J Immunol* 143:3844-3852, 1989) have been previously described. The HMW-MAA-specific human scFv #28 (Noronha et al., *J. Immunol* 161:2968-2976, 1998), #61 (Desai et al., *Cancer Res* 58:2417-2425, 1998), and #70 (Noronha et al., *J. Immunol* 161:2968-2976, 1998) and the anti-anti-id scFv #119 (Wang et al., *Idiotypes in Medicine: Autoimmunity, Infection and Cancer* p. 523, 1997) were isolated from the synthetic scFv library (#1) (Nissim et al., *Embo J* 13:692-698, 1994) by panning with melanoma cells S5, purified HMW-MAA, melanoma cells SK-MEL-28 and anti-id mAb MK2-23, respectively. The MAA-specific human scFv F98 and W34 were isolated from the semi-synthetic scFv library (de Kruif et al., *J Mol Biol* 248:97-105, 1995) by panning with the melanoma cells FO-1 and WM1158, respectively.

Mouse mAbs were purified from ascitic fluid by sequential ammonium sulphate and caprylic acid precipitation (Temponi et al., *Hybridoma* 8:85-95, 1989). The purity and activity of mAb preparations were assessed by SDS-PAGE and by testing with the corresponding antigen in a binding assay, respectively. Monoclonal antibodies and purified scFv antibodies were biotinylated using NHS-LC-biotin (Pierce, Rockford, Ill.) according to the manufacturer's instructions. mAb 9E10 was immobilized on a HiTrap NHS-activated sepharose column (Amersham Biosciences, Piscataway, N.J.) following the manufacturer's instructions.

Streptavidin-horseradish peroxidase conjugate (SA-HRP) was purchased from Pierce. HRP-anti-mouse IgG Fc antibodies were purchased from Jackson ImmunoResearch Laboratories, Inc., West Grove, Pa. R-phycoerythrin (RPE)-labeled F(ab')$_2$ fragments of goat anti-mouse Ig antibodies were purchased from BD Pharmingen, San Diego, Calif.

Phage Display Libraries

A large semi-synthetic phage display scFv antibody library with designed CDR3 was constructed as described (de Kruif et al., *J Mol Biol* 248:97-105, 1995). Phage display peptide libraries X15 displaying 15 amino acid, random linear peptides and LX-8 (XCX8CX) displaying 12 amino acid, random, disulfide constrained peptides were constructed as described (Bonnycastle et al., *J Mol Biol* 258: 747-762, 1996).

Synthetic Peptides

Peptides were purchased from RPCI Biopolymer Core Facility (Buffalo, N.Y.). Peptide P1C21, containing cysteine residues, was cyclized with 6 mM potassium ferricyanide and purified with reversed-phase HPLC. The composition and disulfide bond formation were confirmed by mass spectrometry. Purity of peptides was greater than 95%, as assessed by HPLC. Peptides were reconstituted in water at a concentration of 5 mM, aliquoted and stored at −20° C. Peptide P1C21, which is insoluble in water, was reconstituted in dimethyl sulfoxide (DMSO) at a concentration of 5 mM. Peptides were conjugated to keyhole limpet haemocyanin (KLH) (Pierce) using the coupling agent maleimidobenzoyl-N-hydroxysuccinimide (MBS) (Pierce) as described (Grant, *Current Protocols in Immunology* p. 9.2.8, 2002).

Selection of Phage Display scFv Antibodies

Phage display scFv antibodies binding to melanoma cells were isolated from the phage display scFv antibody library utilizing the panning technique as described (Noronha et al., *J Immunol* 161:2968-2976, 1998, herein incorporated by reference).

Preparation and Purification of Soluble scFv Antibodies

Soluble scFv antibodies were produced from individual ampicillin-resistant *E. Coli* TG1 infected colonies by induction with isopropyl-β-D-thiogalactopyranoside (IPTG) (Roche Applied Science, Indianapolis, Ind.) as described (Schier et al., *J Mol Biol* 255:28-43, 1996, herein incorporated by reference). Soluble scFv antibodies were harvested from culture supernatants (SNT) or from the periplasmic space (periplasmic preparation, PP) of cultures of individual bacterial colonies. scFv antibodies were purified from SNT or PP by affinity chromatography on insolubilized mAb 9E10 following the methodology described for the RPAS purification module (Amersham). Purified scFv antibodies were concentrated using Centricon 10 (Millipore Corporation, Bedford, Mass.) following the manufacturer's instructions. The purity and activity of scFv antibody preparations was assessed by SDS-PAGE utilizing the phastSystem™ (Amersham) and by testing with the corresponding antigen utilizing enzyme linked immunosorbent assay (ELISA), respectively.

Binding Assays

The ELISA to test the reactivity of soluble scFv antibodies with synthetic peptides and melanoma cells and of mouse immune sera with melanoma cells and with peptides was performed as described (Desai et al., *Cancer Res* 58:2417-2425, 1998; Desai et al., *J Immunol* 165:3275-3283, 2000; Matsui et al., *J Immunol* 139:2088-2095, 1987). Results are expressed as absorbance of optical density (O.D.) at 450 nm.

The competition assay to map the antigenic determinant recognized by scFv C21 was performed by mixing biotinylated scFv C21 (0.25 µg/well) with two-fold dilutions of mouse mAb or scFv PP or by mixing biotinylated mAb (at an optimal amount giving absorbance, measured at 450 nm of 1.0) with two fold dilutions of scFv PP. The mixture (100 l/well) was incubated for 1 h at 4° C. with HMW-MAA$^+$ cells ($2\times10^{5/501}$ of RPMI 1640 medium) in a 96-well tissue culture plate (Falcon 3072, Becton Dickinson, Franklin Lakes, N.J.). Binding of biotinylated scFv antibodies and biotinylated mAb to target cells was measured by sequential incubation with SA-HRP and substrate as described (Noronha et al., *J Immunol* 161:2968-2976, 1998). The results are expressed as percent inhibition by mAb, scFv or peptide (competitor or inhibitor) of scFv or mAb binding to HMW-MAA$^+$ cells. The percent inhibition was calculated using the formula: % inhibition=(($OD_{450}$ in the absence of inhibitor–$OD_{450}$ in the presence of inhibitor)/$OD_{450}$ in the absence of inhibitor)×100.

The indirect immunoperoxidase staining of frozen and formalin-fixed tissue sections was performed as described previously (Desai et al., *Cancer Res* 58:2417-2425, 1998, herein incorporated by reference).

Indirect Immunoprecipitation and SDS-PAGE

Labeling of cells with $^{125}$Iodine (Na$^{125}$ I; Amersham) or with $^{35}$S methionine (Trans-$^{35}$S-label, ICN Biochemicals, Costa Mesa, Calif.) in the presence of tunicamycin (Sigma Chemical Co.) was performed as described (Noronha et al., *J Immunol* 161:2968-2976, 1998; Desai et al., *J Immunol* 165:3275-3283, 2000). Solubilization of labelled cells, immunoprecipitation, SDS-PAGE, autoradiography and fluorography were performed as described (Desai et al., *Cancer Res* 58:2417-2425, 1998) except for the use of Gammon Bind plus sepharose (Amersham) instead of protein A coated with rabbit anti-mouse IgG antibodies.

Panning of Peptide Libraries with Biotinylated scFv C21

Micropanning of pVIII libraries X15 and LX-8 with biotinylated scFv C21 was performed in 96 well microtiter plates (Falcon 3076, Becton Dickinson) essentially as described (Desai et al., *J Immunol* 165:3275-3283, 2000, herein incorporated by reference). The first round of panning was performed with $1\times10^{12}$ phage particles in TBS 50 and biotinylated scFv C21 at a concentration of 1 µg per well. The subsequent three rounds of panning were carried out utilizing a phage input of $1\times10^{10}$ phage particles and 0.1 µg per well of biotinylated scFv C21.

Immunological Screening of Phage Display Peptide Libraries

Random phage clones from X15 and LX-8 libraries after the fourth round of panning with scFv C21 were analyzed by immunological screening as described (Desai et al., *J Immunol* 165:3275-3283, 2000, herein incorporated by reference) except for the use of 10 µg/ml of scFv antibody and 5 µg/ml of biotinylated mAb 9E10 to probe the nitrocellulose filter lifts from plates containing colonies.

Sequence Analysis of Phage Display Peptides

The sequence of peptide inserts of phage clones was determined by the dideoxynucleotide chain termination method, as described (Desai et al., *J Immunol* 165:3275-3283, 2000).

Immunization of Mice

BALB/c mice (8 in each group) were immunized subcutaneously (s.c.) with P1C21 peptide-KLH conjugate (50 µg/injection) mixed with an equal volume of complete Freund's adjuvant for priming on day 0 and of incomplete Freund's adjuvant for boosting on day 21, 42, 63, 84 and 105. Mice immunized with the irrelevant peptide MB1$_{194-208}$ derived from the sequence of the proteasome subunit MB1 were used as controls. On day 132, mice were boosted with a s.c. injection of irradiated (20K Rads) cells (5×10$^5$ cells/mouse). Mice were bled one week before the first immunization and one week after each immunization.

Flow Cytometry Analysis

Flow cytometry analysis of melanoma cells stained with scFv antibodies or antibodies in immune sera was performed as described (Wang et al., *J Immunol Methods* 294:23-35, 2004, herein incorporated by reference). Briefly, cells (5×10$^5$) were incubated for 1 h at 4° C. with 12.5 µl of scFv PP or with 0.5 µg of mAb 9E10 (both diluted in a total volume of 100 µl of 2% BSA-PBS) or 100 µl of immune mouse sera. Cells were then washed twice with 0.5% BSA-PBS and incubated for 30 min at 4° C. with an optimal amount of RPE-labeled F(ab')$_2$ fragments of goat anti-mouse Ig antibodies. Following two washes, cells were fixed in 2% formaldehyde and analyzed with a FACScan™ flow cytometer (BD Biosciences, San Jose, Calif.). A total of 10,000 cells were counted using a forward and side scatter gate to eliminate aggregates and debris for each sample. Results are expressed as relative fluorescence intensity.

Delayed-Type Hypersensitivity (DTH) Reaction

Mice which had been immunized six times with peptide P1C21 or control peptide were injected on day 132 s.c. into the right and left hind footpads with irradiated HMW-MAA$^+$ cells Colo38 (5×10$^5$ cells/injection/) and HMW-MAA$^-$ cells LG2 (5×10$^5$ cells/injection/), respectively. The thickness of each footpad was measured and calculated at the indicated times as previously described (Luo et al., *J Immunol* 174: 7104-7110, 2005, herein incorporated by reference).

Statistical Analysis

The statistical significance of the difference among the results obtained in the tested groups was analyzed using the Student's t-test.

Molecular Model of scFv C21-Peptide Complex

The molecular model of scFv C21 was built using AbM (Accelrys, San Diego, Calif.). The VL-VH dimer was created using the crystal structure of influenza virus neuraminidase-(1NMC) (Tulip et al., *J Mol Biol* 227:149-159, 1992) and lysozyme- (Ay et al., *J Mol Biol* 301:239-246, 2000) specific scFv antibodies from protein database (Bernstein et al., *J Mol Biol* 112:535-542, 1977). Classification and numbering schemes to define CDR were according to Kabat et al (Kabat et al., *In Sequences of Proteins of Immunological Interest* 5:91, 1991). The CDR loops L1, H1, L2 and H2 adopt standard canonical conformation. H3 and L3 were built using both loop search of protein database (INSIGHTII, Accelrys) and CONGEN (Bruccoleri et al., *Nature* 335:564-568, 1988). The starting conformations of peptides P1C21 and P3C21 were determined using loop search method built in INSIGHTII. Putative binding interactions of peptides P1C21 and P3C21 with scFv C21 were determined using combination of software AUTODOCK (Morris et al., *J Comput Aided Mol Des* 10:293-304, 1996), INSIGHTII and DOCK (DesJarlais et al., *J Med Chem* 29:2149-2153, 1986).

Kinetic Binding Studies

Binding experiments were performed with the surface plasmon resonance based biosensor instrument BIA-CORE™ 3000 (Biacore AB, Uppsala, Sweden), at 25° C. Immobilization of scFv C21 in the sensor surface was performed following the standard amine coupling procedure according to the manufacturer's instructions. Briefly, 35 µl of a solution containing 0.2 M N-ethyl-N'-(dimethylaminopropyl) carbodiimide (EDC) and 0.05M N-hydroxysuccinimide (NHS), were injected at a flow rate of 5 µl/min to activate carboxyl groups on the sensor chip surface. scFv C21 (40 ng/ml of 10 mM NaOAc buffer, pH 5.0) was flowed over the chip surface at a flow rate of 20 µl/min until the desired bound protein level was reached. Unreacted scFv C21 was washed out and unreacted activated groups were blocked by the injection of 35 µl of 1 M ethanolamine at 5 µl/min. The final immobilization response of scFv C21 was 3,000 RU. A reference surface was generated simultaneously under the same conditions but without scFv C21 injection and used as a blank to correct for instrument and buffer artifacts. Peptides were injected at variable concentrations at different flow rates from 20-100 µl/min. Peptides binding to scFv C21 immobilized on the chip was monitored in real time.

To exclude that binding constants obtained from SPR were not affected by either rebinding of the analyte or mass transport effects, studies were repeated at different flow rates (20-100 µl/min). Kinetic constants obtained at both flow rates remained unchanged.

Example 2

Isolation and Characterization of scFv C21

Isolation of scFv Antibodies by Panning the Semi-Synthetic Phage Display scFv Antibody Library with HMW-MAA$^+$ Cells Colo38

Screening in ELISA with HMW-MAA$^+$ cells Colo 38 and with HMW-MAA$^-$ B lymphoid cells LG2 of 40 soluble scFv antibodies isolated from the semi-synthetic phage display scFv antibody library by panning with Colo38 cells identified 23 clones with selective reactivity with Colo38 cells. Additional testing of the 23 clones with Colo38, FF2376 fibroblasts and T24 bladder carcinoma cells resulted in the isolation of the clones C3, C21, C29 and C30, all of which displayed selective reactivity with Colo38 cells. scFv C21 was selected for further analysis, since it displayed the highest reactivity. The other clones could not be characterized since they were lost.

Analysis of the Specificity of scFv C21

Figure 2:
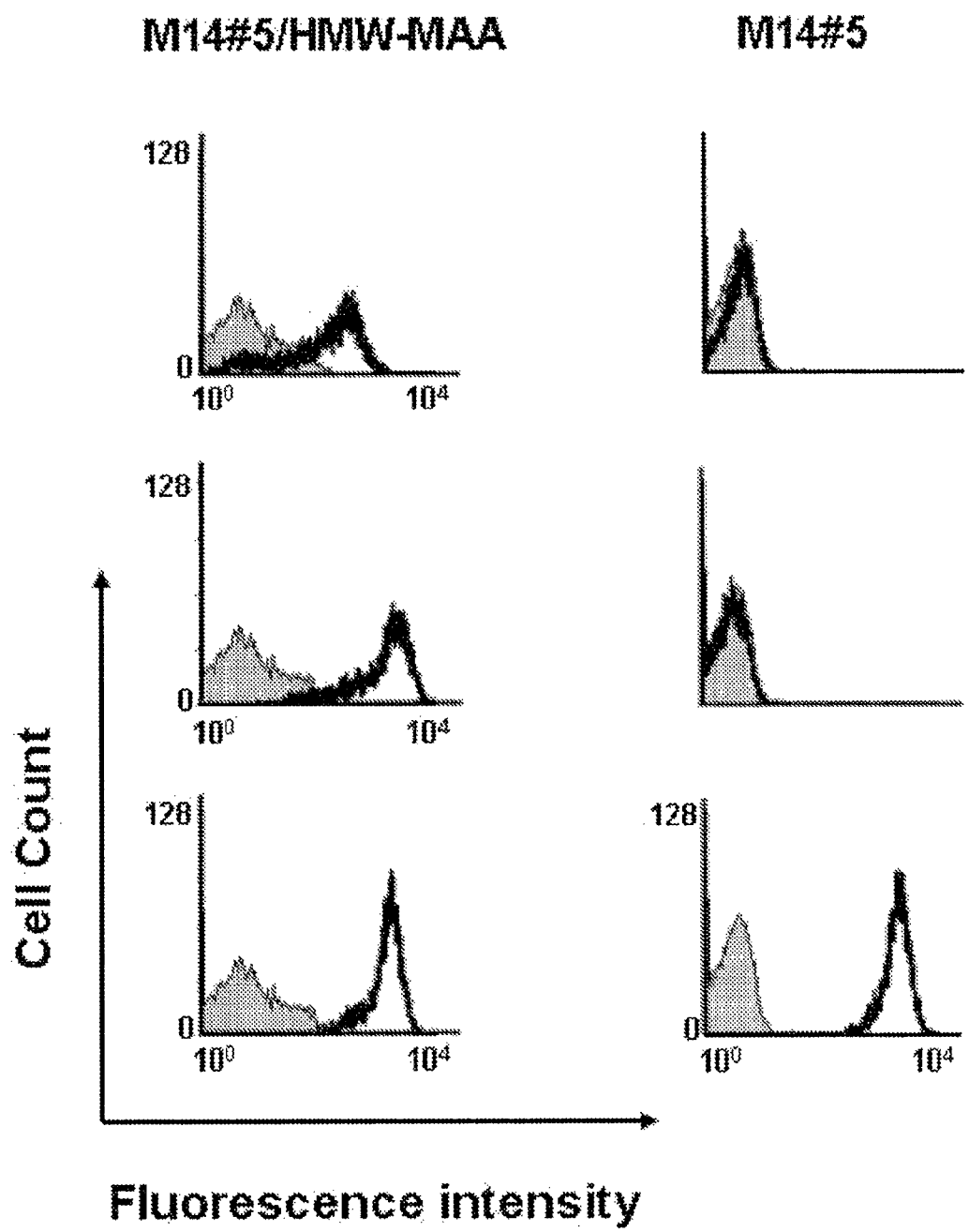
FIG. 2. Flow cytometry analysis of HMW-MAA+ M14#5/HMW-MAA melanoma cells stained with scFv C21. M14#5/HMW-MAA transfectants and parental HMW-MAA− M14#5 cells were incubated on ice with PP scFv C21 and mAb 9E10 (empty histogram) and control PP scFv 119 and mAb 9E10 (grey histogram) (top panel), with HMW-MAA-specific mouse mAb 763.74 (0.5 µg) (empty histogram) and control mAb MK2-23 (grey histogram) (middle panel) and with HLA class I antigen-specific mAb TP25.99 (empty histogram) and control mAb MK2-23 (grey histogram) (bottom panel). Binding of antibodies was detected using RPE-labeled F(ab')2 fragments of goat anti-mouse Ig antibodies. Cells were analyzed with a FACScan™ flow cytometer. Results are expressed as fluorescence intensity.
Figure 3:
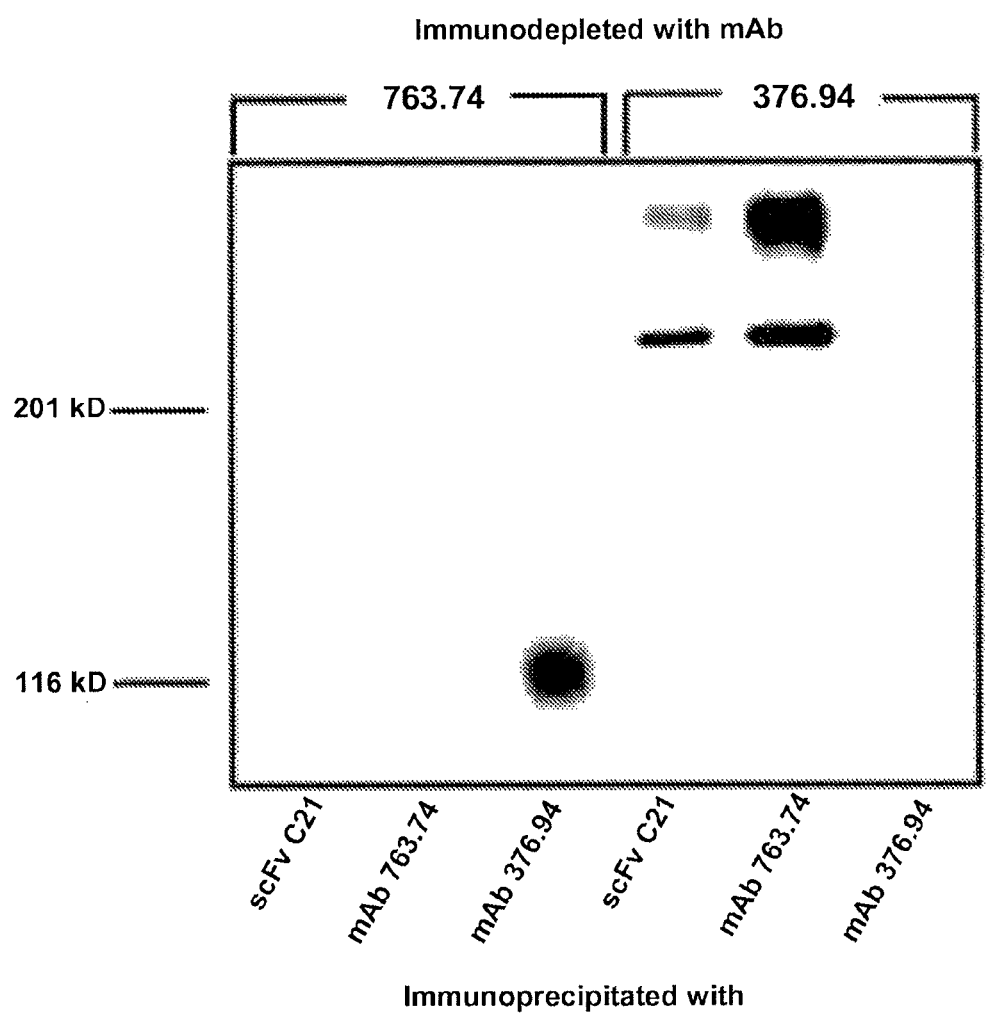
FIG. 3. Structural relationship between molecules recognized by scFv C21 and by HMW-MAA-specific mouse mAb 763.74 in a HMW-MAA+ Colo38 cell lysate. A 1% NP-40 extract of $^{125}$I-labeled Colo38 cells was immunodepleted with mAb 763.74. The immunodepleted cell extract was immunoprecipitated with insolubilized mAb 763.74 and scFv C21. Antigens were eluted and analyzed by SDS-PAGE in an 8% polyacrylamide gel. Gels were fixed, dried and autoradiographed for up to 1 day at −80° C. A 1% NP-40 extract of $^{125}$I-labeled Colo38 cells immunodepleted with 100 kD MAA-specific mouse mAb 376.94 was used as a control.

When tested in ELISA with a panel of human cell lines with differential HMW-MAA expression, and with the rat neural cell line B49, which expresses a HMW-MAA homologue, scFv C21 reacted only with the melanoma cell lines Colo38, FO-1, Melur and SK-MEL-28. All of them express HMW-MAA, suggesting that scFv C21 is specific for HMW-MAA (FIG. 1). This possibility was proven by three lines of evidence. First, flow cytometry analysis showed that scFv C21 stained M14 cells which express HMW-MAA following stable transfection with a plasmid DNA encoding the full length HMW-MAA, but did not stain the parental M14 cells which do not express HMW-MAA (FIG. 2). Second, scFv C21 immunoprecipitated two components with the characteristic elecrophoretic profile of HMW-MAA components from $^{125}$I labeled Colo38 cells. Lastly, in sequential immunoprecipitation experiments, scFv C21 did not immunoprecipitate any components from a Colo38 cell lysate, which had been immunodepleted with the HMW-MAA-specific mouse mAb 763.74. The immunodepletion is specific, since scFv C21 immunoprecipitated the HMW-MAA components from a Colo 38 cell lysate immunodepleted with the 100KD MAA-specific mAb 376.96 (FIG. 3). Conversely, immunodepletion of a Colo38 cell lysate with scFv C21 removed most, but not all the components immunoprecipitated by mAb 763.74. These results reflect the expression of the determinant recognized by scFv C21 on most, but not all the HMW-MAA molecules recognized by mAb 763.74 and/or the lower association constant of scFv C21 than that of mAb 763.74.

Characterization of the Antigenic Determinant Defined by scFv C21

Figure 4:
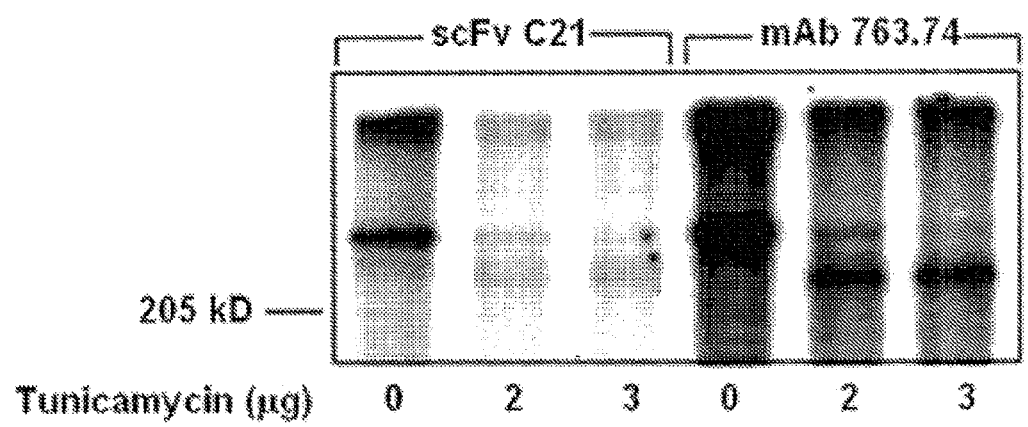
FIG. 4. Role of N-linked glycosylation in the expression of the antigenic determinant recognized by scFv C21 on HMW-MAA isolated from a HMW-MAA+ Colo38 cell extract. A 1% NP-40 extract of Colo38 cells labelled with $^{35}$S-methionine in the presence of tunicamycin (0, 2 and 3 µg/ml,) was immunoprecipitated with scFv C21. Antigens were eluted from the immunoadsorbent and analyzed by SDS-PAGE in an 8% polyacrylamide gel. Gels were fixed, dried and processed for fluorography for up to three days at −80° C. using Hyperfilm-ECL. HMW-MAA-specific mouse mAb 763.74 was used as a control.
Figure 5:
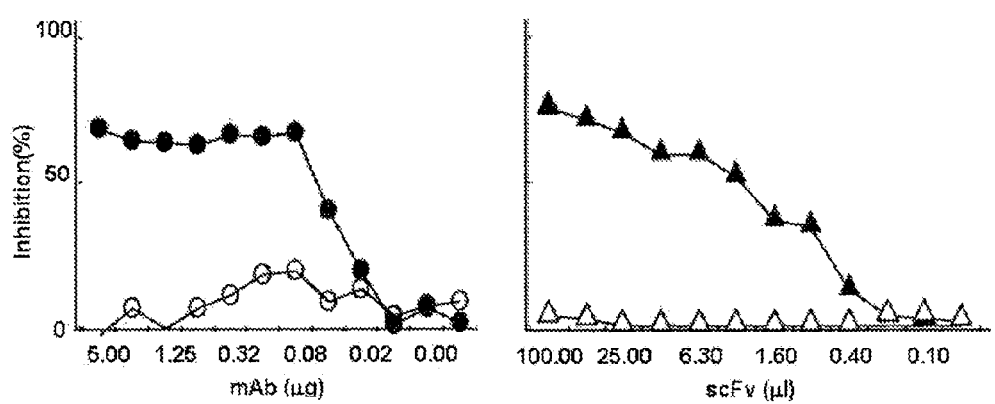
FIG. 5. Spatial proximity of the determinant defined by scFv C21 and of that defined by mouse mAb VF1-TP34 on HMW-MAA+ melanoma cells SK-MEL-28. Varying concentrations of mAb VF1-TP34 (-●-) (left panel) were mixed with biotinylated scFv C21 (0.25 µg/well). The mixture was then transferred to wells containing HMW-MAA+ cells and incubated for 1 h at 4° C. Binding of antibodies was detected using SA-HRP. Results are expressed as % inhibition. Likewise, varying amounts of PP scFv C21 (-▲-) (right panel) were mixed with biotinylated mAb VF1-TP34 (40 ng/well). The mixture was then transferred to wells containing HMW-MAA+ cells and incubated for 1 h at 4° C. The unrelated mAb TP25.99 (-○-) and the unrelated PP scFv 119 (-Δ-) were used as specificity controls.
Figure 6A:
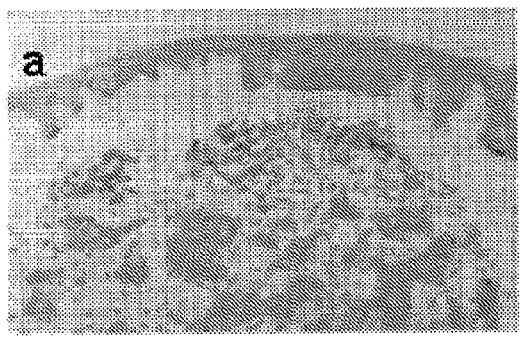
FIGS. 6A-6F. Immunohistochemical staining by scFv C21 of frozen surgically removed human nevi and melanoma lesions. scFv C21 stains a frozen nevus (FIG. 6A), a frozen primary melanoma lesion (FIG. 6B) and a frozen metastatic melanoma lesion (FIG. 6C). The specificity of the staining was monitored by staining the nevus (FIG. 6D), the primary (FIG. 6E) and the metastatic (FIG. 6F) melanoma lesions with the unrelated scFv #119.
Figure 6B:
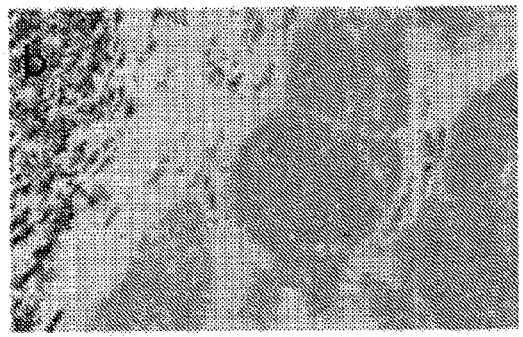
Figure 6C:
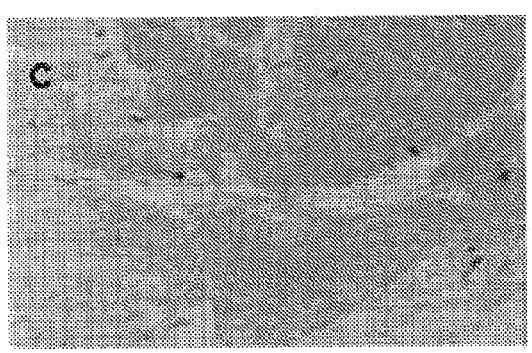
Figure 6D:
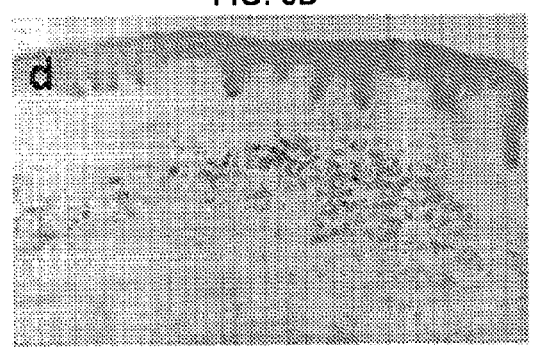
Figure 6E:
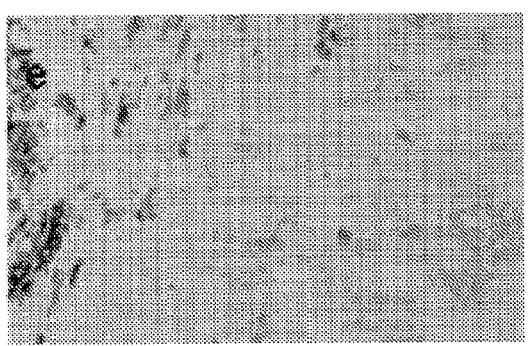
Figure 6F:
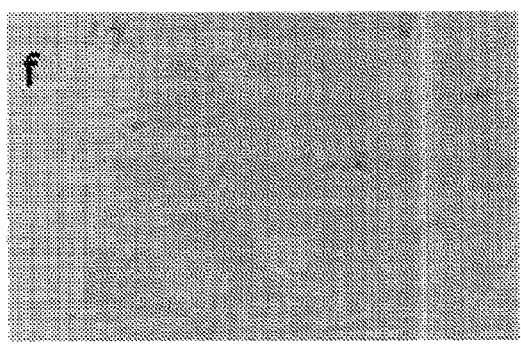

Carbohydrates appear to play a role in the expression of the determinant defined by scFv C21 because of the marked reduction in the intensity of the HMW-MAA components immunoprecipitated from Colo38 cells which had been intrinsically labeled with $^{35}$S-methionine in the presence of the N-glycosylation inhibitor tunicamycin. The inhibition of N-glycosylation is indicated by the accumulation of the 220kD precursor which reacts with mAb 763.74 (FIG. 4). Competition experiments investigated the spatial relationship of the determinants defined by scFv C21 with the 6 determinants defined by a panel of mouse mAb and with those defined by human scFv #28, #61 and #70. scFv C21 and mAb VF1-TP34 partially inhibited each other in their binding to melanoma cells SK-MEL-28. The inhibition is dose dependent (FIG. 5). In contrast, the mouse mAb 149.53, 225.28, 763.74, TP61.5 and VF1-TP41.2 and the scFv #28, #61 and #70 did not inhibit the binding of scFv C21 to SK-MEL-28 cells. These results indicate that the determinant defined by scFv C21 is distinct and spatially close to that defined by mAb VF1-TP34 and is distinct and spatially distant from those defined by the remaining mouse mAb and by the human scFv #28, #61 and #70.

Immunohistochemical Staining of Melanocytic Lesions by scFv C21 scFv C21 stained frozen melanocytic lesions in the immunoperoxidase reaction, but did not stain formalin fixed paraffin embedded melanocytic lesions. The staining was both membranous and cytoplasmic (FIG. 6). Comparison of the staining patterns of benign and malignant melanocytic lesions with scFv C21 and HMW-MAA-specific mouse mAb 763.74 showed that both antibodies stain homogeneously 4 pigmented nevi with a membranous and a cytoplasmic pattern. Furthermore, mAb 763.74 stained 14 out of 15 primary lesions with a homogeneous pattern, while scFv C21 stained 9 with a homogenous pattern and 2 with a heterogeneous pattern. The staining was membranous in 1 lesion, membranous and cytoplasmic in 4 and cytoplasmic in 6. Lastly, mAb 763.74 stained 6 metastatic lesions with a homogeneous pattern, while scFv C21 stained 3 with a homogeneous pattern and 3 with a heterogeneous pattern. The staining was membranous and cytoplasmic in 3 lesions and cytoplasmic in the remaining 3.

Example 3

Nucleotide and Amino Acid Sequences of scFv C21

The nucleotide and amino acid sequences of scFv C21 were determined according to standard methods. The nucleotide and amino acid sequences of the $V_H$, $V_L$ and linker are provided below. Also provided is the nucleotide sequence of the immunoglobulin heavy chain hinge, CH2 and CH3 domains.

```
Nucleotide sequences
V_H
                                             (SEQ ID NO: 1)
ATGCAGGTGCAGCTGGTGCAGTCTGGGGCTGAGGTGAAGAAGCCTGGGT

CCTCGGTGAAGGTCTCTGCAAGGCTTCTGGAGGCACCTTCAGCAGCTAT

GCTATCAGCTGGGTGCGACAGGCCCCTGGACAAGGGCTTGAGTGGATGG

GAGGGATCATCCCTATCTTTGGTACAGCAAACTACGCACAGAAGTTCCA

GGGCAGAGTCACGATTACCGCGGACGAATCCACGAGCACAGCCTACATG

GAGCTGAGCAGCCTGCGATCTGACGACACGGCCGTGTATTACTGTGCAA

GGGCCCTTGATCCTATTACGTTTGACTCCTGGGGCCAAGGTACCCTGGT

CACCGTCTCGAGA

Linker
                                             (SEQ ID NO: 2)
GGTGGAGGCGGTTCAGGCGGAGGTGGCTCTGGCGGTGGCGGATCG V_L
                                             (SEQ ID NO: 3)
TCTGAGCTGACTCAGGACCCTGCTGTGTCTGTGGCCTTGGGACAGACAG

TCAGGATCACATGCCAAGGAGACAGCCTCAGAAGCTATTATGCAAGCTG

GTACCAGCAGAAGCCAGGACAGGCCCCTGTACTTGTCATCTATGGTAAA

AACAACCGGCCCTCAGGGATCCCAGACCGATTCTCTGGCTCCAGCTCAG

GAAACACAGCTTCCTTGACCATCACTGGGGCTCAGGCGGAAGATGAGGC

TGACTATTACTGTAACTCCCGGGACAGCAGTGGTAACCATGTGGTATTC

GGCGGAGGGACCAAGCTGACCGTCCTAGGTAGATCT

Heavy Chain (Hc) Hinge + CH2 + CH3
                                             (SEQ ID NO: 4)
GAGCCCAAATCTTGTGACAAAACTCACACATGCCCACCGTGCCCAGCAC

CTGAACTCCTGGGGGGACCGTCAGTCTTCCTCTTCCCCCCAAAACCCAA

GGACACCCTCATGATCTCCCGGACCCCTGAGGTCACATGCGTGGTGGTG

GACGTGAGCCACGAAGACCCTGAGGTCAAGTTCAACTGGTACGTGGACG

GCGTGGAGGTGCATAATGCCAAGACAAAGCCGCGGGAGGAGCAGTACAA

CAGCACGTACCGTGTGGTCAGCGTCCTCACCGTCCTGCACCAGGACTGG

CTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACC

ACAGGTGTACACCCTGCCCCCATCCCGGGATGAGCTGACCAAGAACCAG

GTCAGCCTGACCTGCCTGGTCAAAGGCTTCTATCCCAGCGACATCGCCG

TGGAGTGGGAGAGCAATGGGCAGCCGGAGAACAACTACAAGACCACGCC

TCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGA

TGCATGAGGCTCTGCACAACCACTACACGCAGAAGAGCCTCTCCCTGTC

TCCGGGCAAATGA

Amino acid sequences
V_H
                                             (SEQ ID NO: 5)
QVQLVQSGAEVKKPGSSVKVSCKASGGTFSSYAISWVRQAPGQGLEWMG
GIIPIFGTANYAQKFQGRVTITADESTSTAYMELSSLRSDDTAVYYCAR
ALDPITFDSWGQGTLVTVSR (118 amino acids)

V_L
                                             (SEQ ID NO: 6)
SELTQDPAVSVALGQTVRITCQGDSLRSYYASWYQQKPGQAPVLVIYGK
NNRPSGIPDRFSGSSSGNTASLTITGAQAEDEADYYCNSRDSSGNHVVF
GGGTKLTVLGRS (110 amino acids)
```

For both V$_H$ (SEQ ID NO: 5) and V$_L$ (SEQ ID NO: 6), the location of the framework regions (FR) and CDRs is as follows:

FR1—amino acids 1-26
CDR1—amino acids 27-38
FR2—amino acids 39-55
CDR2—amino acids 56-65
FR3—amino acids 66-104
CDR3—amino acids 105-115 (V$_H$) or 105-110 (V$_L$)

Example 4

Identification and Characterization of scFv Peptide Mimics

Sequence of Peptides Binding to scFv C21 Isolated from Phage Display Peptide Libraries LX-8 and X15

Immunological screening revealed that scFv C21 reacted strongly with 20% of the clones isolated by panning from the phage display peptide X15 library, but reacted with none of those isolated from the LX-8 library. The phage supernatants of positive clones obtained from immunoscreening reacted with scFv C21 also in ELISA. The reactivity is specific, since the clones did not react with scFv F98 and W34 which recognize unrelated MAA. Nucleotide sequence analysis of 16 of the clones reacting with scFv C21 identified the sequences SPSWYCPDCDKRPLV (P1C21) (SEQ ID NO: 7), EARNWHDFPIHPRTL (P2C21) (SEQ ID NO: 8) and RPYRYDPLGDLKSRH (P3C21) (SEQ ID NO: 10) in 88, 6 and 6%, respectively, of the 16 clones analyzed. The sequences of peptides P1C21 and P3C21 share the consensus PXXYXPXXD (SEQ ID NO: 9), while that of peptide P2C21 is completely different. Consistent with the carbohydrate nature of the determinant recognized by scFv C21, no homology was found between the sequences of the three peptides isolated from the phage display peptide libraries and the published amino acid sequence of the HMW-MAA core protein (Pluschke et al., *Proc Natl Acad Sci USA* 93:9710-9715, 1996).

Analysis of the Reactivity of Synthetic Peptides with scFv C21

Figure 7:
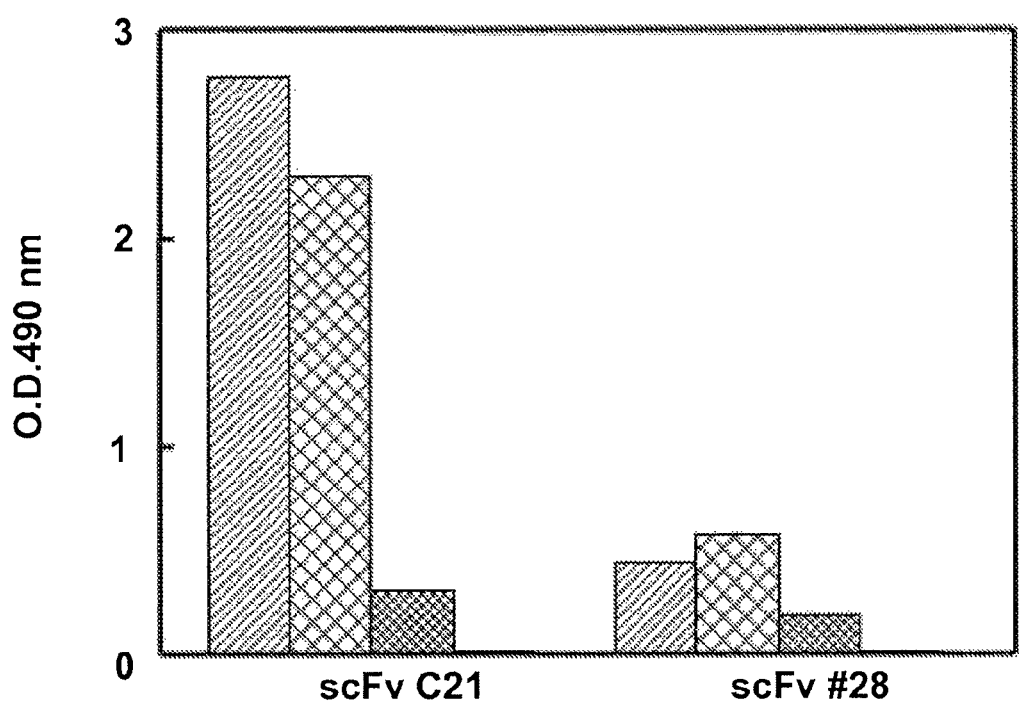
FIG. 7. Reactivity in ELISA of scFv C21 with synthetic peptides derived from those isolated by panning the phage display peptide library X15 with scFv C21. Ninety-six well plates were coated for 2 h at 37° C. with synthetic peptides P1C21 (▨), P2C21 (125 µM) (▨), and P3C21 (125 µM) (▨), in 0.25% glutaradehyde-PBS. Following blocking with PBS-1% BSA, wells were incubated for 2 h at room temperature with 50 µl of PP scFv C21 at and 50 µl of biotinylated mAb 9E10 (2.5 µg/ml 1% BSA-PBS). Binding of scFv antibody to ■ peptides was detected by addition of SA-HRP. Results are expressed as absorbance at 490 µM. The human scFv #28 which recognizes an unrelated HMW-MAA determinant and the unrelated peptide MART-1 (AA-GIGILTV; SEQ ID NO: 16) (■) were used as specificity controls.
Figure 8:
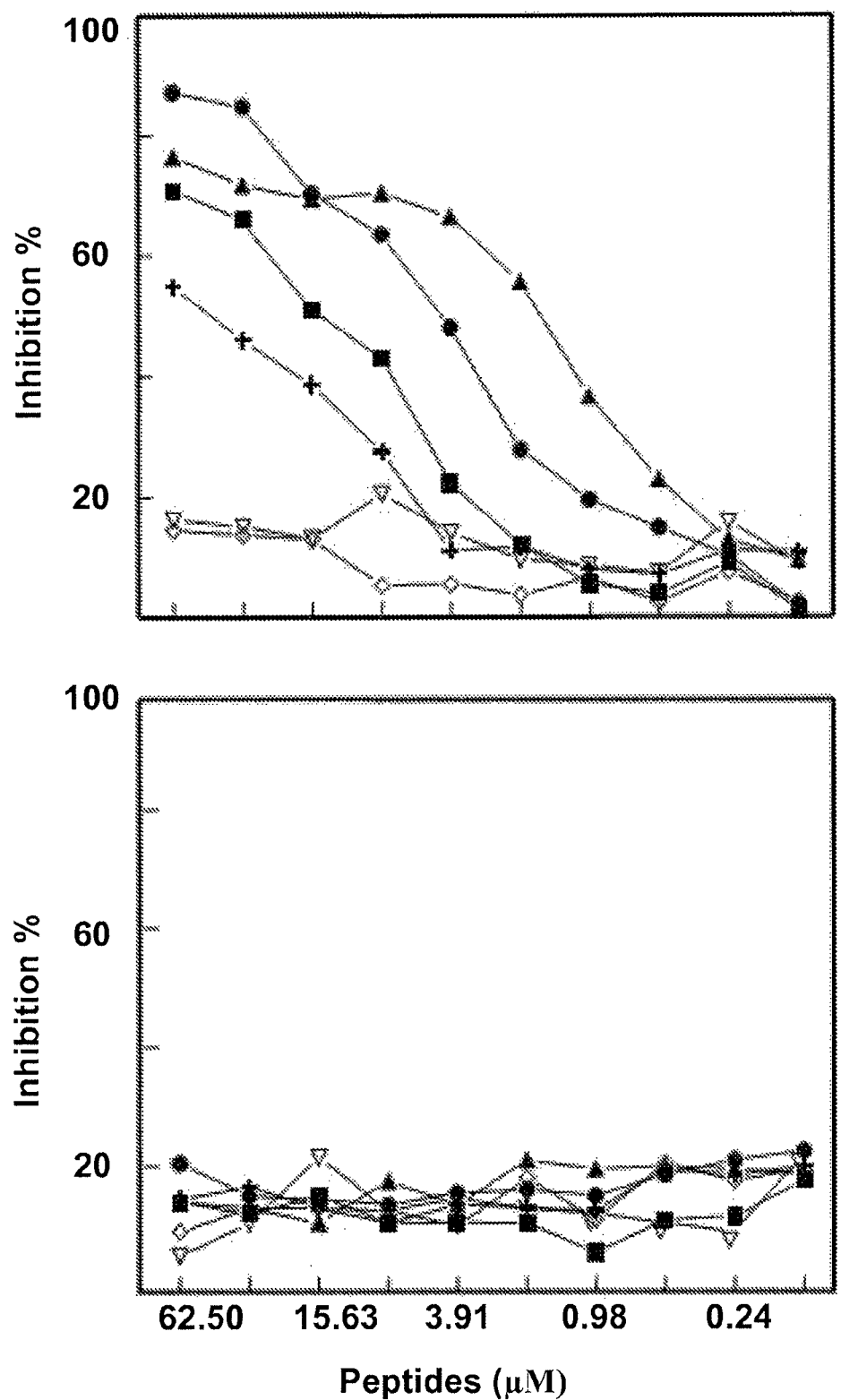
FIG. 8. Inhibition of the reactivity of scFv C21 with HMW-MAA+ cells Colo38 by synthetic peptides P1C21 and P3C21 and by modified peptide P3C21. Varying concentrations of synthetic peptides P1C21 (-●-), P3C21(-▲-), P3A5 (-◇-), P3V7 (—+—) and P3S10 (—■—) were incubated for 2 h at 4° C. with 50 µl of PP scFv (1:1600 dilution in 1% BSA-PBS) and 50 µl of biotinylated mAb 9E10 (2.5 µg/ml 1% BSA-PBS). The mixture was then transferred to wells containing cells Colo38. Binding of scFvC21 was detected using SA-HRP (top panel). Results are expressed as % inhibition. The unrelated peptide MART-1 (-▽-) and the scFv #28 (bottom panel) which recognizes an unrelated HMW-MAA determinant were used as specificity controls.

To corroborate the reactivity of phage display peptides with scFv C21, peptides P1C21 (cyclized), P2C21 (linear), and P3C21 (linear), were synthesized and tested for their ability to react in ELISA with scFv C21 and to inhibit its binding to HMW-MAA$^+$ melanoma cells Colo38 in an inhibition assay. The synthetic peptide P1C21 and P2C21, immobilized on a microtiter plate by 0.25% glutaraldehyde PBS, reacted specifically with scFv C21 in ELISA while immobilized synthetic peptide P3C21 did not (FIG. 7). The binding is specific, since no peptides reacted with the unrelated HMW-MAA-specific scFv #28. Moreover, the peptides P1C21 and P3C21 inhibited the binding of scFv C21 to HMW-MAA$^+$ cells in a dose dependent fashion (FIG. 8). The inhibition is specific since both peptides did not inhibit the binding of scFv #28 to melanoma cells Colo38 (FIG. 8). In contrast, P2C21 did not inhibit the binding of scFv C21 to melanoma cells Colo38. The inhibition of the binding of scFv C21 to melanoma cells by soluble peptide P3C21 and the lack of reactivity of immobilized peptide P3C21 with scFv C21 suggest that the binding of this peptide with scFv C21 is conformationally sensitive.

Figure 9:
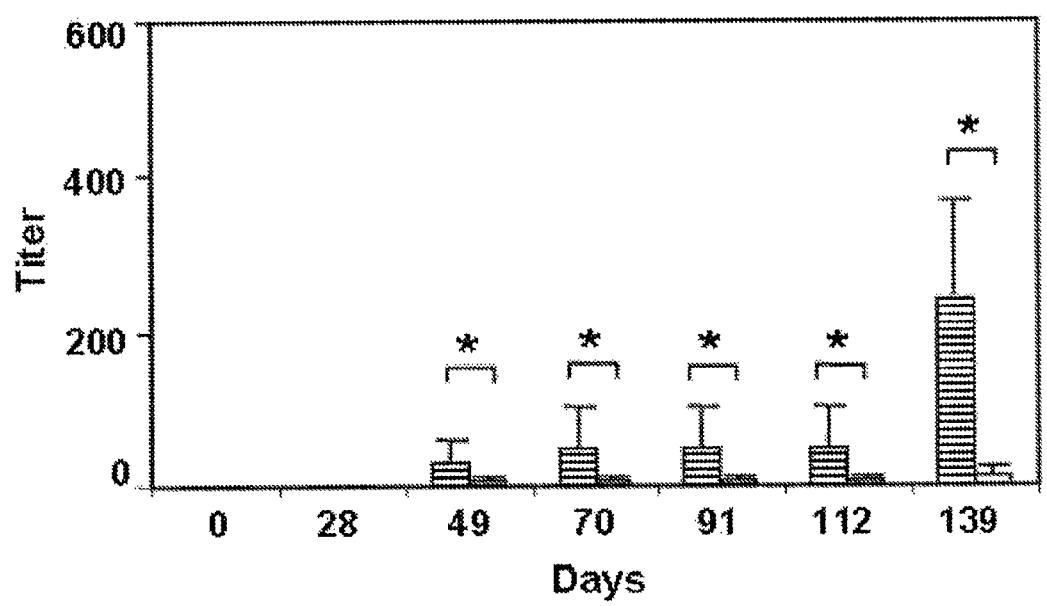
FIG. 9. Development of antibodies with selective reactivity with HMW-MAA+ cells Colo38 in BALB/c mice immunized with peptide P1C21 and boosted with Colo 38 cells. Mice were immunized with KLH-conjugated peptide P1C21 (■) (50 µg/injection) on day 0, 21, 42, 63, 84 and 105, and with HMW-MAA+ Colo38 melanoma cells (5×10$^5$ cells/injection) on day 132. Sera were harvested one week before the first immunization, and one week after each immunization. Two-fold dilutions of sera (100 µl/well) were incubated with HMW-MAA+ Colo38 melanoma cells (1×10$^5$/well). Following an additional incubation with HRP-conjugated goat anti-mouse IgG antibodies, the reaction was developed using TMB substrate. O.D. was measured at 450 nm. Results are expressed as the mean±SD of the highest dilution of sera giving 50% of the maximal binding to HMW-MAA$^+$ cells. Sera from mice immunized with peptide MB1$_{194-208}$ were used as controls. *p<0.05.

Induction of HMW-MAA-Specific Humoral and Cellular Immunity by Peptide P1C21 in BALB/c Mice To further prove the HMW-MAA mimicry by peptide P1C21, its ability to elicit HMW-MAA-specific humoral and cellular immunity in BALB/c mice was tested. Antibodies selectively reacting with HMW-MAA$^+$ melanoma cells Colo38 were detected in sera harvested from BALB/c mice one week following the third immunization with the peptide P1C21. The mean titer of these antibodies was low, although significantly (p<0.05) higher than that of the antibodies in sera from mice immunized with the unrelated MB1$_{194-208}$ peptide. Furthermore, the titer of the antibodies reacting with melanoma cells did not change following three additional boosters. However the titer of the antibodies selectively reacting with HMW-MAA$^+$ melanoma cells was markedly enhanced by boosting the mice immunized with peptide P1C21 with HMW-MAA$^+$ melanoma cells (FIG. 9).

Figure 10:
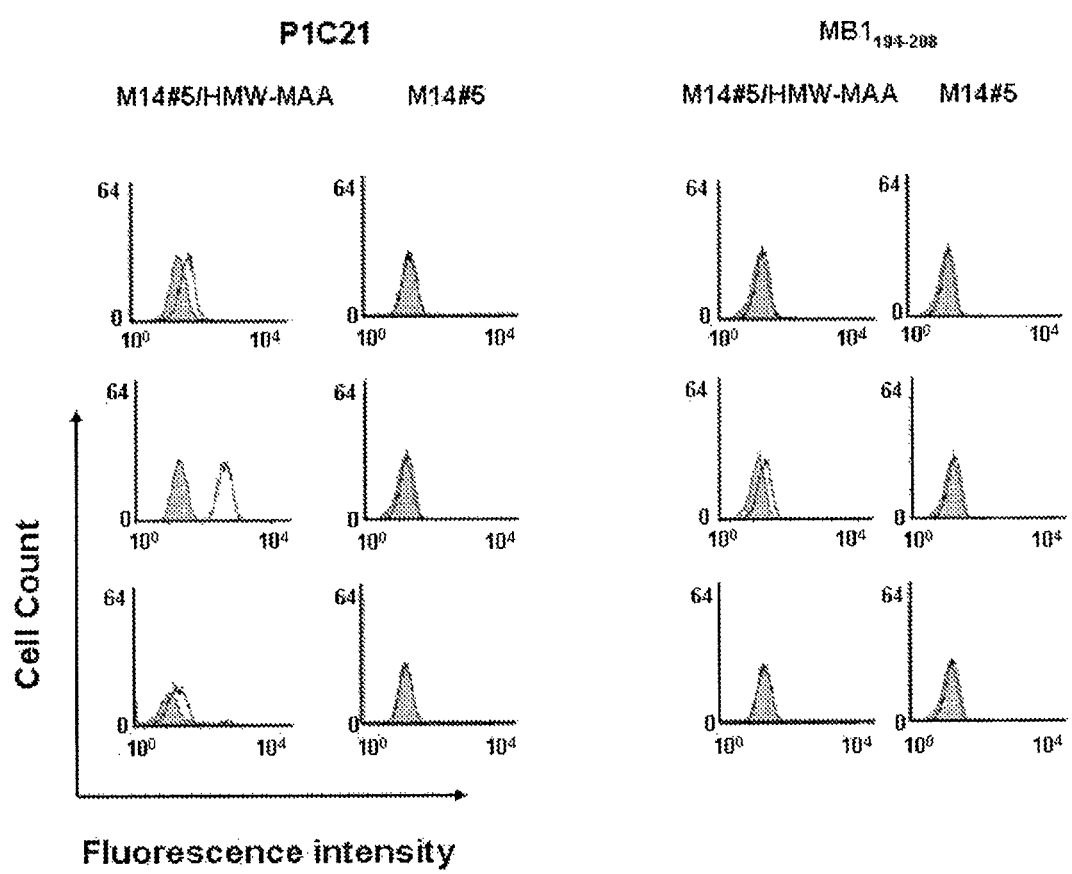
FIG. 10. Flow cytometry analysis of HMW-MAA$^+$ M14#5/HMW-MAA melanoma cells stained with antibodies elicited by peptide P1C21 and HMW-MAA$^+$ cells Colo38 in BALB/c mice. M14#5/HMW-MAA transfectants and parental HMW-MAA$^-$ M14#5 cells were incubated on ice with 100 µl of sera (1:60 dilution) from mice immunized with peptide P1C21 (top panel), and with sera from mice immunized with peptide P1C21 or control peptide MB1$_{194-208}$ and boosted with HMW-MAA$^+$ cells Colo38 (middle panel). Following washing, cells were incubated on ice with RPE-labeled F(ab')$_2$ fragments of goat anti-mouse Ig antibodies. Cells were then analyzed with a FACScan™ flow cytometry. Results are expressed as fluorescence intensity (empty histogram). Preimmune sera (grey histogram), sera from mice immunized with control peptide MB1$_{194-208}$ (top panel), sera from mice immunized with peptide MB1$_{194-208}$ and boosted with HMW-MAA$^+$ melanoma cells Colo38 (middle panel) and sera from mice immunized with peptide P1C21 or peptide MB1$_{194-208}$ and boosted with HMW-MAA$^-$ lymphoid cells LG2 (bottom panel) were used as controls.
Figure 11:
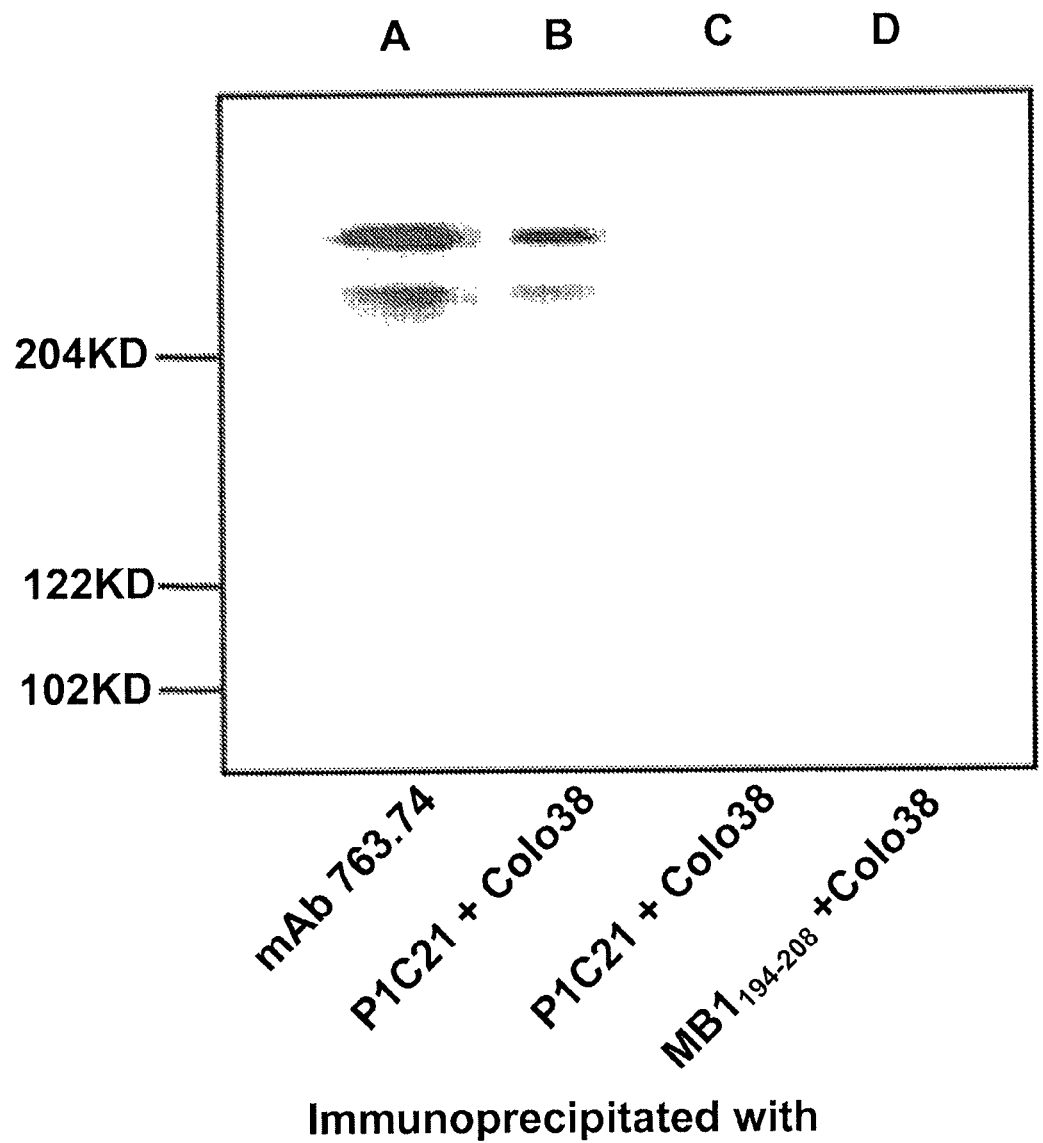
FIG. 11. Immunochemical characterization of the HMW-MAA specificity of sera from mice immunized with peptide P1C21 and boosted with HMW-MAA$^+$ cells Colo38. A 1% Triton X-100 extract of $^{125}$I-labeled Colo38 melanoma cells was immunoprecipitated with sera from mice sequentially immunized with peptide P1C21 and with HMW-MAA$^+$ cells Colo38 (lane B). Antigens were eluted from the immunoadsorbent, and analyzed by SDS-PAGE in an 8% polyacrylamide gel. Gels were fixed, dried and autoradiographed for 2 days at −80° C. HMW-MAA-specific mouse mAb 763.74 (lane A), sera from mice immunized with peptide P1C21 and boosted with HMW-MAA$^-$ lymphoid cells LG2 (lane C) and sera from mice immunized with control peptide MB1$_{194-208}$ and boosted with HMW-MAA$^+$ Colo38 melanoma cells lane (lane D) were used as controls.

Two lines of evidence proved the HMW-MAA specificity of the elicited antibodies. First, the immune sera stained M14#5/HMW-MAA cells that express HMW-MAA following transfection with a plasmid DNA encoding the full length HMW-MAA, but did not stain the parental M14#5 cells (FIG. 10). The latter cells do not express HMW-MAA. In contrast, sera from mice immunized with peptide MB1$_{194-208}$ displayed no reactivity with Colo38 cells, although they highly reacted with the immunizing peptide. Second, SDS-PAGE analysis showed that sera from mice sequentially immunized with peptide P1C21 and Colo38 cells immunoprecipitated the characteristic HMW-MAA components from a Colo38 cell lysate. The specificity of the immune response elicited by the prime-boost strategy with peptide P1C21 and HMW-MAA$^+$ cells Colo38 is indicated by the lack of selective reactivity with HMW-MAA$^+$ cells Colo38 of sera from BALB/c mice immunized (i) with peptide P1C21 and HMW-MAA-lymphoid cells LG2 or (ii) with peptide MB1$_{194-208}$ and HMW-MAA$^+$ cells Colo38, both in binding assays and in immunoprecipitation experiments (FIG. 11).

Figure 12:
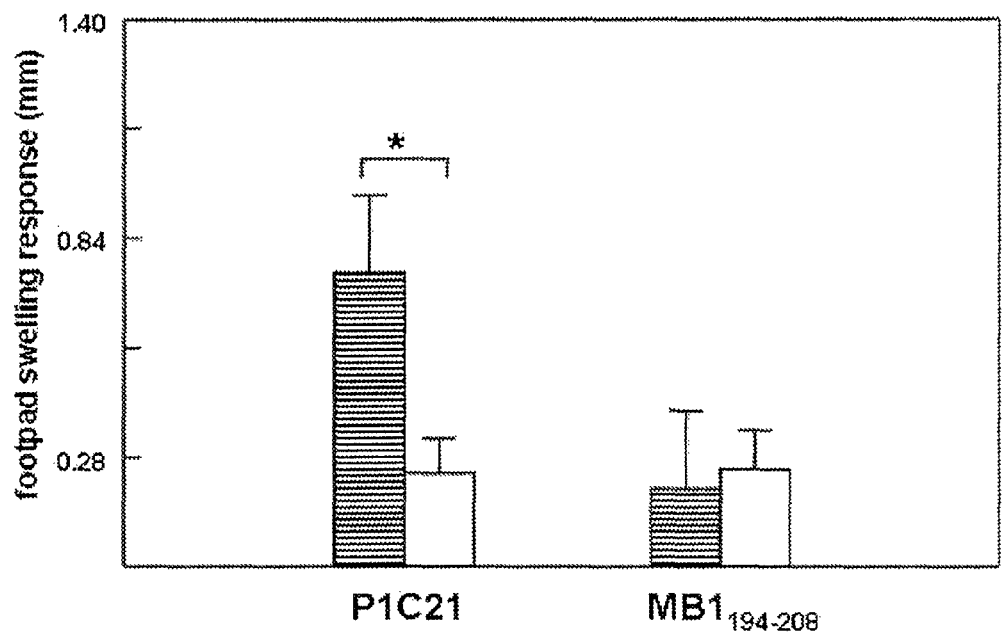
FIG. 12. DTH reaction to HMW-MAA$^+$ melanoma cells Colo38 in BALB/c mice immunized with peptide P1C21. Irradiated (20K rads) HMW-MAA$^+$ cells Colo38 (5×10$^5$ cells/mouse) (■) and HMW-MAA$^-$ LG2 cells (5×10$^5$ cells/mouse) (□) were injected on day 132 into the right and left hind footpad, respectively, of BALB/c mice, which had been immunized six times with peptide P1C21 on days 0, 21, 42, 63, 84 and 105. Amount of swelling induced by the injected cells was measured and calculated by subtracting the thickness of the footpad measured at time 0 h from that measured 24 h after the injection of cells. Mice immunized with control peptide MB1$_{194-208}$ using the same schedule were injected at the same time point with either Colo38 or LG2 cells, and used as controls. *p<0.05.

Immunization of BALB/c mice with peptide P1C21 elicited a DTH response to HMW-MAA$^+$ cells Colo38 as indicated by the significantly (p<0.05) higher swelling of the footpad injected with Colo38 cells than of that injected with LG2 cells. The swelling persisted for 48 hours. The DTH response to HMW-MAA$^+$ melanoma cells induced by peptide P1C21 is specific, since no swelling of the footpad was observed in mice that had been immunized with the unrelated MB1$_{194-208}$ peptide and challenged with Colo38 cells (FIG. 12).

Structural Basis of Peptides P1C21 and P3C21 Binding to scFv C21

To define the structural basis for the binding of the peptides P1C21 and P3C21 to scFv C21, a molecular model of scFv C21 and its complex with the two peptides was built. Starting models of the peptides P1C21 and P3C21 were built using the limited conformational search algorithm in INSIGHTII. The initial orientation of peptide binding to scFv C21 was determined by DOCK analysis. The best orientation was selected based on the contact score, as well as on the binding energy, and then minimized using INSIGHTII for optimal binding and interaction analysis (Table 1). During the minimization, scFv C21 was held fixed for the first 2000 cycles. Subsequently, CDR loops and peptides were allowed to move.

TABLE 1

Intermolecular contacts of peptides P1C21 and P3C21 with scFv C21 and calculated binding energy of the respective complexes.

| Ligand | scFv C21 contacts | Total Energy (Kcal/mol) |
| --- | --- | --- |
| P1C21 (Ser2) | H30, H31, H100 | −93.8 |
| P1C21 (Pro 7) | L92 | |

TABLE 1-continued

Intermolecular contacts of peptides P1C21 and P3C21 with scFv C21 and calculated binding energy of the respective complexes.

| Ligand | scFv C21 contacts | Total Energy (Kcal/mol) |
|---|---|---|
| P1C21 (Asp 8) | L91, L30 | |
| P1C21 (Lys 11) | H51, H57, H58 | |
| P1C21 (Arg 12) | H32, H98, H99, H101 | |
| P1C21 (Pro 13) | H53, H54 | |
| P1C21 (Leu 14) | H29 | |
| P3C21(Pro 2) | H28, H53 | −7.3 |
| P3C21(Tyr 3) | H30 | |
| P3C21(Arg 4) | H26, H27, H31 | |
| P3C21(Tyr 5) | H29 | |
| P3C21(Pro 7) | H99, H100 | |
| P3C21(Leu 11) | L30, L48 | |
| P3C21(Lys 12) | L50, L51 | |
| P3C21(Arg 14) | L29, L49, L64, L66 | |
| P3S10(Pro 2) | H28, H53 | −16.4 |
| P3S10(Tyr 3) | H30 | |
| P3S10(Arg 4) | H26, H27, H31 | |
| P3S10(Tyr 5) | H29 | |
| P3S10(Pro 7) | H99 | |
| P3S10(Leu 8) | H100 | |
| P3S10(Ser 10) | L47 | |
| P3S10(Leu 11) | L30, L48, L89 | |
| P3S10(Lys 12) | L50, L51 | |
| P3S10(Arg 14) | L29, L49, L64, L66 | |

Molecular modeling of the binding mode conformations of the peptides P1C21 and P3C21 indicates that the peptides can interact with different functional groups within the antigen-combining site of scFv C21. Substitution of 10Ser for 10Asp is suggested to improve the binding of the linear peptide form. Residues shown in bold are extra favorable contacts due to 10Asp to 10Ser mutation.

Figure 13:
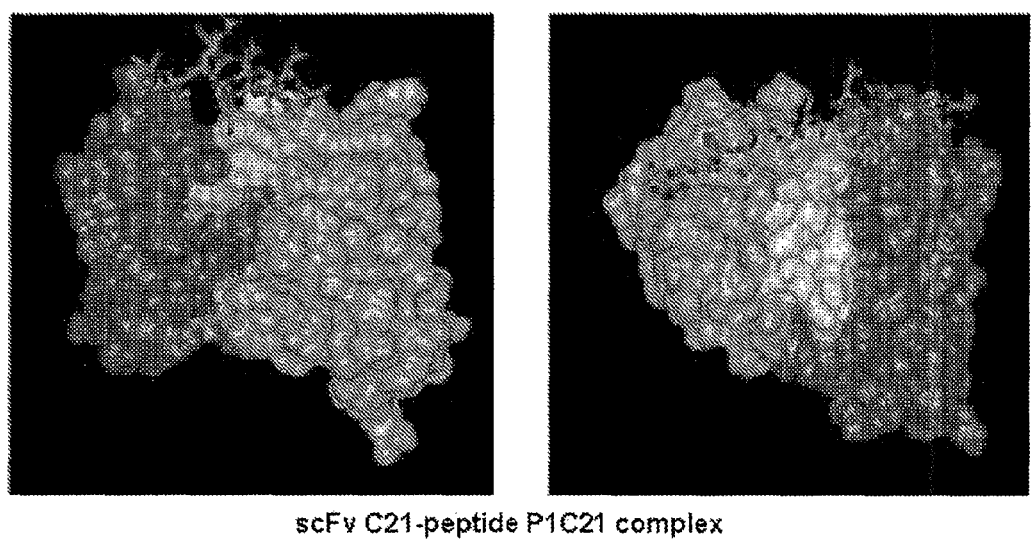
FIG. 13. Molecular model of scFv C21-P1C21 and -P3C21 peptide complex. V$_H$ and V$_L$ of scFv C21 are shown. The HCDR3 and LCDR3, which adopt non-canonical structures, are also shown in. Binding of the cyclic P1C21 peptide is shown in the left panel. The binding energy is −93.8 Kcal/mol. The residues 7Pro, 5Tyr and 4Trp define the specificity. The binding of linear P3C21 to scFv C21 is shown in the right panel. The binding energy is −7.3 Kcal/mol. The P3C21 peptide adopts a more extended structure in the binding mode. The critical contacts were observed between H1 and H3 through 4Arg, 7Pro and 5Tyr. One of the conserved residues (10Asp) is solvent exposed, but proximal leucines buried in a hydrophobic pocket facilitate a stable complex.

The primary sequences of the peptides P1C21 and P3C21 are 50% homologous. 5Tyr, 7Pro and 10Asp are conserved in both sequences at the core. In the molecular modeling, both peptides interact with scFv C21 through conserved residues, but in two orientations (Table 1 and FIG. 13). The peptide P1C21 adopts a folded structure and binds across the heavy and light chain CDR3 of scFv C21, while the peptide P3C21 binds across all the CDR loops in an extended conformation. P1C21 is a cyclic peptide and its folded structure makes several favorable interactions with scFv C21 and also forms a more stable complex (Table 1), due to Trp at position 4 which docks into a hydrophobic pocket formed by heavy chain CDR2 and CDR3 and by light chain CDR2. The linear peptide P3C21, on the other hand, forms a stable complex with fewer contacts through Tyr and mostly hydrophobic interactions mediated by Pro. The conserved 10Asp is not involved in any contacts.

Effect of Amino Acid Substitutions on the Reactivity of Peptide P3C21 with scFv C21

To further characterize effects associated with possible conformational transitions and potential contact residues, amino acid substitutions were introduced into the linear peptide P3C21 based on the molecular modeling studies. The effect of select substitutions on the reactivity of the peptide P3C21 with scFv C21 was tested experimentally by Biacore (Table 2) and inhibition analysis (FIG. 8).

TABLE 2

Kinetic binding analysis of peptide P1C21 and P3C21 binding to scFv C21

| Peptide | $K_{on}$ (1/Ms) | $K_{off}$ (1/s) | Kd (M) |
|---|---|---|---|
| P1C21 SPSWYCPDCDKRPLV (SEQ ID NO: 7) | 1.183e3 | 9.7e−3 | 8.24e−6 |
| P3C21 RPYRYDPLGDLKSRH (SEQ ID NO: 10) | 2.17e3 | 6.55e−2 | 3.02e−5 |
| P3A5 RPYRADPLGDLKSRH (SEQ ID NO: 11) | No detectable binding observed | | |
| P3V7 RPYRYDVLGDLKSRH (SEQ ID NO: 12) | No detectable binding observed | | |
| P3S10 RPYRYDPLGSLKSRH (SEQ ID NO: 13) | 9.17e2 | 3.07e−3 | 3.34e−6 |

To evaluate binding, peptides P1C21 and P3C21 were injected at concentrations ranging from 1 to 32 μM. The resulting sensograms were used for estimation of the kinetic constants ($k_{on}$ and $k_{off}$) by global fitting to the 1:1 Langmurian interaction model. The binding constant ($K_d$) was calculated for each peptide as a $k_{off}/k_{on}$ ratio.

In the scFv C21-P3C21 complex, the interaction of 5Tyr (to H29) was critical to keep the 7Pro anchored to the hydrophobic pocket, suggesting that substitutions at these two critical positions would abrogate scFv C21 binding. Biacore analysis of the interactions between the peptides and the immobilized scFv C21 was performed to test the effect of the introduced modifications in the peptide sequences on their binding properties (Table 2). Good fitting of the experimental data to the calculated curves was observed, suggesting a simple pseudo-first order interaction between the peptides and scFv C21. Substituted residues at positions 5Tyr and 7Pro indeed abrogated peptide binding to scFv C21 (Table 2).

In contrast to positions 5Tyr and 7Pro, 10Asp was not involved in any contacts with scFv C21. However, during the simulation we noticed that the LGDL sequence tract was highly mobile, whereas 10Asp made frequent contact (L89 Arg) with the scFv C21 binding site but this orientation resulted in both Leu residues being exposed. Since exposed hydrophobic residue orientation is not energetically suitable, we chose the exposed 10Asp conformation as one of the most favorable binding modes for further minimization, but introduced a Ser residue at position 10. In contrast to Asp, the Ser substituted peptide makes a contact with Tyr at 49Leu of scFv C21 without much change in the Leu orientation. Intermolecular interaction analysis suggested that this Ser substituted peptide would bind more effectively with scFv C21 (Table 1). This possibility was also corroborated by Biacore analysis of the interaction of substituted peptides with scFv C21 (Table 2). Replacement of Asp with Ser at position 10 (P3S10) had only a slight effect on the ability of P3C21 to inhibit the reactivity of scFv C21 with Colo38 cells (FIG. 8). This finding suggests that at position 10, a polar substitution is tolerated. The reduced inhibition may be due to the complex nature of HWM-MAA-scFv C21-peptide interactions.

Example 5

HMW-MAA-Specific Monoclonal Antibodies for the Treatment of Cancer

This example describes the use of HMW-MAA-specific human monoclonal antibodies for the treatment of cancers that exhibit overexpression of HMW-MAA (referred to herein as a "HMW-MAA-positive" cancer), including, but not limited to melanoma, breast cancer, prostate cancer and squamous cell carcinoma. Patients diagnosed with a HMW-MAA-positive cancer can be treated according to standard procedures in the art. Generally, treatment options include surgery, radiation therapy, chemotherapy, immunotherapy or interferon therapy.

In this example, patients diagnosed with a HMW-MAA-positive melanoma are administered an immunoconjugate comprising a HMW-MAA-specific human monoclonal antibody linked to *Pseudomonas* exotoxin (PE). Preparation of PE immunoconjugates has been described (see, for example, U.S. Pat. No. 7,081,518 and U.S. Pre-Grant Publication No. 2005/0214304, which are herein incorporated by reference). In some patients, the immunoconjugate is administered by intravenous bolus injection every other day for a total of three to six doses. In other patients, the immunoconjugate is administered by continuous intravenous infusion over the course of ten days. The dose of immunoconjugate administered to a patient varies depending on the weight and gender of the patient, and mode and time course of administration. Following treatment, patients are evaluated for cancer progression (including tumor growth and metastasis) and other clinical signs of illness. Patients can be treated with the immunoconjugate alone, or in combination with one or more standard cancer treatments. For example, a patient that has undergone surgery to remove the melanoma can subsequently be treated with the immunoconjugate.

Example 6

Additional Materials and Methods

Mice: Female SCID/BALB/c mice (C.B-Igh-1$^b$IcrTac-Prkdcscid, 6-8 weeks old) were purchased from NCI or Taconic Farms, Inc. Experiments for this study were approved by the Institutional Animal Care and Use Committee.

Cell lines: The human tumor cell lines were maintained in RPMI 1640 medium supplemented with 10% FCS.

Antibodies: scFv-Fc C21 and scFv-Fc 119, which was used as an isotype control were purified from mouse ascites by sequential ammonium sulphate and caprylic acid precipitation and Protein A column. PE-anti-human IgG antibodies was purchased from Jackson ImmunoResearch Laboratories, Inc. Specific antibodies for signaling molecules were purchased commercially for: PKCat (Sigma); FAK and phosphorylated FAK (Tyr397) (BD Bioscience); PDK and phosphorylated PDK1(ser241), Akt and phosphorylated Akt (Ser473), phosphorylated-Src (Tyr416), Erk1/2 and phosphorylated 44/42 Erk1/2, (Thr202/Tyr204), anti-β-catenin and phosphorylated-Histone H3(Ser10) (Cell signaling technology).

Immunohistochemistry, Phospho-Histone H3 (Ser10): FFPE of lung sections were stained with anti-p-Histone3 antibody according to the manufacturer's protocol.

Flow cytometry analysis: Tumor cell preparations from cultured cell lines were stained by CSPG4-specific scFv-Fc C21 for 30 min, washed twice with PBS, and incubated for 30 min with PE-labeled anti-human IgG antibody. After 3 washes, cells were analyzed by flow cytometry. scFv-Fc 119 was used as isotype control.

Western blotting: Western blot assay for signaling related proteins was performed using standard techniques on the lysates prepared from: i) cultured MV3 cells ($2\times10^4$ cells/well in a 96-well plate) serum starved for 72 hours, incubated with either scFv-Fc C21 (50 µg/ml), isotype matched control (50 µg/ml) or PBS for an additional 48 hrs, and lysed in lysis buffer (10 mM Tris-HC, 1% NP40, 1 mM EDTA, 0.1% BSA, 150 mM NaCl, 1/50 of protease inhibitor cocktail (Calbiochem); and ii) snap frozen surgically removed xenografts homogenized before and after adding an ice-cold RIPA buffer (Thermo Scientific) containing 1/50 of protease inhibitor cocktail (Calbiochem). After vortexing for 60 seconds, samples were ice-cooled for 45 minutes. Insoluble material was removed from tissue lysates by centrifugation at 13,000 rpm for 30 minutes at 4° C. Protein concentration was measured by Bradford reagent (Bio-Rad). Equal amounts of clarified lysate protein were separated by sodium dodecyl sulfate-polyacrylamide gel electrophoresis and transferred onto 0.45-µm (pore size) PVDF (Millipore). After blocking with 5% nonfat dry milk plus 2% BSA for 2 hour at room temperature, membranes were probed with anti-PKCα, anti-phosphorylated FAK, anti-FAK, anti-PDK, anti-phosphorylated PDK1(ser241), anti-phosphorylated Akt, anti-Akt, anti-phosphorylated Src (Tyr416), anti-anti-Erk1/2, anti-phosphorylated Erk1/2 (Thr202/Tyr204), anti-β-Catenin, and HLA class I antibody HC-10 (0.2 µg/ml) or anti-calnexin mAb To5 (0.2 µg/ml) overnight at 4° C., and then with secondary antibody. Bands were visualized with the Enhanced Chemiluminescence System (GE Life Science), and band density was read with the FOTO/ANA-LYST® Investigator Eclipse system (Fotodyne Incorporate) and quantified with TOTALLAB™ TL100 software (Nonlinear Dynamics). HLA class I or calnexin was used as the loading controls.

Cell growth and migration: For cell growth assay, cells ($5\times10^4$/well) were serum starved for 48 hrs and then seeded in a 96-well plate containing 4 times diluted MATRIGEL™ (growth factor-reduced MATRIGEL™-CB-40230, BD Biosciences) and either scFv-Fc C21 (0.5 mg/ml), control scFv-Fc 119 (0.5 mg/ml) or PBS in serum free RPMI 1640 medium (total volume 200 l/well) and cultured at 37° C. in a 5% $CO_2$ atmosphere for 6 days. For migration assay, cells ($5\times10^4$/well) were serum starved 48 hours and then seeded in a 24-transwell plate (24-well insert, pore size 8 µm; BD Biosciences) with scFv-Fc C21 (0.5 mg/ml), control scFv-Fc 119 (0.5 mg/ml) or PBS. Cells migrated toward to serum-free RPMI1640 medium containing 10 µg/ml fibronectin. After 48 hours, migrated cells were stained with HEMA 3 stain set, taken picture and counted under a Zeiss Inverted Fluorescence Microscope (AxioVision Software). Mean of six independent high power field (200×) are shown as columns. All above experiments were performed in triplicates.

Experimental lung metastasis and antibody administration: SCID mice were intravenously injected with cells MV3 and treated with scFv-Fc C21, as indicated in FIG. 16

Figure 18:
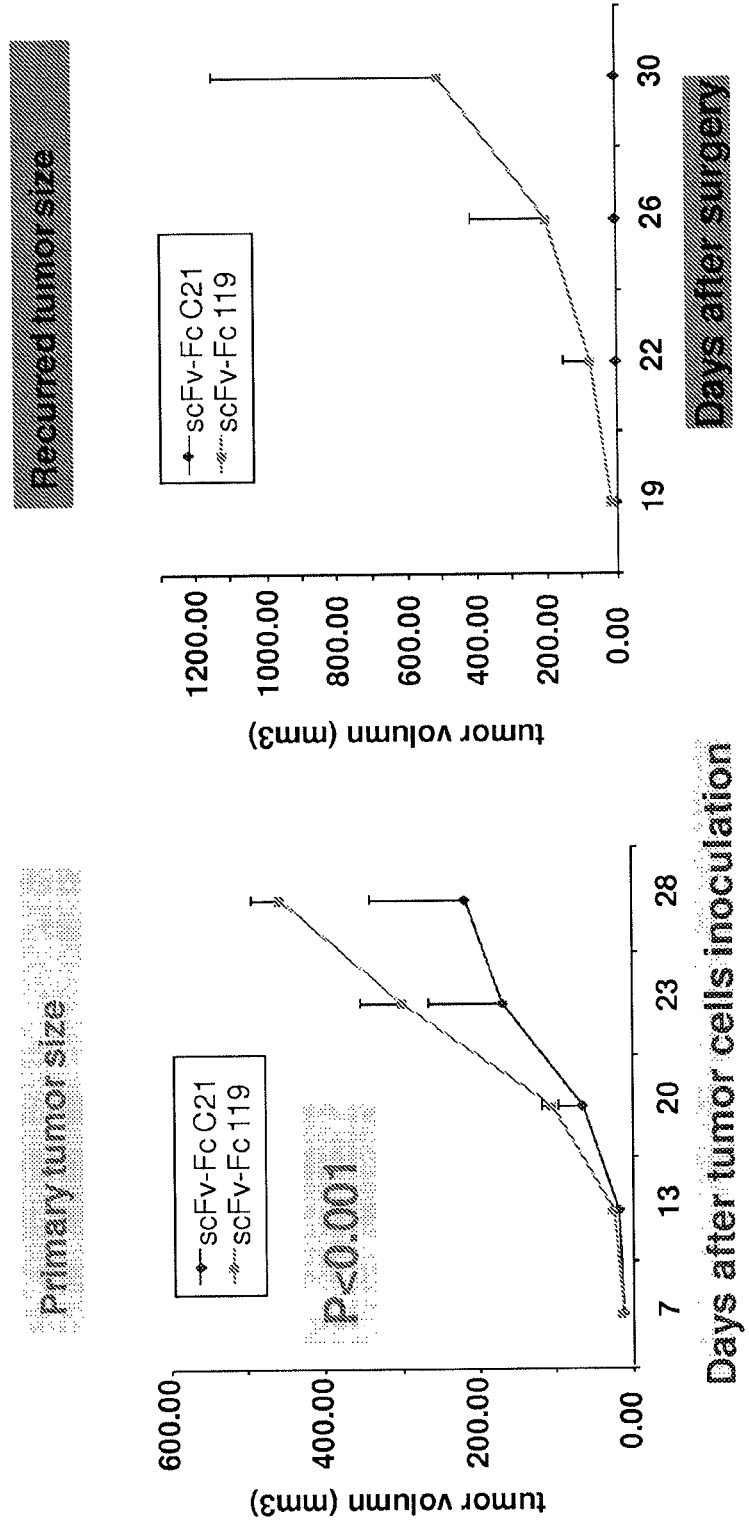
FIG. 18. Inhibition of primary tumor growth and local tumor recurrence by scFv-Fc C21. The protocol was as follows: Day 0: S.C. inoculation of tumor cells MV3 1.5× 10$^6$/per mouse; Day7: i.v. scFv-Fc (100 µg) administration, 2×weekly; Day 28: surgical removal of tumor; Day 35: i.v. scFv-Fc (100 µg) administration, 2×weekly; Day 61: sacrifice of mice due to the size of recurred tumor reached to the limit set by IACUC.

Spontaneous lung metastasis and treatment experiments: MV3 cells were implanted subcutaneously into SCID mice. Primary tumors were surgically removed while the mice were fully anesthetized using Ketamine (5 mg/kg, intraperitoneally (i.p.)) and continuous isoflurane inhalation. After the surgery, the mice were given the analgesic drug Ketoprofen (5 mg/kg, subcutaneous (s.c.) administration) daily for 3 days. scFc-Fc C21 were administered as indicated in FIG. 18.

Example 7

Reactivity of scFv-Fc C21 with a Panel of Human Tumor Cell Lines

Figure 15:
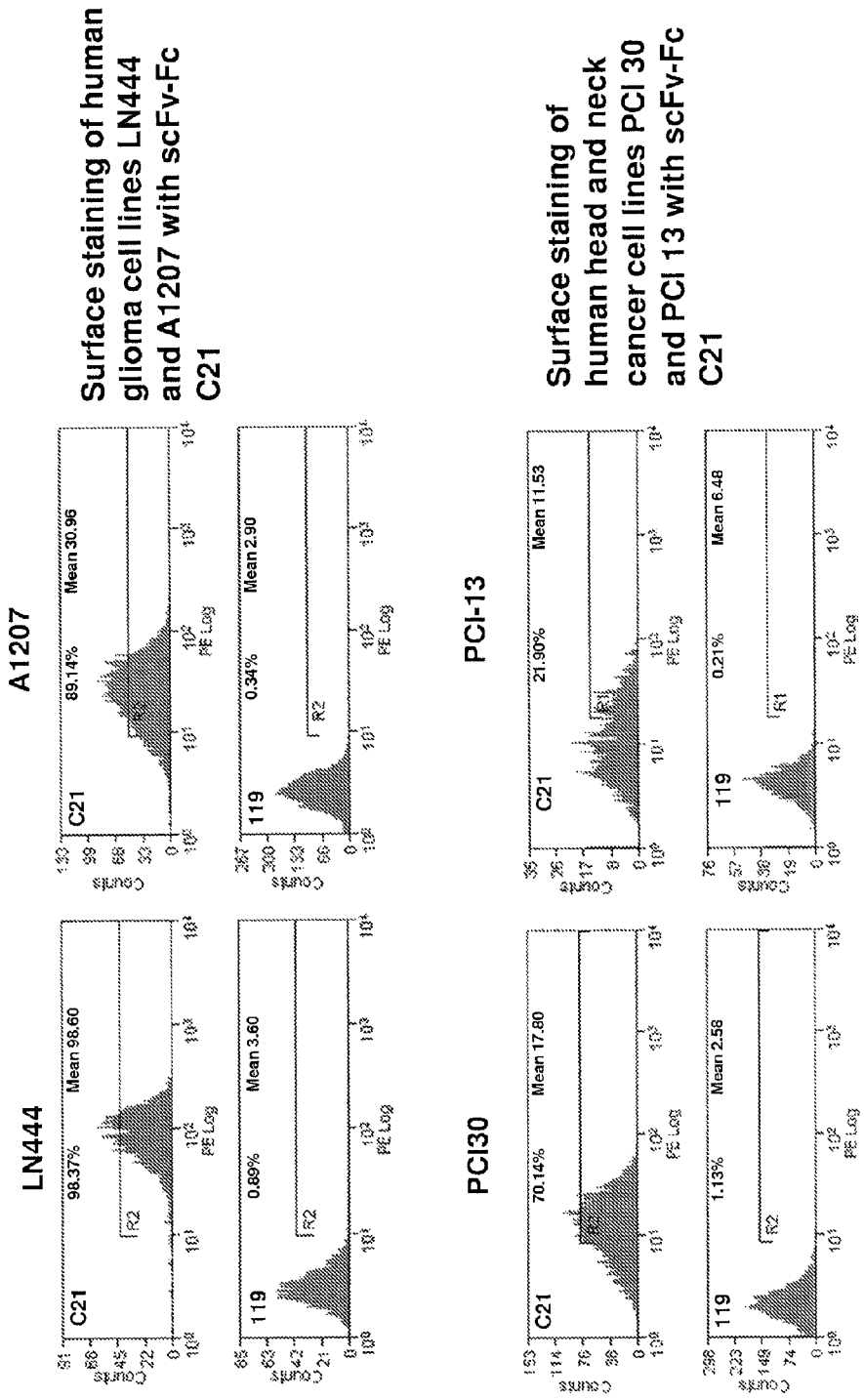
FIG. 15. Flow analysis showing surface staining of human glioma cell lines LN444 and A1207 with scFv-Fc C21 and surface staining of human head and neck cancer cell lines PCI 30 and PCI 13 with scFv-Fc C21.

Flow analysis has shown that scFv-Fc C21 stained specifically the cell surface of a panel of human cultured cell lines, including melanoma cell lines MDA-MB-435, MV3 and WM1158; glioma cell lines LN444 and A1207 and head and neck cancer cell line PCI30 and PCI13. CSPG4-melanoma cell line M14 was used as a negative control and M14/CSPG4, which is a CSPG4 transfectant of M14 cell line, was used as a positive control (see FIGS. 14-15).

Example 8

Figure 22:
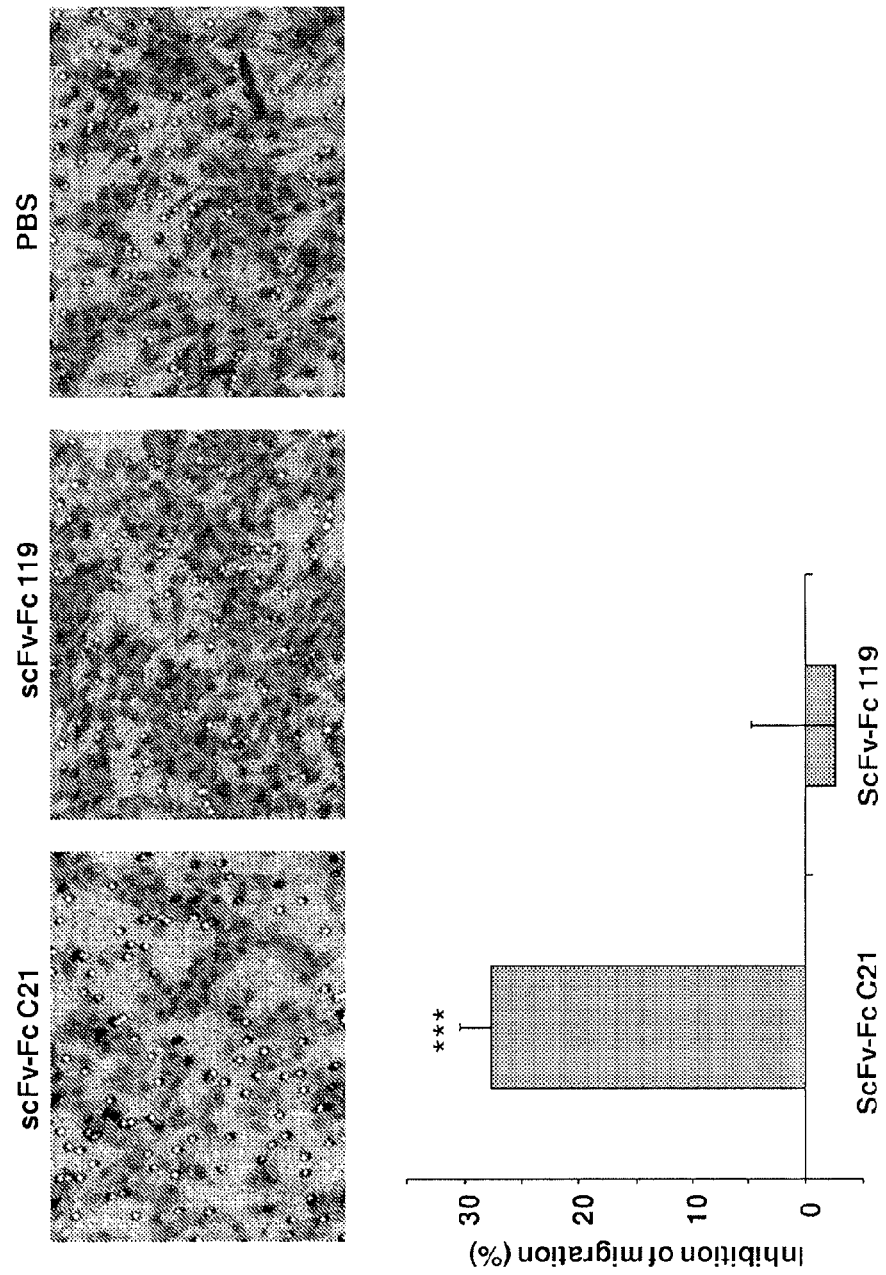
FIG. 22. Digital image and graph showing the inhibition of MDA-MB-231 in vitro cell migration by scFv-Fc C21. MDA-MB-231 cells were seeded and incubated with either scFv-Fc C21, control scFv-Fc 119 or PBS in a migration assay. The pictures were taken under Zeiss Inverted Fluorescence Microscope (AxioVision Software) of each well (×200). The results are expressed as % inhibition of migration, utilizing the values obtained in PBS without antibody as a reference. The values shown are the mean of three independent experiments. *** indicates p<0.001.
Figure 23:
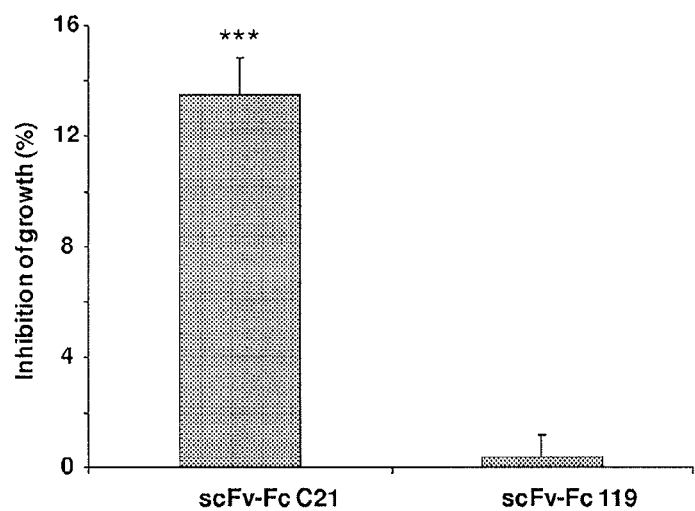
FIG. 23. Graph of inhibition of MDA-MB-231 in vitro cell growth by scFv-Fc C21. MDA-MB-231 cells were treated either with scFv-Fc C21 or control scFv-Fc 119 in a 3-D (matrigel) setting for 6 days. The PBS, which was used as the solvent for both antibodies, was used as a reference for 100% cell growth. Cells in each well were then harvested from matrigel using Cell Recovery Solution (BD Pharmingen) and counted using Trypan Blue by two individuals. The results are expressed as % inhibition of cell growth, utilizing the values obtained in PBS only as a reference. The values shown are the mean of two independent experiments. *** indicates p<0.001

Inhibition by scFv-Fc C21 of Tumor Cell Growth, and Migration scFv-Fc21 inhibited tumor cell growth and migration in vitro (FIGS. 22-23). The methods are described above in Example 6.

Example 9

Figure 24:
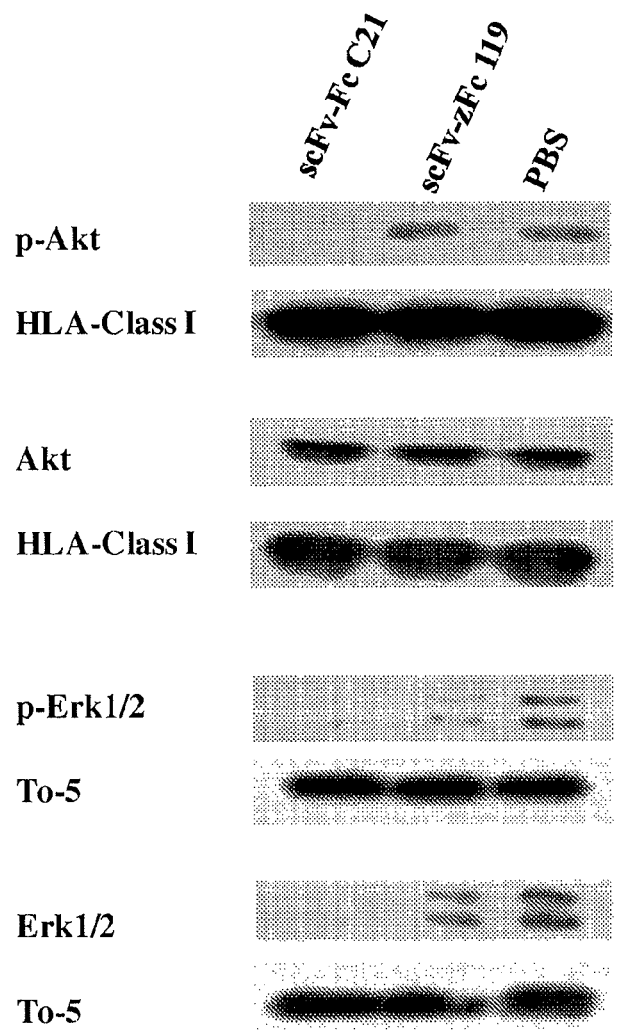
FIG. 24. Digital images of Western blots. The levels of p-Akt, p-Erk1/2 and Erk1/2 are significantly decreased following treatment with scFv-Fc C21.
Figure 25:
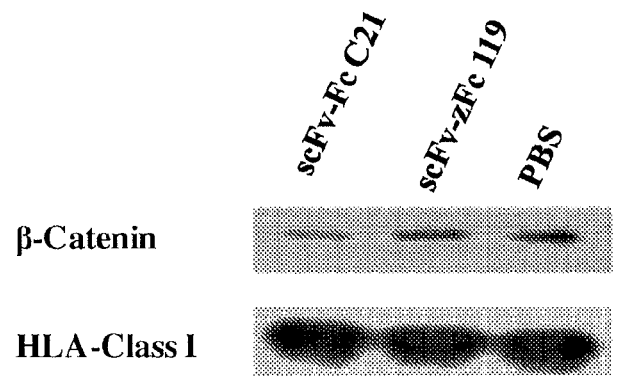
FIG. 25. Digital images of a Western blot. p-Catenin is decreased following treatment with scFv0Fc C21. β-Catenin is involved in cell-cell adhesion, cell signaling and gene transcription that are disrupted during malignant transformation. The oncogenic effect of Notch1 on primary melanoma cells was mediated by p-catenin, which was upregulated following Notch1 activation. Inhibiting β-catenin expression reversed Notch1-enhanced tumor growth and metastasis (see also Klara B. et al., *J. Clin. Invest.* 115(11): 3166-3176, 2005).
Figure 26:
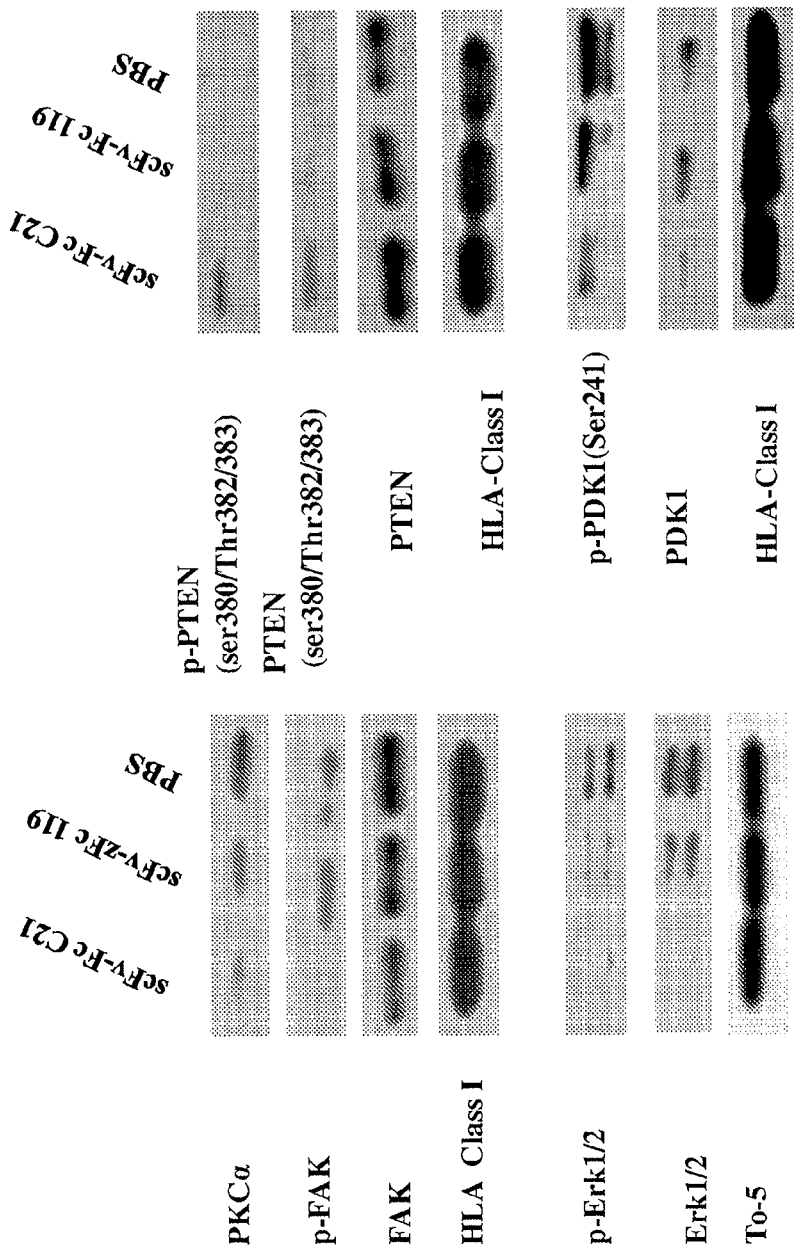
FIG. 26. Digital images of Western blots. The levels of p-PTEN (ser380/Thr382/383), non-phospho PTEN (ser380/Thr382/383), and PTEN are increased following treatment with scFv-Fc C21. The levels of phosphoinositide-dependent protein kinase (PDK1) are decreased following treatment with scFv-Fc C21. The levels of PKCα, p-FAK, and FAK are decreased.

Inhibition In Vitro of Multiple Signaling Pathways, which are Important to Tumor Cell Growth, Survival and Metastasis scFv-Fc C21 treated MV3 cells had a decreased level of Protein kinase C alpha (PKCα) and FAK. Moreover, scFv-Fc C21 treatment inhibited the phosphorylation/activation of FAK, Erk1/2, PDK1 (upstream of Akt) and Akt. The decreased Akt activation was accompanied with an increase in phosphorylated/activated PTEN, a negative regulator of PI3K/Akt pathway signaling (see FIGS. 24-26).

Example 10

Inhibition by scFc-Fc C21 of Human Melanoma Established Experimental Metastasis In Vivo scFc-Fc C21 inhibited significantly experimental metastases of MV3 cells (FIG. 16). Metastatic lesions were also evaluated for the rate of tumor cell proliferation using the surrogate marker p-Histone H3. The treatment of scFc-Fc C21 significantly reduced the number of mitotic cells (FIG. 17).

Example 11

Figure 19:
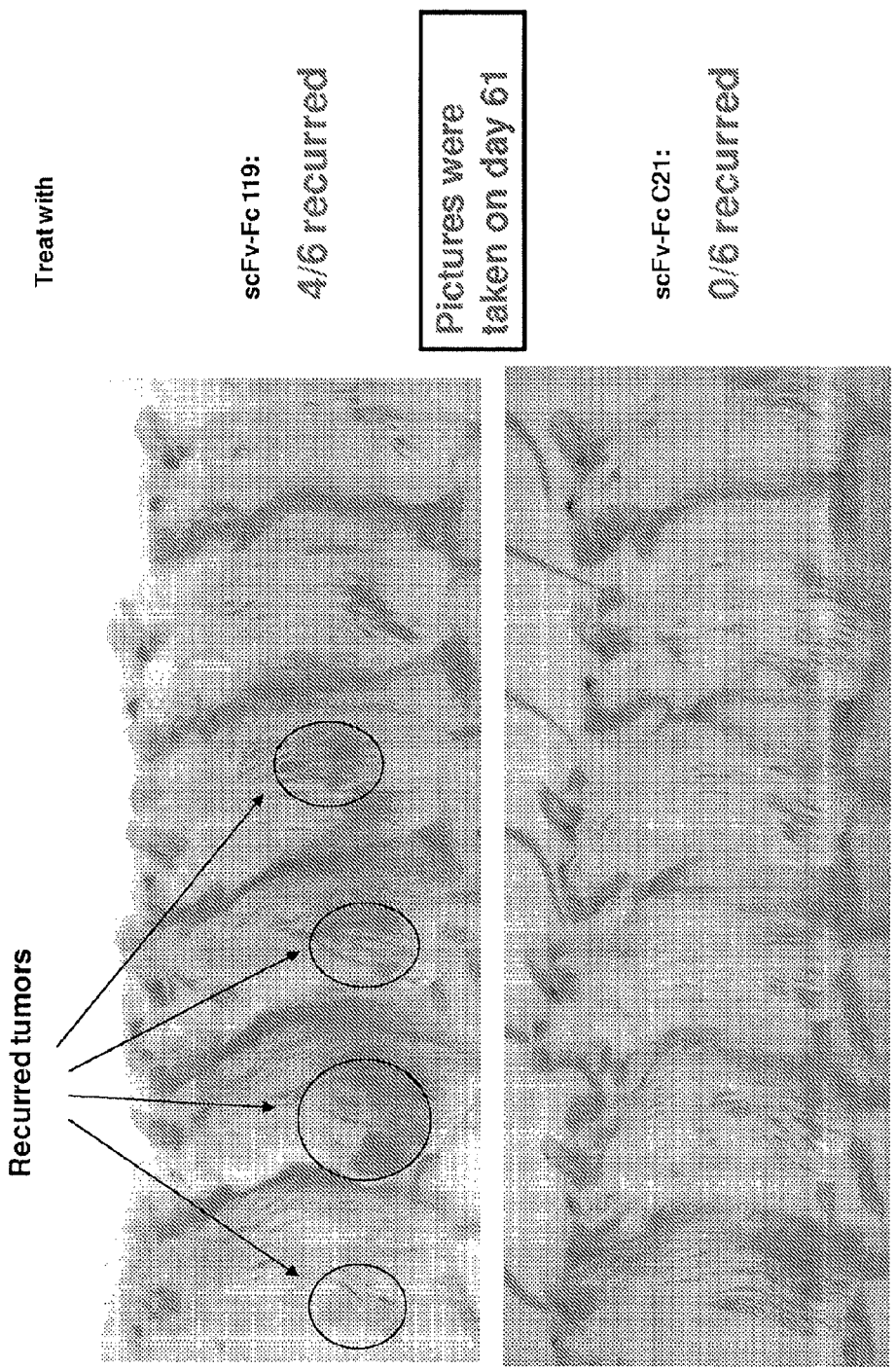
FIG. 19. Digital image showing inhibition of local tumor recurrence by scFv-Fc C21 in mice.
Figure 20:
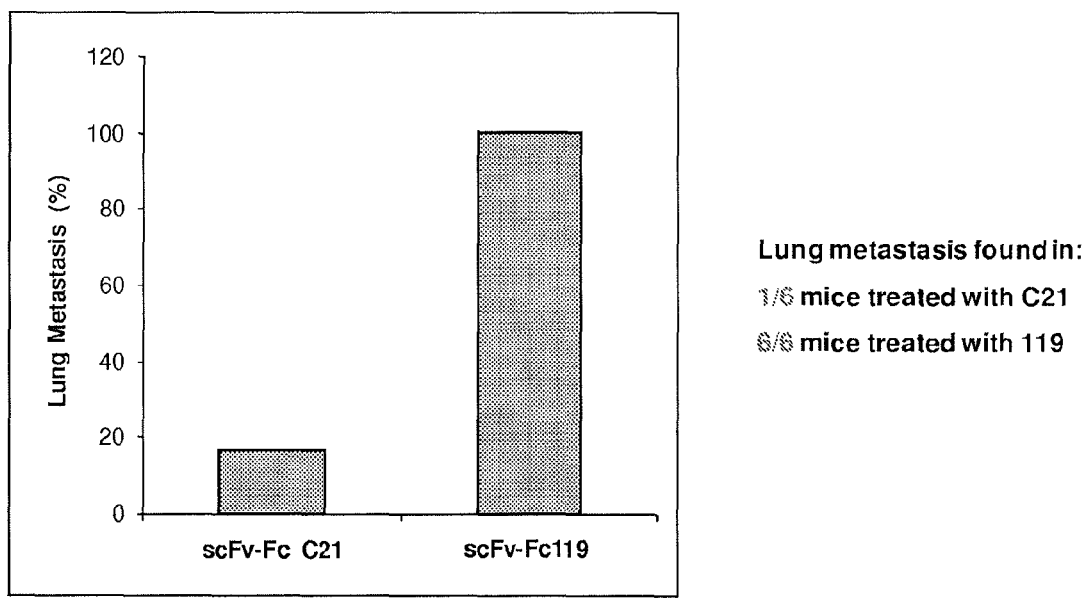
FIG. 20. Inhibition of post surgery spontaneous lung metastasis in mice by scFv-Fc C21.
Figure 21:
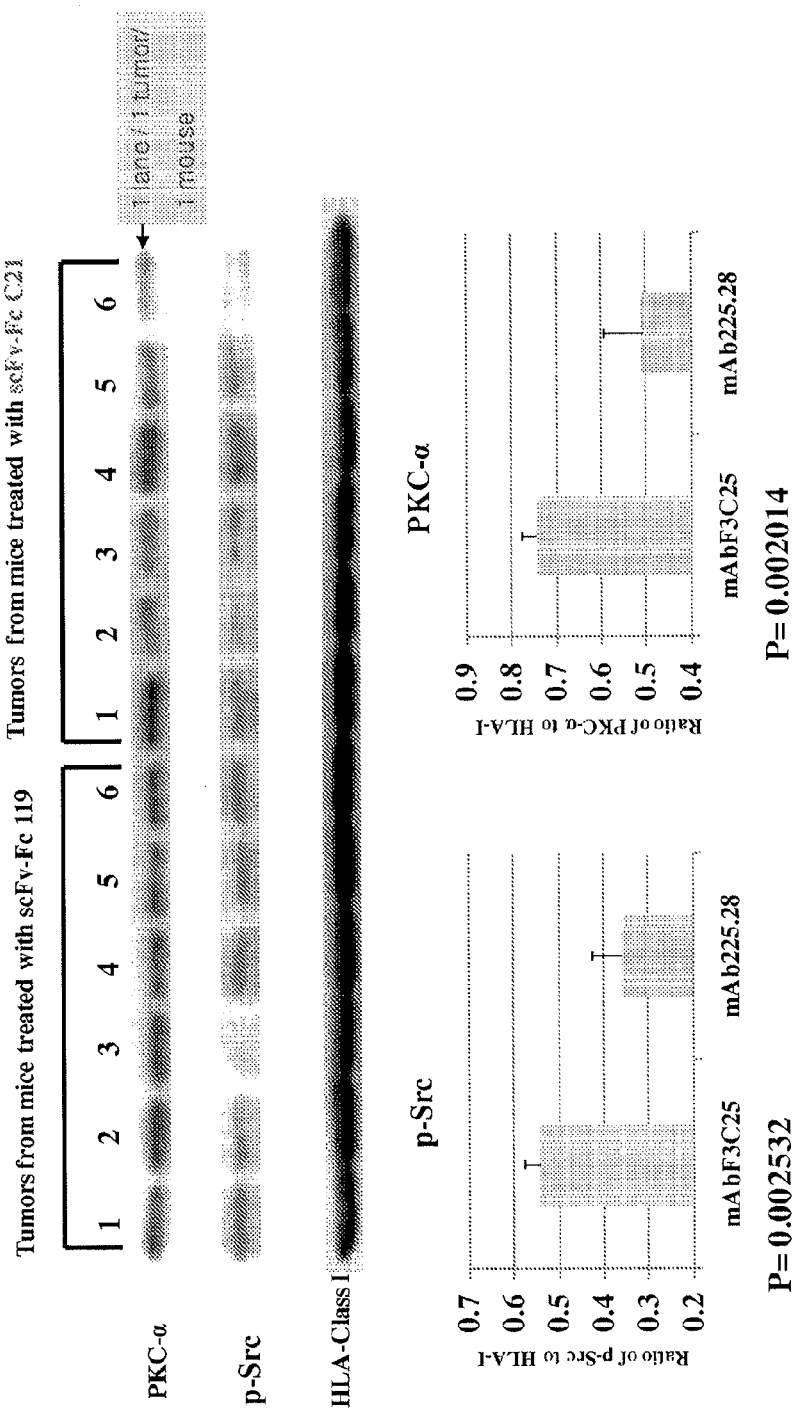
FIG. 21 Digital images and graphs showing decreased PKC-α and p-Src levels in surgically removed primary MV3 tumor tissues.

Inhibition by scFc-Fc C21 of Human Melanoma Post-Surgery Recurrence and Spontaneous Metastasis In Vivo The ability of scFc-Fc C21 to inhibit tumor recurrence and spontaneous metastasis of MV3 tumors in SCID mice was tested following surgical removal of primary tumors. Mice treated with scFc-Fc C21 had significantly lower rate of tumor recurrence and lower levels of spontaneous lung metastases than those receiving a control scFv-Fc (FIGS. 18-20). Additionally, primary tumors surgically removed from mice treated with scFc-Fc C21 were also evaluated for the activation of specific signal transduction pathways associated with melanoma growth and progression. The activation of PKC-a and Src signaling pathways was markedly reduced in the primary tumors removed from the mice treated with scFv-Fc C21 as compared to those removed from the mice treated with the control scFv-Fc 119 (FIG. 21).

This disclosure provides fully human antibodies specific for HMW-MAA. The disclosure further provides methods of treating or detecting cancers associated with expression of HMW-MAA, and methods of treatment using these antibodies. It will be apparent that the precise details of the methods described may be varied or modified without departing from the spirit of the described disclosure. We claim all such modifications and variations that fall within the scope and spirit of the claims below.

The invention claimed is:

1. An isolated nucleic acid molecule encoding a HMW-MAA-specific monoclonal antibody or antigen-binding fragment thereof, wherein the heavy chain variable region of the antibody or antigen-binding fragment thereof comprises amino acids 27-38, 56-55 and 105-115 of SEQ ID NO: 5, and the light chain variable region of the antibody or antigen-binding fragment thereof comprises amino acids 27-38, 56-65 and 105-110 of SEQ ID NO: 6.

2. The isolated nucleic acid molecule of claim 1, wherein the heavy chain variable region of the antibody or antigen-binding fragment thereof comprises SEQ ID NO: 5.

3. The isolated nucleic acid molecule of claim 1, wherein the light chain variable region of the antibody or antigen-binding fragment thereof comprises SEQ ID NO: 6.

4. The isolated nucleic acid molecule of claim 1, wherein the heavy chain variable region of the antibody or antigen-binding fragment thereof comprises SEQ ID NO: 5, and the light chain variable region of the antibody or antigen-binding fragment thereof comprises SEQ ID NO: 6.

5. The isolated nucleic acid molecule of claim 1 operably linked to a promoter.

6. An expression vector comprising the isolated nucleic acid molecule of claim 1.

7. An isolated host cell transformed with the expression vector of claim 6.

8. An isolated host cell transformed with the nucleic acid molecule of claim 1.

* * * * *